United States Patent
Gautier et al.

(10) Patent No.: US 10,138,278 B2
(45) Date of Patent: Nov. 27, 2018

(54) FLUOROGEN ACTIVATING AND SHIFTING TAG (FAST)

(71) Applicants: PARIS SCIENCES ET LETTRES -QUARTIER LATIN, Paris (FR); CENTRE NATIONAL DE LA RECHERCHE SCIENTIFIQUE (CNRS), Paris (FR); UNIVERSITE PIERRE ET MARIE CURIE—PARIS 6 (UPMC), Paris (FR)

(72) Inventors: Arnaud Gautier, Paris (FR); Ludovic Jullien, Arcueil (FR)

(73) Assignees: PARIS SCIENCES ET LETTRES—QUARTIER LATIN, Paris (FR); CENTRE NATIONAL DE LA RECHERCHE SCIENTIFIQUE(CNRS), Paris (FR); UNIVERSITE PIERRE ET MARIE CURIE—PARIS 6 (UPMC), Paris (FR)

( * ) Notice: Subject to any disclaimer, the term of this patent is extended or adjusted under 35 U.S.C. 154(b) by 0 days.

(21) Appl. No.: 15/321,378

(22) PCT Filed: Jul. 3, 2015

(86) PCT No.: PCT/EP2015/065267
§ 371 (c)(1),
(2) Date: Dec. 22, 2016

(87) PCT Pub. No.: WO2016/001437
PCT Pub. Date: Jan. 7, 2016

(65) Prior Publication Data
US 2017/0137473 A1    May 18, 2017

(30) Foreign Application Priority Data
Jul. 4, 2014 (EP) .................................... 14175837

(51) Int. Cl.
| | | |
|---|---|---|
| C07K 16/14 | (2006.01) | |
| A61K 38/00 | (2006.01) | |
| C07H 21/04 | (2006.01) | |
| C07K 14/195 | (2006.01) | |
| C07D 277/36 | (2006.01) | |
| G01N 33/566 | (2006.01) | |
| G01N 33/58 | (2006.01) | |

(52) U.S. Cl.
CPC .......... *C07K 14/195* (2013.01); *C07D 277/36* (2013.01); *G01N 33/566* (2013.01); *G01N 33/582* (2013.01); *C07K 2319/60* (2013.01)

(58) Field of Classification Search
CPC ...... C12N 9/0006; C01N 33/53; A61K 38/00; C07K 14/195; G01N 33/566

USPC ........... 435/7.9, 528, 7.6; 436/510, 536, 538
See application file for complete search history.

(56) References Cited

PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Chudakov D.M. et al., "Fluorescent Proteins and Their Applications in Imaging Living Cells and Tissues.", Physiol Rev., Jul. 2010; vol. 90(3), pp. 1103-1163, Austin, Texas.
Hansen M.C. et al., "Assessment of GFP fluorescence in cells of *Streptococcus gordonii* under conditions of low pH and low oxygen concentration.", Microbiology, May 2001; vol. 147(Pt 5), pp. 1383-1391, Lyngby, Denmark.
Shaner N. et al., "A guide for choosing fluorescent proteins." Nature Methods, Dec. 2005; vol. 2 No. 12; pp. 905-909, La Jolla, CA.
Shu X. et al.; "Mammalian Expression of Infrared Fluorescent Proteins Engineered from a Bacterial Phytochrome." Science, May 8, 2009; vol. 324 No. 5928, pp. 804-807, La Jolla, CA.
Filonov G.S. et al., "Bright and stable near-infrared fluorescent protein for in vivo imaging.", Nature Biotechnology, Jul. 17, 2011; vol. 29 No. 8, pp. 757-761, Bronx, New York.
Auldridge M.E. et al., "Structure-guided Engineering Enhances a Phytochrome-based Infrared Fluorescent Protein.", The Journal of Biological Chemistry, Mar. 2, 2012; vol. 287 No. 10, pp. 7000-7009, Madison, Wisconsin.
Chapman S. et al., "The photoreversible fluorescent protein iLOV outperforms GFP as a reporter of plant virus infection."; Proc National Academy of Sciences of the USA (PNAS); Dec. 16, 2008; vol. 105 No. 50; pp. 20038-20043, Dundee, United Kingdom.
Drepper T. et al., "Reporter proteins for in vivo fluorescence without oxygen."; Nature Biotechnology, Apr. 2007; vol. 25 No. 4, pp. 443-445, Juelich, Germany.
Shu X. et al., "A Genetically Encoded Tag for Correlated Light and Electron Microscopy of Intact Cells, Tissues, and Organisms.", PLoS Biology, Apr. 2011; vol. 9 No. 4, pp. e1001041; San Francisco, California.

(Continued)

*Primary Examiner* — Robert B Mondesi
*Assistant Examiner* — Mohammad Y Meah
(74) *Attorney, Agent, or Firm* — Young & Thompson

(57) ABSTRACT

Disclosed is a functional derivative of a Photoactive Yellow Protein (PYP), or a functional fragment thereof, for fluorescently labelling particles, e.g. proteins, or surfaces, which is capable of binding reversibly a fluorogenic chromophore of formula (I), and which is capable of enhancing the brightness of the fluorogenic chromophore upon complexation thereto; and of inducing the spectral shift of the fluorogenic chromophore through the ionization of an auxochromic group thereof.

15 Claims, 17 Drawing Sheets
Specification includes a Sequence Listing.

(56) References Cited

PUBLICATIONS

Kumagai A. et al., "A Bilirubin-Inducible Fluorescent Protein from Eel Muscle." Cell, Elsevier Inc., Jun. 20, 2013; vol. 153 No. 7, pp. 1602-1611; Saitama, Japan.

Ozhalici-Unal H. et al., "A rainbow of fluoromodules: A promiscuous scFv protein binds to and activates a diverse set of fluorogenic cyanine dyes.", Journal of American Chemical Society, Sep. 24, 2008; vol. 130 No. 38, pp. 12620-12621, Athens, GA.

Shank N.I. et al., "Enhanced Photostability of Genetically Encodable Fluoromodules Based on Fluorogenic Cyanine Dyes and a Promiscuous Protein Partner.", Journal of American Chemical Society, Sep. 16, 2009; vol. 131 No. 36, pp. 12960-12969, Pittsburgh, PA.

Szent-Gyorgyi C. et al., "Fluorogen-activating single-chain antibodies for imaging cell surface proteins.", Nature Biotechnology, Feb. 2008; vol. 26 No. 2, pp. 235-240, Pittsburgh, PA.

Heim R. et al., "Improved green fluorescence.", Nature, Scientific Correspondence, Feb. 23, 1995; vol. 373 No. 6516; pp. 663-664, La Jolla, CA.

Tsien R.Y., "The green fluorescent protein." Annual Review of Biochemistry, 1998; vol. 67, 99:509-544, La Jolla, CA.

Bourdoncle A. et al., "Quadruplex-based molecular beacons as tunable DNA probes.", Journal of American Chemical Society. Aug. 30, 2006; vol. 128 No. 34, pp. 11094-11105, Paris, France.

Derbyshire K.M. et al., "A simple and efficient procedure for saturation mutagenesis using mixed oligodeoxynucleotides.", Gene. Elsevier Science Publishers B.V. (Biomedical Division), 1986; vol. 46 No. 2-3, pp. 145-152, New Haven, CT.

Miyazaki K. and Arnold F.H., "Exploring Nonnatural Evolutionary Pathways by Saturation Mutagenesis: Rapid Improvement of Protein Function." Journal of Molecular Evolution. 1999; vol. 49, pp. 716-720, Pasadena, CA.

Steffens D.L. and Williams J.G.K., "Efficient site-directed saturation mutagenesis using degenerate oligonucleotides.", Journal of Biomolecular Techniques. Jul. 2007; vol. 18 No. 3, pp. 147-149, Lincoln, NE.

Wang J. et al., "PCR-based strategy for construction of multi-site-saturation mutagenic expression library.", Journal of Microbiological Methods. Dec. 2007; vol. 71 No. 3, pp. 225-230, Dalian, PR China.

Zheng L. et al., "An efficient one-step site-directed and site-saturation mutagenesis protocol.", Nucleic Acids Research, Aug. 10, 2004; vol. 32 No. 14, pp. e115, Berne, Switzerland.

Chao G. et al., "Isolating and engineering human antibodies using yeast surface display.", Nature Protocols, 2006; vol. 1 No. 2, pp. 755-768, Cambridge, Massachusetts.

Gietz R.D. and Schiestl R.H., "Large-scale high-efficiency yeast transformation using the LiAc/SS carrier DNA/PEG method.", Nature Protocols, 2007; vol. 2 No. 1, pp. 38-41, Manitoba, Canada.

Borgstahl G. et al., "1.4 .Ang. Structure of Photoactive Yellow Protein, a Cytosolic Photoreceptor: Unusual Fold, Active Site, and Chromophore.", Biochemistry, 1995, vol. 34 No. 19, pp. 6278-6287, La Jolla, California.

Borucki B. et al., "Effect of Salt and pH on the Activation of Photoactive Yellow Protein and Gateway Mutants Y98Q and Y98F." Biochemistry, 2005, vol. 44 No. 42, pp. 13650-13663, Berlin, Germany.

Mihara K. et al., "Functional expression and site-directed mutagenesis of photoactive yellow protein." Journal Biochemistry. May 1997; vol. 121 No. 5, pp. 876-880, Osaka, Japan.

Chosrowjan H. et al., "Environmental Effects on the Femtosecond-Picosecond Fluorescence Dynamics of Photoactive Yellow Protein: Chromophores in Aqueous Solutions and in Protein Nanospaces Modified by Site-Directed Mutagenesis.", The Journal of Physical Chemistry B, 1998, vol. 102 No. 40, pp. 7695-7698, Osaka, Japan.

Kyndt J.A. et al., "Rhodobacter capsulatus Photoactive Yellow Protein: Genetic Context, Spectral and Kinetics Characterization, and Mutagenesis." Biochemistry, 2004, vol. 43 No. 7, pp. 1809-1820, Gent, Belgium.

Khodair A., "A convenient synthesis of 2-Arylidene-5H-thiazolo[2,3-b]quinazo-line-3,5[2H]-diones and their benzoquinazoline derivatives." Journal of Heterocyclic Chemistry, 2002, vol. 39, pp. 1153-1160, Kafr El-Sheikh, Egypt.

Hospes M. et al., "Tryptophan fluorescence as a reporter for structural changes in photoactive yellow protein elicited by photoactivation." Photochemical and Photobiological Sciences. Mar. 2013; vol. 12 No. 3, pp. 479-488, Amsterdam, Netherlands.

Hospes M. et al., "Tryptophan fluorescence as a reporter for structural changes in photoactive yellow protein elicited by photoactivation.", Photochemical and Photobiological Sciences. Mar. 2013; vol. 12 No. 3, pp. 479-488—supplementary information, Amsterdam, Netherlands.

Hospes M. Ph.D. Thesis: "Light responses of bacteria: site-directed mutagenesis study of PYP & photo-inactivation of *E. coli* and B. subtilis.", Nov. 13, 2012; whole document, Amsterdam, Netherlands.

Van Der Horst M.A. Ph.D. Thesis: "Structure/function relations in Photoactive Yellow Protein." whole document, Apr. 27, 2004, Amsterdam, Netherlands.

Kyndt J.A. et al., "Structural role of tyrosine 98 in photoactive yellow protein: effects on fluorescence, gateway, and photocycle recovery.", Biochemistry. Jan. 9, 2007; vol. 46 No. 1, pp. 95-105, Tuscan, Arizona.

International Search Report, dated Dec. 18, 2015, in corresponding International Patent Application No. PCT/EP2015/065267.

* cited by examiner

FIG. 15C 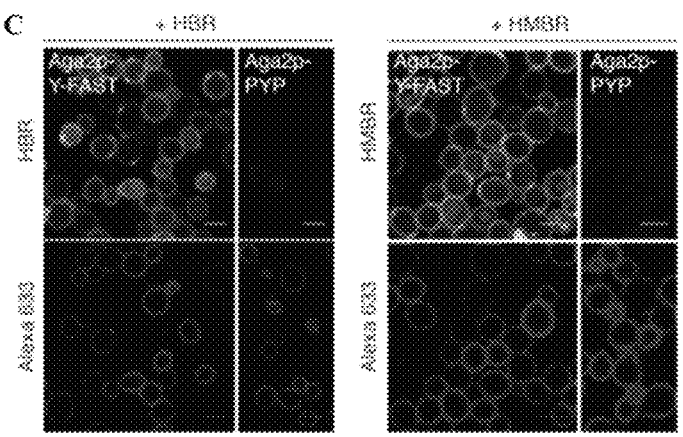 FIG. 15D
FIG. 15E 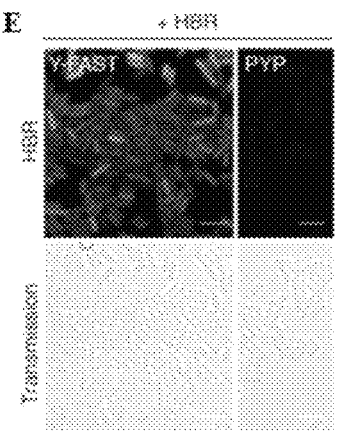 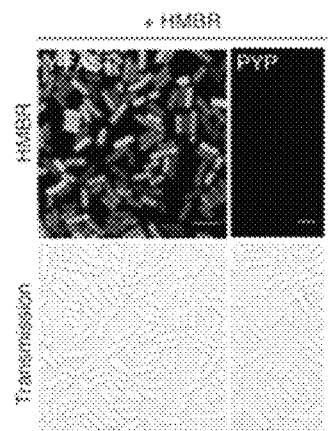 FIG. 15F

FIG. 19A Nucleus
FIG. 19B Plasma membrane
FIG. 19C Ensconsin (MBP)

SEQUENCE LISTING

<160> NUMBER OF SEQ ID NOS: 152

<210> SEQ ID NO 1
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone 1

<400> SEQUENCE: 1

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ile Ile
                85                  90                  95

Pro Thr Arg Asp Met Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 2
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone 2

<400> SEQUENCE: 2

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Leu Ile
                85                  90                  95

Pro Thr Leu Pro Gln Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 3
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone -continued

3

<400> SEQUENCE: 3

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Met Ile
                85                  90                  95

Pro Thr Ser Arg Gly Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 4
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      4

<400> SEQUENCE: 4

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Asp Ile
                85                  90                  95

Pro Thr Asn Pro Glu Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 5
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      5

<400> SEQUENCE: 5

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
65                   70                  75                  80

Glu Gly Val Ala Ser Gly Asn Leu Asn Thr Met Phe Glu Trp Arg Ile
                 85                  90                  95

Pro Thr Glu Cys Ala Pro Thr Lys Val Lys Val His Met Lys Lys Ala
            100                 105                 110

Leu Ser Gly Asp Ser Tyr Trp Val Phe Val Lys Arg Val
            115                 120                 125

<210> SEQ ID NO 6
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      6

<400> SEQUENCE: 6

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
65                   70                  75                  80

Glu Gly Val Ala Ser Gly Asn Leu Asn Thr Met Phe Glu Trp Leu Ile
                 85                  90                  95

Pro Thr Arg Asn Ala Pro Thr Lys Val Lys Val His Met Lys Lys Ala
            100                 105                 110

Leu Ser Gly Asp Ser Tyr Trp Val Phe Val Lys Arg Val
            115                 120                 125

<210> SEQ ID NO 7
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      7

<400> SEQUENCE: 7

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
65                   70                  75                  80

Glu Gly Val Ala Ser Gly Asn Leu Asn Thr Met Phe Glu Trp Ser Ile
                85                  90                  95

Pro Ala Arg Ser Ala Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 8
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      8

<400> SEQUENCE: 8

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Tyr Ile
                85                  90                  95

Pro Thr Gln Thr Ser Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 9
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      9

<400> SEQUENCE: 9

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Met Ile
                85                  90                  95

Pro Thr Glu His Val Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 10
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      10

<400> SEQUENCE: 10

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ala Ile
                85                  90                  95

Pro Thr His Thr Gln Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 11
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      11

<400> SEQUENCE: 11

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ser Ile
                85                  90                  95

Pro Ala Gly Lys Gly Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 12
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      12

```
<400> SEQUENCE: 12

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Val Ile
                85                  90                  95

Pro Arg Glu Asp Asn Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 13
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      13

<400> SEQUENCE: 13

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ser Ile
                85                  90                  95

Pro Gln Ile Met Ala Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 14
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      14

<400> SEQUENCE: 14

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30
```

```
Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Leu Val
                85                  90                  95

Pro Arg Ile Cys Gln Pro Thr Lys Val Lys Val His Met Lys Lys Ala
            100                 105                 110

Leu Ser Gly Asp Ser Tyr Trp Val Phe Val Lys Arg Val
            115                 120                 125

<210> SEQ ID NO 15
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      15

<400> SEQUENCE: 15

Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Thr Ile
                85                  90                  95

Pro Ala Leu Arg Lys Pro Thr Lys Val Lys Val His Met Lys Lys Ala
            100                 105                 110

Leu Ser Gly Asp Ser Tyr Trp Val Phe Val Lys Arg Val
            115                 120                 125

<210> SEQ ID NO 16
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      16

<400> SEQUENCE: 16

Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80
```

Glu Gly Val Ala Ser Gly Asn Leu Asn Thr Met Phe Glu Trp His Ile
                85                  90                  95

Pro Arg Asp Pro His Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 17
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      17

<400> SEQUENCE: 17

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ser Ile
                85                  90                  95

Pro Val Ser Gly Gln Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 18
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      18

<400> SEQUENCE: 18

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Thr Val
                85                  90                  95

Pro Thr Phe Ile Val Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 19
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      19

<400> SEQUENCE: 19

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
        50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Tyr Ile
                85                  90                  95

Pro Ala Asn His Lys Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 20
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      20

<400> SEQUENCE: 20

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
        50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Val Ile
                85                  90                  95

Pro Pro Phe Glu Ser Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 21
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      21

```
<400> SEQUENCE: 21

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Val Val
                85                  90                  95

Pro Asn Pro Ile Ala Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 22
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      22

<400> SEQUENCE: 22

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Gln Ile
                85                  90                  95

Pro Val Tyr Ala Val Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 23
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      23

<400> SEQUENCE: 23

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
```

```
                35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Gln Ile
                 85                  90                  95

Pro Thr Ser Ile Ile Pro Thr Lys Val Lys Val His Met Lys Lys Ala
                100                 105                 110

Leu Ser Gly Asp Ser Tyr Trp Val Phe Val Lys Arg Val
                115                 120                 125

<210> SEQ ID NO 24
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      24

<400> SEQUENCE: 24

Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
                35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Met Ile
                 85                  90                  95

Pro Gly Asp Gly Asp Pro Thr Lys Val Lys Val His Met Lys Lys Ala
                100                 105                 110

Leu Ser Gly Asp Ser Tyr Trp Val Phe Val Lys Arg Val
                115                 120                 125

<210> SEQ ID NO 25
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      25

<400> SEQUENCE: 25

Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
                35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Asp Ile
```

```
                    85                  90                  95

Pro His Asp Asp Ala Pro Thr Lys Val Lys Val His Met Lys Lys Ala
            100                 105                 110

Leu Ser Gly Asp Ser Tyr Trp Val Phe Val Lys Arg Val
            115                 120                 125

<210> SEQ ID NO 26
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      26

<400> SEQUENCE: 26

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ser Ile
                85                  90                  95

Pro Ser Val Arg His Pro Thr Lys Val Lys Val His Met Lys Lys Ala
            100                 105                 110

Leu Ser Gly Asp Ser Tyr Trp Val Phe Val Lys Arg Val
            115                 120                 125

<210> SEQ ID NO 27
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      27

<400> SEQUENCE: 27

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Phe Ile
                85                  90                  95

Pro Lys Gly His Lys Pro Thr Lys Val Lys Val His Met Lys Lys Ala
            100                 105                 110

Leu Ser Gly Asp Ser Tyr Trp Val Phe Val Lys Arg Val
            115                 120                 125
```

```
<210> SEQ ID NO 28
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      28

<400> SEQUENCE: 28

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Arg Ile
                85                  90                  95

Pro Lys Pro Thr Ala Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 29
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      29

<400> SEQUENCE: 29

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ala Val
                85                  90                  95

Pro Gly Val Cys Gly Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 30
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      30

<400> SEQUENCE: 30
```

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Arg Ile
                85                  90                  95

Pro Gly Glu Met Phe Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 31
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      31

<400> SEQUENCE: 31

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ser Val
                85                  90                  95

Pro Thr Thr Arg Leu Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 32
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      32

<400> SEQUENCE: 32

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

```
Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Phe Val
                 85                  90                  95

Pro Gly Pro Ser Val Pro Thr Lys Val Lys Val His Met Lys Lys Ala
            100                 105                 110

Leu Ser Gly Asp Ser Tyr Trp Val Phe Val Lys Arg Val
            115                 120                 125
```

<210> SEQ ID NO 33
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      33

<400> SEQUENCE: 33

```
Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
                 20                  25                  30

Leu Asp Gly Asp Gly Asn Ile Leu Gln Tyr Asn Ala Ala Glu Gly Asp
             35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Arg Ile
                 85                  90                  95

Pro Arg Arg Val Val Pro Thr Lys Val Lys Val His Met Lys Lys Ala
            100                 105                 110

Leu Ser Gly Asp Ser Tyr Trp Val Phe Val Lys Arg Val
            115                 120                 125
```

<210> SEQ ID NO 34
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      34

<400> SEQUENCE: 34

```
Met Glu His Val Ala Phe Gly Ser Glu Asp Ile Glu Asn Thr Leu Ala
 1               5                  10                  15

Lys Met Asp Asp Gly Gln Leu Asp Gly Leu Ala Phe Gly Ala Ile Gln
                 20                  25                  30

Leu Asp Gly Asp Gly Asn Ile Leu Gln Tyr Asn Ala Ala Glu Gly Asp
             35                  40                  45

Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Thr Leu
                 85                  90                  95
```

```
Pro Ala Trp His His Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 35
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      35

<400> SEQUENCE: 35

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Thr Ile
                85                  90                  95

Pro Val Leu Gly Thr Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 36
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      36

<400> SEQUENCE: 36

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Glu Ile
                85                  90                  95

Pro Ile Pro Thr Asn Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 37
```

```
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      37

<400> SEQUENCE: 37

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Val Ile
                85                  90                  95

Pro Asn Tyr Thr Met Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 38
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      38

<400> SEQUENCE: 38

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Tyr Ile
                85                  90                  95

Pro Ala Leu His Trp Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 39
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      39

<400> SEQUENCE: 39
```

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Gly Ile
                85                  90                  95

Pro Thr Pro Glu Glu Pro Thr Lys Val Lys Val His Met Lys Lys Ala
            100                 105                 110

Leu Ser Gly Asp Ser Tyr Trp Val Phe Val Lys Arg Val
            115                 120                 125

<210> SEQ ID NO 40
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      40

<400> SEQUENCE: 40

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Glu Ile
                85                  90                  95

Pro Met Gly Ala His Pro Thr Lys Val Lys Val His Met Lys Lys Ala
            100                 105                 110

Leu Ser Gly Asp Ser Tyr Trp Val Phe Val Lys Arg Val
            115                 120                 125

<210> SEQ ID NO 41
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      41

<400> SEQUENCE: 41

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

```
Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Ser Ile
                85                  90                  95

Pro Pro Gly Arg Gln Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 42
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      42

<400> SEQUENCE: 42

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Asn Leu
                85                  90                  95

Pro Val Lys Ala Pro Pro Thr Lys Val Lys Val His Met Lys Lys Ala
                100                 105                 110

Leu Ser Gly Asp Ser Tyr Trp Val Phe Val Lys Arg Val
            115                 120                 125

<210> SEQ ID NO 43
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      43

<400> SEQUENCE: 43

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
                20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Glu Val
                85                  90                  95
```

Pro Ala Glu Thr Met Pro Thr Lys Val Lys Val His Met Lys Lys Ala
              100                 105                 110

Leu Ser Gly Asp Ser Tyr Trp Val Phe Val Lys Arg Val
        115                 120                 125

<210> SEQ ID NO 44
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      44

<400> SEQUENCE: 44

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Arg Val
                85                  90                  95

Pro Asn Pro Thr Gly Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 45
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      45

<400> SEQUENCE: 45

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Leu Ile
                85                  90                  95

Pro Lys Pro Phe Ile Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 46
<211> LENGTH: 125

```
<212> TYPE: PRT
<213> ORGANISM: Artificial Sequence
<220> FEATURE:
<223> OTHER INFORMATION: Functional derivative of SEQ ID NO: 48 - Clone
      46

<400> SEQUENCE: 46

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Thr Val
                85                  90                  95

Pro Ser Thr Arg Leu Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 47
<211> LENGTH: 125
<212> TYPE: PRT
<213> ORGANISM: Artificial Sequence
<220> FEATURE:
<223> OTHER INFORMATION: Functional derivative of SEQ ID NO: 48 - Clone
      47

<400> SEQUENCE: 47

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Arg Trp Ile
                85                  90                  95

Pro Gly Lys Met Val Pro Thr Lys Val Lys Val His Met Lys Lys Ala
            100                 105                 110

Leu Ser Gly Asp Ser Tyr Trp Val Phe Val Lys Arg Val
        115                 120                 125

<210> SEQ ID NO 48
<211> LENGTH: 125
<212> TYPE: PRT
<213> ORGANISM: Halorhodospira halophila
<220> FEATURE:
<223> OTHER INFORMATION: C69G variant

<400> SEQUENCE: 48

Met Glu His Val Ala Phe Gly Ser Glu Asp Ile Glu Asn Thr Leu Ala
```

```
                1               5                    10                   15
Lys Met Asp Asp Gly Gln Leu Asp Gly Leu Ala Phe Gly Ala Ile Gln
                20                   25                   30

Leu Asp Gly Asp Gly Asn Ile Leu Gln Tyr Asn Ala Ala Glu Gly Asp
            35                   40                   45

Ile Thr Gly Arg Asp Pro Lys Gln Val Ile Gly Lys Asn Phe Phe Lys
        50                   55                   60

Asp Val Ala Pro Gly Thr Asp Ser Pro Glu Phe Tyr Gly Lys Phe Lys
65                   70                   75                   80

Glu Gly Val Ala Ser Gly Asn Leu Asn Thr Met Phe Glu Tyr Thr Phe
                85                   90                   95

Asp Tyr Gln Met Thr Pro Thr Lys Val Lys Val His Met Lys Lys Ala
                100                  105                  110

Leu Ser Gly Asp Ser Tyr Trp Val Phe Val Lys Arg Val
            115                  120                  125

<210> SEQ ID NO 49
<211> LENGTH: 125
<212> TYPE: PRT
<213> ORGANISM: Halorhodospira halophila

<400> SEQUENCE: 49

Met Glu His Val Ala Phe Gly Ser Gly Asp Ile Glu Asn Thr Leu Ala
1               5                    10                   15

Lys Met Asp Asp Gly Gln Leu Asp Gly Leu Ala Phe Gly Ala Ile Gln
                20                   25                   30

Leu Asp Gly Asp Gly Asn Ile Leu Gln Tyr Asn Ala Ala Glu Gly Asp
            35                   40                   45

Ile Thr Gly Arg Asp Pro Lys Gln Val Ile Gly Lys Asn Phe Phe Lys
        50                   55                   60

Asp Val Ala Pro Cys Thr Asp Ser Pro Glu Phe Tyr Gly Lys Phe Lys
65                   70                   75                   80

Glu Gly Val Ala Ser Gly Asn Leu Asn Thr Met Phe Glu Tyr Thr Phe
                85                   90                   95

Asp Tyr Gln Met Thr Pro Thr Lys Val Lys Val His Met Lys Lys Ala
                100                  105                  110

Leu Ser Gly Asp Ser Tyr Trp Val Phe Val Lys Arg Val
            115                  120                  125

<210> SEQ ID NO 50
<211> LENGTH: 125
<212> TYPE: PRT
<213> ORGANISM: Halomonas boliviensis LC1

<400> SEQUENCE: 50

Met Glu Thr Val Arg Phe Gly Gly Asp Asp Ile Glu Asn Ser Leu Ala
1               5                    10                   15

Lys Met Asp Asp Lys Lys Leu Asp Glu Leu Ala Phe Gly Ala Ile Gln
                20                   25                   30

Leu Asp Ala Asn Gly Lys Ile Ile Gln Tyr Asn Ala Ala Glu Gly Gly
            35                   40                   45

Ile Thr Gly Arg Asp Pro Lys Ser Val Ile Gly Lys Asn Phe Phe Thr
        50                   55                   60

Glu Val Ala Pro Cys Thr Gln Ser Lys Glu Phe Gln Gly Arg Phe Lys
65                   70                   75                   80

Glu Gly Val Ser Ser Gly Glu Leu Asn Thr Met Phe Glu Tyr Val Phe
```

85                  90                  95

Asp Tyr Gln Met Thr Pro Thr Lys Val Lys Val His Met Lys Lys Ala
                100                 105                 110

Ile Ser Gly Asp Thr Tyr Trp Ile Phe Val Lys Arg Leu
        115                 120                 125

<210> SEQ ID NO 51
<211> LENGTH: 125
<212> TYPE: PRT
<213> ORGANISM: Halomonas sp. GFAJ-1

<400> SEQUENCE: 51

Met Glu Thr Val Arg Phe Gly Gly Asp Asp Ile Glu Asn Ala Leu Ala
1               5                   10                  15

Asn Met Asp Asp Lys Lys Leu Asp Thr Leu Ala Phe Gly Ala Ile Gln
                20                  25                  30

Leu Asp Ala Asn Gly Lys Ile Ile Gln Tyr Asn Ala Ala Glu Gly Gly
            35                  40                  45

Ile Thr Gly Arg Asp Pro Lys Ser Val Ile Gly Lys Asn Phe Phe Thr
    50                  55                  60

Asp Val Ala Pro Cys Thr Gln Ser Lys Glu Phe Gln Gly Arg Phe Lys
65                  70                  75                  80

Glu Gly Val Lys Asn Gly Asp Leu Asn Thr Met Phe Glu Tyr Val Phe
                85                  90                  95

Asp Tyr Gln Met Thr Pro Thr Lys Val Lys Val His Met Lys Lys Ala
                100                 105                 110

Leu Ser Gly Asp Thr Phe Trp Ile Phe Val Lys Arg Leu
        115                 120                 125

<210> SEQ ID NO 52
<211> LENGTH: 125
<212> TYPE: PRT
<213> ORGANISM: Rheinheimera sp. A13L

<400> SEQUENCE: 52

Leu Glu Thr Val Arg Phe Gly Gly Asp Asp Ile Glu Asn Ser Leu Ala
1               5                   10                  15

Lys Met Asp Asp Lys Ala Leu Asp Lys Leu Ala Phe Gly Ala Ile Gln
                20                  25                  30

Leu Asp Gly Asn Gly Lys Ile Ile His Tyr Asn Ala Ala Glu Gly Thr
            35                  40                  45

Ile Thr Gly Arg Asp Pro Lys Thr Val Ile Gly Lys Asn Phe Phe Thr
    50                  55                  60

Asp Val Ala Pro Cys Thr Gln Ser Lys Glu Phe Gln Gly Arg Phe Lys
65                  70                  75                  80

Glu Gly Val Gln Lys Gly Asp Leu Asn Thr Met Phe Glu Tyr Val Phe
                85                  90                  95

Asp Tyr Gln Met Lys Pro Thr Lys Val Lys Val His Met Lys Lys Ala
                100                 105                 110

Met Thr Gly Asp Ser Phe Trp Ile Phe Val Lys Arg Leu
        115                 120                 125

<210> SEQ ID NO 53
<211> LENGTH: 125
<212> TYPE: PRT
<213> ORGANISM: Idiomarina loihiensis

<400> SEQUENCE: 53

```
Met Glu Ile Val Gln Phe Gly Ser Asp Asp Ile Glu Asn Thr Leu Ser
1               5                   10                  15

Lys Met Ser Asp Lys Leu Asn Asp Ile Ala Phe Gly Ala Ile Gln
            20                  25                  30

Leu Asp Ala Ser Gly Lys Ile Ile Gln Tyr Asn Ala Ala Glu Gly Asp
                35                  40                  45

Ile Thr Gly Arg Asp Pro Gly Ala Val Val Gly Lys Asn Phe Phe Asn
            50                  55                  60

Glu Val Ala Pro Cys Thr Asn Ser Pro Glu Phe Lys Gly Arg Phe Asp
65                  70                  75                  80

Glu Gly Val Lys Asn Gly Asn Leu Asn Thr Met Phe Glu Tyr Val Phe
                85                  90                  95

Asp Tyr Glu Met Gln Pro Thr Lys Val Lys Val His Met Lys Lys Ala
                100                 105                 110

Leu Thr Gly Asp Thr Tyr Trp Val Phe Val Lys Arg Leu
            115                 120                 125
```

<210> SEQ ID NO 54
<211> LENGTH: 125
<212> TYPE: PRT
<213> ORGANISM: Thiorhodospira sibirica ATCC 700588

<400> SEQUENCE: 54

```
Met Glu Leu Leu Ser Phe Gly Ala Asp Asn Ile Glu Asn Ser Leu Ala
1               5                   10                  15

Lys Met Ser Lys Gly Asp Leu Asn Lys Leu Ala Phe Gly Ala Ile Gln
            20                  25                  30

Leu Asn Ala Gln Gly Lys Ile Leu Gln Tyr Asn Ala Ala Glu Gly Asp
                35                  40                  45

Ile Thr Gly Arg Lys Pro Thr Glu Val Ile Gly Lys Asn Phe Phe Leu
            50                  55                  60

Glu Val Ala Pro Cys Thr Asn Arg Thr Glu Phe Lys Gly Arg Phe Asp
65                  70                  75                  80

Gln Gly Ile Lys Ser Gly Asn Leu Asn Thr Met Phe Glu Tyr Thr Phe
                85                  90                  95

Asp Tyr Glu Met Lys Pro Thr Lys Val Lys Val His Met Lys Lys Ala
                100                 105                 110

Leu Val Asp Asp Thr Tyr Trp Val Phe Val Lys Arg Val
            115                 120                 125
```

<210> SEQ ID NO 55
<211> LENGTH: 125
<212> TYPE: PRT
<213> ORGANISM: Rhodothalassium salexigens

<400> SEQUENCE: 55

```
Met Glu Met Ile Lys Phe Gly Gln Asp Ile Glu Asn Ala Met Ala
1               5                   10                  15

Asp Met Gly Asp Ala Gln Ile Asp Asp Leu Ala Phe Gly Ala Ile Gln
            20                  25                  30

Leu Asp Glu Thr Gly Thr Ile Leu Ala Tyr Asn Ala Ala Glu Gly Glu
                35                  40                  45

Leu Thr Gly Arg Ser Pro Gln Asp Val Ile Gly Lys Asn Phe Phe Lys
            50                  55                  60

Asp Ile Ala Pro Cys Thr Asp Thr Glu Glu Phe Gly Gly Arg Phe Arg
65                  70                  75                  80
```

```
Glu Gly Val Ala Asn Gly Asp Leu Asn Ala Met Phe Glu Tyr Val Phe
                85                  90                  95

Asp Tyr Gln Met Gln Pro Thr Lys Val Lys Val His Met Lys Arg Ala
            100                 105                 110

Ile Thr Gly Asp Ser Tyr Trp Ile Phe Val Lys Arg Val
        115                 120                 125

<210> SEQ ID NO 56
<211> LENGTH: 124
<212> TYPE: PRT
<213> ORGANISM: Roseomonas cervicalis ATCC 49957

<400> SEQUENCE: 56

Met Glu Leu Leu Lys Phe Gly Thr Asp Asp Ile Asp Asn Leu Val Ala
1               5                   10                  15

Arg Asp Pro Ser Arg Leu Asp Arg Leu Pro Phe Gly Ala Val Leu Leu
                20                  25                  30

Asp Arg Thr Gly Arg Val Thr Lys Tyr Asn Ala Gly Glu Val Ala Ile
            35                  40                  45

Ser Gly Arg Thr Ala Asp Gln Val Leu Gly Lys Asn Phe Phe Asn Asp
        50                  55                  60

Ile Ala Pro Cys Thr Lys Gly His Gln Phe Met Gly Arg Phe Asn Gln
65                  70                  75                  80

Ala Leu Ala Gln Gly Ser Ile Asn Thr Met Phe Glu Tyr Ala Phe Asp
                85                  90                  95

Tyr Lys Met Lys Pro Ala Lys Val Arg Val His Met Lys Ser Val Ser
            100                 105                 110

Ile Asp Gln Gly Ile Trp Val Phe Ile Lys Arg Leu
        115                 120

<210> SEQ ID NO 57
<211> LENGTH: 124
<212> TYPE: PRT
<213> ORGANISM: Rhodobacter sphaeroides

<400> SEQUENCE: 57

Met Glu Ile Ile Pro Phe Gly Ser Ala Asp Leu Asp Asn Ile Leu Ala
1               5                   10                  15

Arg Glu Pro Gln Arg Ala Glu Tyr Leu Pro Phe Gly Ala Val Leu Leu
                20                  25                  30

Asp Arg Thr Gly Thr Ile Leu Lys Tyr Asn Arg Ala Glu Gly Gly Ile
            35                  40                  45

Ala Asn Arg Asn Pro Ala Asp Val Ile Gly Lys Asn Phe Phe Asn Glu
        50                  55                  60

Ile Ala Pro Cys Ala Lys Gly Lys Arg Phe His Gly Glu Phe Leu Arg
65                  70                  75                  80

Phe His Gln Thr Gly Gln Val Asn Val Met Phe Asp Tyr Lys Phe Ala
                85                  90                  95

Tyr Lys Gly Ala Asn Val Gly Val Lys Ile His Met Lys Ser Gln Pro
            100                 105                 110

Asp Gly Gln Ser Cys Trp Leu Phe Val Lys Arg Val
        115                 120

<210> SEQ ID NO 58
<211> LENGTH: 112
<212> TYPE: PRT
<213> ORGANISM: Leptospira wolbachii
```

<400> SEQUENCE: 58

Ser Asn Lys Leu Gly Thr Leu Thr Gln Ala Glu Ala Asp Ala Ala Ala
1               5                   10                  15

Phe Gly Ile Val Lys Val Asp Gly Asn Gly Lys Ile Leu Leu Tyr Asn
            20                  25                  30

Lys Tyr Glu Ser Glu Leu Ser Asn Leu Pro Asn Asp Thr Val Ile Gly
        35                  40                  45

Lys Asn Phe Phe Thr Glu Val Ala Ile Cys Ala Asn Asn Arg Ile Phe
    50                  55                  60

Tyr Gly Lys Phe Lys Glu Gly Met Val Ser Lys Asn Leu Asp Thr Ala
65                  70                  75                  80

Phe Asn Tyr Val Phe Thr Tyr Arg Met Lys Pro Thr Asn Val Leu Ile
                85                  90                  95

His Leu Tyr Tyr Asp Lys Thr Ser Asp Ser Asn Trp Ile Phe Val Lys
            100                 105                 110

<210> SEQ ID NO 59
<211> LENGTH: 123
<212> TYPE: PRT
<213> ORGANISM: Rhodobacter capsulatus

<400> SEQUENCE: 59

Met Glu Ile Ile Pro Phe Gly Thr Asn Asp Ile Asp Asn Ile Leu Ala
1               5                   10                  15

Arg Glu Pro Ala Arg Ala Glu Ser Leu Pro Phe Gly Ala Val Leu Leu
            20                  25                  30

Asp Arg Met Gly Arg Ile Ala Lys Tyr Asn Lys Ala Glu Gly Leu Ile
        35                  40                  45

Ala Gly Arg Asp Pro Ser Thr Val Ile Gly Arg Asp Phe Phe Asn Glu
    50                  55                  60

Ile Ala Pro Cys Ala Lys Gly Lys Arg Phe His Gly Glu Phe Leu Lys
65                  70                  75                  80

Phe Asn Arg Thr Gly Gln Ala Asn Val Met Leu Asp Tyr Lys Phe Asn
                85                  90                  95

Tyr Lys Gly Ala Glu Val Ala Val Lys Ile His Leu Lys Ser Gln Pro
            100                 105                 110

Asp Gly Gln Phe Cys Trp Leu Phe Val Lys Arg
        115                 120

<210> SEQ ID NO 60
<211> LENGTH: 117
<212> TYPE: PRT
<213> ORGANISM: Rhodospirillum centenum

<400> SEQUENCE: 60

Thr Glu Gln Ile Arg Gly Thr Ile Asp Gly Met Gly Thr Ala Glu Phe
1               5                   10                  15

Asp Ala Leu Pro Val Gly Ala Ile Gln Val Asp Gly Ser Gly Val Ile
            20                  25                  30

His Arg Tyr Asn Arg Thr Glu Ser Arg Leu Ser Gly Arg Ile Pro Glu
        35                  40                  45

Arg Val Ile Gly Arg Asn Phe Phe Thr Glu Val Ala Pro Cys Thr Asn
    50                  55                  60

Ile Pro Ala Phe Ser Gly Arg Phe Met Asp Gly Val Thr Ser Gly Thr
65                  70                  75                  80

Leu Asp Ala Arg Phe Asp Phe Val Phe Asp Phe Gln Met Ala Pro Val
                85                  90                  95

Arg Val Gln Ile Arg Met Gln Asn Ala Gly Val Pro Asp Arg Tyr Trp
                100                 105                 110

Ile Phe Val Arg Lys
        115

<210> SEQ ID NO 61
<211> LENGTH: 112
<212> TYPE: PRT
<213> ORGANISM: Leptospira vanthielii

<400> SEQUENCE: 61

Ser Asn Lys Leu Gly Thr Leu Thr Gln Ala Glu Ala Asp Ala Ala Ala
1               5                   10                  15

Phe Gly Ile Val Lys Val Asp Gly Asn Gly Lys Ile Leu Leu Tyr Asn
            20                  25                  30

Lys Tyr Glu Ser Glu Leu Ser Asn Leu Pro Asn Asp Thr Val Ile Gly
        35                  40                  45

Lys Asn Phe Phe Thr Glu Val Ala Ile Cys Ala Asn Asn Arg Ile Phe
    50                  55                  60

Tyr Gly Lys Phe Lys Glu Gly Met Val Thr Lys Asn Leu Asp Thr Ala
65                  70                  75                  80

Phe Asn Tyr Val Phe Thr Tyr Arg Met Lys Pro Thr Asn Val Leu Ile
                85                  90                  95

His Leu Tyr Tyr Asp Lys Thr Ser Asp Thr Asn Trp Ile Phe Val Lys
                100                 105                 110

<210> SEQ ID NO 62
<211> LENGTH: 118
<212> TYPE: PRT
<213> ORGANISM: Leptospira terpstrae

<400> SEQUENCE: 62

Phe Ile Asp Pro Asn Ile Leu Gly Lys Leu Gly Thr Leu Thr Gln Ala
1               5                   10                  15

Glu Ala Asp Ala Ala Ala Phe Gly Val Val Lys Val Asp Gly Asn Gly
            20                  25                  30

Lys Ile Leu Leu Tyr Asn Lys Tyr Glu Ser Glu Leu Ala Asn Val Pro
        35                  40                  45

Ile Gln Thr Ala Val Gly Lys Asn Phe Phe Thr Glu Val Ala Ile Cys
    50                  55                  60

Thr Asn Asn Arg Ile Phe Tyr Gly Arg Phe Lys Glu Gly Met Leu Thr
65                  70                  75                  80

Gly Asp Leu Asp Ile Ala Phe Asn Tyr Val Phe Thr Tyr Lys Met Lys
                85                  90                  95

Pro Thr Asn Val Val Ile His Leu Tyr His Asp Lys Thr Ser Asp Thr
                100                 105                 110

Asn Trp Ile Phe Val Lys
        115

<210> SEQ ID NO 63
<211> LENGTH: 118
<212> TYPE: PRT
<213> ORGANISM: Leptospira biflexa serovar Patoc strain 'Patoc 1
      (Paris)'

<400> SEQUENCE: 63

Phe Ile Asp Pro Asn Ile Leu Gly Lys Leu Gly Thr Leu Ala Gln Ala
1               5                   10                  15

Glu Ala Asp Gly Tyr Pro Phe Gly Ile Val Lys Val Asp Glu Ser Gly
                20                  25                  30

Lys Ile Leu Leu Tyr Asn Lys Tyr Glu Ser Glu Leu Ala Asn Val Pro
            35                  40                  45

Ile Gln Thr Ala Val Gly Lys Asn Phe Phe Thr Glu Val Ala Ile Cys
        50                  55                  60

Thr Asn Asn Arg Ile Phe Tyr Gly Arg Phe Lys Glu Gly Met Ile Ser
65                  70                  75                  80

Gly Asp Leu Asp Ile Ala Phe Asn Tyr Val Phe Thr Tyr Lys Met Lys
                85                  90                  95

Pro Thr Asn Val Val Ile His Leu Tyr His Asp Lys Gly Thr Asn Ser
                100                 105                 110

Asn Trp Ile Phe Val Lys
            115

<210> SEQ ID NO 64
<211> LENGTH: 118
<212> TYPE: PRT
<213> ORGANISM: Leptospira meyeri

<400> SEQUENCE: 64

Phe Ile Asp Gln Asn Ile Ile Gly Lys Leu Gly Thr Leu Thr Gln Ser
1               5                   10                  15

Glu Ala Asp Ala Ala Ser Phe Gly Ile Val Lys Val Asp Gly Ser Gly
                20                  25                  30

Lys Ile Leu Leu Tyr Asn Lys Tyr Glu Ser Glu Leu Ala Asn Val Pro
            35                  40                  45

Ile Gln Thr Ala Val Gly Lys Asn Phe Phe Thr Glu Val Ala Ile Cys
        50                  55                  60

Thr Asn Asn Arg Ile Phe Tyr Gly Arg Phe Lys Glu Gly Met Val Ser
65                  70                  75                  80

Gly Asp Leu Asp Ile Ala Phe Asn Tyr Val Phe Thr Tyr Lys Met Lys
                85                  90                  95

Pro Thr Asn Val Val Ile His Leu Tyr His Asp Asn Pro Ser Asn Thr
                100                 105                 110

Asn Trp Ile Phe Val Lys
            115

<210> SEQ ID NO 65
<211> LENGTH: 118
<212> TYPE: PRT
<213> ORGANISM: Leptospira yanagawae

<400> SEQUENCE: 65

Phe Ile Asp Pro Asn Ile Leu Gly Lys Leu Gly Thr Leu Gly Gln Ala
1               5                   10                  15

Asp Ala Asp Ser Tyr Pro Phe Gly Ile Val Lys Val Asp Glu Ser Gly
                20                  25                  30

Lys Ile Leu Leu Tyr Asn Lys Tyr Glu Ser Glu Leu Ala Asn Val Pro
            35                  40                  45

Ile Gln Thr Ala Val Gly Lys Asn Phe Phe Thr Glu Val Ala Ile Cys
        50                  55                  60

Thr Asn Asn Arg Ile Phe Tyr Gly Arg Phe Lys Glu Gly Met Ile Ser
65                  70                  75                  80

Gly Asp Leu Asp Ile Ala Phe Asn Tyr Val Phe Thr Tyr Lys Met Lys
                85                  90                  95

Pro Thr Asn Val Val Ile His Leu Tyr His Asp Lys Gly Thr Asn Thr
            100                 105                 110

Asn Trp Ile Phe Val Lys
            115

<210> SEQ ID NO 66
<211> LENGTH: 120
<212> TYPE: PRT
<213> ORGANISM: Salinibacter ruber DSM 13855

<400> SEQUENCE: 66

Leu Ala Phe Asp Asp Glu Gly Val Gly Glu Glu Leu Arg His Val Asp
1               5                   10                  15

Glu Asp Glu Leu Asn Ala Ala Pro Phe Gly Ile Gln Ile Asp Asp
            20                  25                  30

Ala Gly Val Val Gln Phe Tyr Asn Arg Tyr Glu Ser Asn Leu Ser Gly
            35                  40                  45

Ile Asp Pro Ala Asp Ala Val Gly Ala Asn Phe Phe Thr Glu Leu Ala
50                  55                  60

Pro Cys Ser Asn Asn Pro Leu Phe Phe Gly Arg Phe Lys Asp Gly Val
65                  70                  75                  80

Arg Glu Gly Gly Leu Asp Glu Tyr Phe Thr Tyr Thr Phe Thr Tyr Gln
                85                  90                  95

Met Arg Pro Thr Leu Val Asp Val Arg Leu Tyr Arg Asp Glu Ala Glu
            100                 105                 110

Asn Asn Trp Ile Leu Ile Gln Lys
            115                 120

<210> SEQ ID NO 67
<211> LENGTH: 107
<212> TYPE: PRT
<213> ORGANISM: Burkholderia phytofirmans PsJN

<400> SEQUENCE: 67

Leu Ala Met Leu Asp Ala Asp Arg Leu Asp Gly Val Pro Phe Gly Val
1               5                   10                  15

Ile Gly Phe Thr Ser Asp Ala Leu Val Thr Val Tyr Asn Ala Thr Glu
            20                  25                  30

Ser Lys Asn Ala Gly Leu Arg Pro Lys Met Val Leu Gly Lys His Phe
            35                  40                  45

Phe Gly Glu Val Ala Pro Cys Met Asn Asn Phe Met Val Ala Gln Arg
50                  55                  60

Phe Glu Asp Glu Asp Val Leu Asp Asp Ile Val Pro Tyr Val Leu Thr
65                  70                  75                  80

Leu Arg Met Arg Pro Thr Pro Val Arg Leu Arg Leu Lys Ala Thr
                85                  90                  95

Asp Cys Ala Thr Arg Phe Val Leu Ile Glu Arg
            100                 105

<210> SEQ ID NO 68
<211> LENGTH: 123
<212> TYPE: PRT
<213> ORGANISM: Phaeospirillum fulvum

<400> SEQUENCE: 68

Met Thr Val Phe Ala Phe Asp Gln Ser Asp Pro Glu Asn Pro Leu Gly

```
  1               5                  10                 15
Gln Leu Lys Asp Glu Asp Leu Arg Lys Ile Pro Tyr Gly Ala Ala Glu
                20                 25                 30

Leu Asn Ala Glu Gly Arg Val Val Ser Tyr Asn Asp Thr Glu Pro Glu
                35                 40                 45

Asp Asn Glu Ser Gly Arg Thr Ser Pro Val Gly Arg Asp Phe Phe Gly
                50                 55                 60

Asp Val Val Arg Trp Ala Gly Ser Ser Ile Ile Ala Ala Glu Phe Arg
 65                 70                 75                 80

Lys Gly Val Thr Ser Gly Ala Leu Asn Val Val Phe Asp Cys Ala Ser
                85                 90                 95

Ala Arg Leu Pro Tyr Lys Val Arg Val His Phe Lys Val Ser Pro Ile
                100                105                110

Leu Gly Thr Tyr Trp Val Phe Ile Lys Arg Leu
                115                120
```

<210> SEQ ID NO 69
<211> LENGTH: 121
<212> TYPE: PRT
<213> ORGANISM: Acidithiobacillus thiooxidans

<400> SEQUENCE: 69

```
Phe Val Ala Asp Ala Ile Leu Asn Asn Pro Asp Gln Ile Asn Ala Gln
 1               5                  10                 15

Ile Ala Asp Arg Gln Ser Phe Gly Ile Ile Ala Leu Asp Ser His Ala
                20                 25                 30

Gln Val Lys Ile Phe Asn Ala Ala Glu Ala Arg Leu Ser Gly Leu Ser
                35                 40                 45

Val Thr Glu Val Leu Gly Arg Asn Phe Phe Thr Glu Val Ala Pro Cys
                50                 55                 60

Thr Ala Ser Arg Leu Phe Arg Gly Arg Phe Gln Gly Ile Gln Glu
 65                 70                 75                 80

Gly Ser Leu Asp Ala His Phe Tyr Tyr Thr Phe Thr Tyr Arg Ile Arg
                85                 90                 95

Pro Ile Ser Ala His Val His Met Phe Tyr Asp Met Arg Lys Ser Pro
                100                105                110

Leu Phe Phe Ile Phe Ile Asp Arg Ile
                115                120
```

<210> SEQ ID NO 70
<211> LENGTH: 126
<212> TYPE: PRT
<213> ORGANISM: Acidithiobacillus caldus SM-1

<400> SEQUENCE: 70

```
Met Pro Arg Lys Gly Phe Val Pro Gln Ala Ile Ser Glu His Leu Asp
 1               5                  10                 15

Ser Leu Asn Gln Ala Leu Ala Asp Gln Gln Ser Phe Gly Ile Ile Gly
                20                 25                 30

Leu Asp Val Gln Ala Ile Val Arg Ile Phe Asn Lys Ala Glu Glu Arg
                35                 40                 45

Leu Ser Gly Leu Pro Ala Ser Glu Val Leu Asn His Ser Phe Phe Asp
                50                 55                 60

Asp Val Ala Pro Cys Thr Ala Ser Arg Leu Phe Arg Gly Arg Phe Leu
 65                 70                 75                 80

Ala Gly Leu Glu Arg Gly Ser Leu Asp Glu His Phe Phe Tyr Thr Phe
```

```
                    85                  90                  95

Thr Tyr Arg Ile Arg Pro Val Ser Ala His Ile His Met Leu Tyr Arg
                100                 105                 110

Pro Ala Gln Ser Pro Leu Val Phe Leu Phe Val Asp Arg Val
            115                 120                 125

<210> SEQ ID NO 71
<211> LENGTH: 104
<212> TYPE: PRT
<213> ORGANISM: gammaproteobacterium NOR5-3

<400> SEQUENCE: 71

Thr Gln His Glu Leu Asp Asn Cys Asp Pro Asp Ala Leu Asp Phe Gly
1               5                   10                  15

Val Ile Arg Met Asp Arg Ser Gly Val Val Phe Tyr Asn Val Ala
            20                  25                  30

Glu Thr Arg Ile Ser Gly Leu Ser Lys Ser Gln Val Glu Gly Arg Ala
            35                  40                  45

Phe Phe Ser Glu Ile Gly Ile Cys Met His Asn Phe Met Val Gly His
50                  55                  60

Lys Phe Glu Gln Pro Gly Asp Leu Asp Glu Leu Val Asp Tyr Val Leu
65                  70                  75                  80

Thr Leu Arg Met Asp Pro Thr Pro Val Thr Leu Arg Leu Leu Arg Gln
                85                  90                  95

Gly Asp Glu Lys Tyr Gln Tyr Leu
                100

<210> SEQ ID NO 72
<211> LENGTH: 125
<212> TYPE: PRT
<213> ORGANISM: Methylotenera versatilis 301

<400> SEQUENCE: 72

Met Asn Gln Ile Thr Phe Asp Met Leu Ser Leu Gly Gln Thr Leu Asp
1               5                   10                  15

Lys Leu Thr Asn Asp Gln Leu Asn Ser Leu Asp Phe Gly Val Ile Gly
            20                  25                  30

Phe Asp Asn Glu Gly Met Val Lys Val Tyr Asn Ala Tyr Glu Ser Lys
            35                  40                  45

Val Ala Gly Leu Ser Leu Glu Ser Val Ile Asp Ser Asp Leu Phe Asn
50                  55                  60

Ser Val Ala Pro Cys Met Asn Asn Phe Met Val Ala Gln Lys Phe Glu
65                  70                  75                  80

Asp Ala Val Asp Thr Ser Ser Glu Leu Asp Glu Ile Met Asp Tyr Val
                85                  90                  95

Leu Thr Leu Lys Met Lys Pro Thr Arg Val Lys Leu Arg Leu Leu Ser
                100                 105                 110

Ser Pro Gln Phe Ser Tyr Ser Tyr Val Val Ile Leu Arg
            115                 120                 125

<210> SEQ ID NO 73
<211> LENGTH: 122
<212> TYPE: PRT
<213> ORGANISM: Leptothrix cholodnii SP-6

<400> SEQUENCE: 73

Leu Val Phe Asp Gln Pro Asp Leu Ala Ala Cys Ile Gly Thr Leu Ser
1               5                   10                  15
```

-continued

Glu Ala Gln Leu Asp Gly Leu Gly Phe Gly Val Ile Gly Phe Asp Ala
            20                  25                  30

Gln Gly Val Val Arg Val Tyr Asn Ala Phe Glu Ser Lys Tyr Ala Gly
        35                  40                  45

Leu Ser Pro Gln Arg Val Leu Gly His Pro Leu Phe Thr Val Val Ala
    50                  55                  60

Pro Cys Met Asn Asn Phe Met Val Ala Gln Arg Phe Glu Asp Ala Ala
65                  70                  75                  80

Ala Ser Ala Ala Ser Leu Asp Ala Thr Ile Asp Tyr Val Leu Thr Leu
                85                  90                  95

Arg Met Arg Pro Val Lys Val Lys Leu Arg Leu Ala Ala Pro Ala
            100                 105                 110

Thr Ala Leu Arg Tyr Val Leu Val Gln Arg
        115                 120

<210> SEQ ID NO 74
<211> LENGTH: 119
<212> TYPE: PRT
<213> ORGANISM: Caenispirillum salinarum

<400> SEQUENCE: 74

Met Thr Phe Asp Asp Pro Asp Met Leu Arg Trp Leu Glu Ser Ala Arg
1               5                   10                  15

Ala Ala Asp Leu Asp Ala Leu Asp Phe Gly Val Ile Gly Ile Gly Pro
            20                  25                  30

Asp Gly Ala Val Ser His Tyr Asn Ala Trp Glu Val Gly Ala Ala Gly
        35                  40                  45

Ile Ser Arg Asp Trp Ala Met Gly Arg Asp Phe Phe Asn Glu Val Gly
    50                  55                  60

Leu Cys Met Asn Asn Phe Leu Val Ala Gln Arg Phe Glu Asp Glu Pro
65                  70                  75                  80

Thr Leu Asp Ala Phe Val Asp Tyr Val Leu Thr Phe Arg Met Lys Pro
                85                  90                  95

Thr Arg Val Thr Leu Arg Leu Leu Gln His Pro Asp Ser Pro Thr Arg
            100                 105                 110

Trp Ile Leu Ile Arg Arg Val
        115

<210> SEQ ID NO 75
<211> LENGTH: 125
<212> TYPE: PRT
<213> ORGANISM: Stigmatella aurantiaca DW4/3-1

<400> SEQUENCE: 75

Met Arg His Gly Ile Leu Glu Ala Glu Ser Leu Thr Glu Asp Arg Leu
1               5                   10                  15

Gly Gln Leu Ser Pro Glu Glu Phe Asp Ala Leu Pro Phe Gly Ala Ile
            20                  25                  30

Lys Leu Asp Ala Glu Gly Arg Val Leu Ile Tyr Asn Ala Ala Glu Ser
        35                  40                  45

Ala Phe Ser Arg Arg Lys Pro Val Ser Val Leu Gly Arg Arg Phe Phe
    50                  55                  60

Glu Glu Val Ala Pro Cys Thr Asn Val Ala Ser Phe Arg Gly Arg Phe
65                  70                  75                  80

Asp Thr Leu Val Glu Arg Gly His Gly Thr Glu Ser Phe Asp Phe Gln
                85                  90                  95

```
Phe Arg Phe Arg Trp Gly Thr Arg Asn Val Arg Ile Arg Leu Met Val
                100                 105                 110

Leu Gly Asp Gly Ser Arg Trp Val Phe Val Thr Ala Val
        115                 120                 125

<210> SEQ ID NO 76
<211> LENGTH: 122
<212> TYPE: PRT
<213> ORGANISM: Massilia timonae

<400> SEQUENCE: 76

Leu Ala Phe Asp Ala Pro Asp Leu Ala Ala Arg Leu Asp Gln Cys Thr
1               5                   10                  15

Pro Glu Gln Leu Asp Ala Leu Asp Phe Gly Val Ile Gly Phe Gly Ala
            20                  25                  30

Asp Thr Asn Val Thr Leu Tyr Asn Ala Phe Glu Ser Gln Ala Ala Gly
        35                  40                  45

Leu Ser Pro Gln Arg Val Leu Gly Gln Pro Leu Phe Thr Asn Val Ala
    50                  55                  60

Pro Cys Met Asn Asn Phe Met Val Ala Gln Arg Phe Glu Asp Ala Gln
65                  70                  75                  80

Glu Asp Asn Ser Val Leu Asp Ala Thr Ile Asp Tyr Val Leu Thr Leu
                85                  90                  95

Arg Met Arg Pro Val Lys Val Ala Arg Leu Leu Ser Asn Pro Gly
            100                 105                 110

Gly Ser Arg Arg Tyr Val Leu Val Gln Arg
        115                 120

<210> SEQ ID NO 77
<211> LENGTH: 124
<212> TYPE: PRT
<213> ORGANISM: Methyloversatilis universalis FAM5

<400> SEQUENCE: 77

Gln Thr Val Ala Phe Ser Glu Ala Arg Met Leu Glu Phe Leu Glu Ser
1               5                   10                  15

Ala Ser Asp Glu Asp Leu Asp Arg Leu Asp Phe Gly Val Ile Gly Ile
            20                  25                  30

Asp Ala Gly Thr Asn Val Lys Arg Tyr Asn Arg Phe Glu Ser Ala Ala
        35                  40                  45

Ala Gly Leu Ser Lys Asp Arg Val Ile Gly Tyr Ala Leu Phe Thr Val
    50                  55                  60

Val Ala Pro Cys Met Asn Asn Phe Met Val Ala Gln Arg Phe Glu Asp
65                  70                  75                  80

Ala Gln Glu Gln Gly Ser Ala Leu Asp Asp Thr Ile Asp Tyr Val Leu
                85                  90                  95

Thr Leu Arg Met Arg Pro Val Lys Val Lys Leu Arg Leu Leu Ala Ala
            100                 105                 110

Pro Asp Arg Ala Leu Arg Tyr Val Leu Val Gln Arg
        115                 120

<210> SEQ ID NO 78
<211> LENGTH: 117
<212> TYPE: PRT
<213> ORGANISM: Spirosoma linguale DSM 74

<400> SEQUENCE: 78
```

```
Val His Phe Ser Asp Leu Asn Leu Leu Asp Trp Leu Glu Lys Gln Thr
1               5                   10                  15

Asn Glu Gln Leu Glu Asp Ala Pro Phe Gly Val Val Arg Met Ser Arg
            20                  25                  30

Asp Gly Ile Val Val Ala Tyr Cys Lys Ser Glu Ser His Ile Thr Gly
            35                  40                  45

Ile Ser Lys Glu Tyr Ala Val Gly Lys Tyr Tyr Phe Thr Gln Ile Ala
    50                  55                  60

Pro Cys Ala Asn Asn Gln Met Val Ala Ala Lys Tyr Ala Gln Pro Thr
65                  70                  75                  80

Leu Asp Glu Glu Leu Asp Tyr Ile Leu Thr Tyr Val Ser Glu Pro Thr
                85                  90                  95

Lys Val Arg Leu Arg Leu Leu Lys Ser Pro Glu Ser Arg Tyr Gln Tyr
                100                 105                 110

Phe Leu Val Asn Arg
            115

<210> SEQ ID NO 79
<211> LENGTH: 123
<212> TYPE: PRT
<213> ORGANISM: Rhodopseudomonas palustris BisB5

<400> SEQUENCE: 79

Met Asn Thr Val Asp Phe His Asp Ser Asp Leu Ala Arg Thr Ile Glu
1               5                   10                  15

Gln Leu Ala Pro Glu Gln Ile Asp Ala Leu Pro Phe Gly Val Ile Lys
            20                  25                  30

Leu Asp Gly Asn Gly Ile Val Thr Val Phe Asn Arg Thr Glu Ala Ile
            35                  40                  45

Glu Ser Gly Tyr Lys Ser Arg Pro Ala Leu Gly Leu Asp Phe Phe Leu
    50                  55                  60

Gln Val Ala Pro Cys Met Gly Gln Pro Glu Phe Arg Gly Arg Ile Glu
65                  70                  75                  80

Gln Ala Arg Gln Leu Gly Arg Val Asp Ile Glu Leu Gly Trp Val Gly
                85                  90                  95

Asp Phe Ser Asp Ile Asn Arg Ser Leu Gln Val Arg Ile Gln Ser Ala
                100                 105                 110

Ser Asp Gly Ser Leu Trp Ile Phe Asn Leu Arg
                115                 120

<210> SEQ ID NO 80
<211> LENGTH: 110
<212> TYPE: PRT
<213> ORGANISM: Sorangium cellulosum 'So ce 56'

<400> SEQUENCE: 80

Leu Asp Glu Arg Gly Leu Asp Ala Gln Pro Phe Gly Ile Ile Arg Leu
1               5                   10                  15

Asp Arg Glu Gly Thr Val Leu Ser Tyr Asn Leu Tyr Glu Glu Arg Gln
            20                  25                  30

Ala Arg Arg Asn Arg Gln Asp Val Ile Gly Lys Asn Phe Phe Thr Asp
            35                  40                  45

Ile Ala Pro Cys Ser Arg Val Lys Ala Phe His Gly Arg Phe Leu Ala
    50                  55                  60

Gly Val Glu Gln Arg Glu Leu Lys Ala Thr Phe Gly Phe Val Phe His
65                  70                  75                  80
```

```
Phe Pro His Lys Thr Arg His Val Asp Val Ser Leu Phe Tyr Lys Ala
                85                  90                  95
Ala Ala Arg Gln Gln Asp Asp Ala Val Trp Val Phe Ile Arg
            100                 105                 110

<210> SEQ ID NO 81
<211> LENGTH: 120
<212> TYPE: PRT
<213> ORGANISM: Rhodomicrobium vannielii ATCC 17100

<400> SEQUENCE: 81

Val Ser Phe Ala Asp Pro Lys Leu Ala Arg Lys Leu Glu Ala Leu Ser
1               5                   10                  15

Asp Glu Glu Arg His Asp Leu Pro Phe Gly Ile Ile Lys Leu Asp Ser
            20                  25                  30

Asn Gly Val Val Ser Phe Phe Ser Arg Thr Glu Ala Arg Glu Ser Gly
        35                  40                  45

Trp Lys Lys Arg Pro Ala Leu Gly Ile Asp Phe Phe Val Gly Ile Ala
    50                  55                  60

Pro Cys Met Ala Thr Pro Glu Phe Lys Gly Arg Ile Glu Ala Ala
65                  70                  75                  80

Arg His Gly Ala Val Asp Ile Glu Leu Gly Trp Val Gly Asp Phe Asp
                85                  90                  95

Asp Pro Asn Gly Glu Met Thr Val Arg Ile Gln Ser Ala Ala Asp Gly
            100                 105                 110

Gly Ile Trp Ile Cys Leu Asp Arg
        115                 120

<210> SEQ ID NO 82
<211> LENGTH: 8
<212> TYPE: PRT
<213> ORGANISM: Artificial Sequence
<220> FEATURE:
<223> OTHER INFORMATION: Clone 2 - Region 94-101

<400> SEQUENCE: 82

Trp Leu Ile Pro Thr Leu Pro Gln
1               5

<210> SEQ ID NO 83
<211> LENGTH: 8
<212> TYPE: PRT
<213> ORGANISM: Artificial Sequence
<220> FEATURE:
<223> OTHER INFORMATION: Clone 3 - Region 94-101

<400> SEQUENCE: 83

Trp Met Ile Pro Thr Ser Arg Gly
1               5

<210> SEQ ID NO 84
<211> LENGTH: 8
<212> TYPE: PRT
<213> ORGANISM: Artificial Sequence
<220> FEATURE:
<223> OTHER INFORMATION: Clone 4 - Region 94-101

<400> SEQUENCE: 84

Trp Asp Ile Pro Thr Asn Pro Glu
1               5

<210> SEQ ID NO 85
```

```
<211> LENGTH: 8
<212> TYPE: PRT
<213> ORGANISM: Artificial Sequence
<220> FEATURE:
<223> OTHER INFORMATION: Clone 5 - Region 94-101

<400> SEQUENCE: 85

Trp Arg Ile Pro Thr Glu Cys Ala
1               5

<210> SEQ ID NO 86
<211> LENGTH: 8
<212> TYPE: PRT
<213> ORGANISM: Artificial Sequence
<220> FEATURE:
<223> OTHER INFORMATION: Clone 6 - Region 94-101

<400> SEQUENCE: 86

Trp Leu Ile Pro Thr Arg Asn Ala
1               5

<210> SEQ ID NO 87
<211> LENGTH: 8
<212> TYPE: PRT
<213> ORGANISM: Artificial Sequence
<220> FEATURE:
<223> OTHER INFORMATION: Clone 7 - Region 94-101

<400> SEQUENCE: 87

Trp Ser Ile Pro Ala Arg Ser Ala
1               5

<210> SEQ ID NO 88
<211> LENGTH: 8
<212> TYPE: PRT
<213> ORGANISM: Artificial Sequence
<220> FEATURE:
<223> OTHER INFORMATION: Clone 8 - Region 94-101

<400> SEQUENCE: 88

Trp Tyr Ile Pro Thr Gln Thr Ser
1               5

<210> SEQ ID NO 89
<211> LENGTH: 8
<212> TYPE: PRT
<213> ORGANISM: Artificial Sequence
<220> FEATURE:
<223> OTHER INFORMATION: Clone 9 - Region 94-101

<400> SEQUENCE: 89

Trp Met Ile Pro Thr Glu His Val
1               5

<210> SEQ ID NO 90
<211> LENGTH: 8
<212> TYPE: PRT
<213> ORGANISM: Artificial Sequence
<220> FEATURE:
<223> OTHER INFORMATION: Clone 10 - Region 94-101

<400> SEQUENCE: 90

Trp Ala Ile Pro Thr His Thr Gln
1               5

<210> SEQ ID NO 91
<211> LENGTH: 8
```

```
<212> TYPE: PRT
<213> ORGANISM: Artificial Sequence
<220> FEATURE:
<223> OTHER INFORMATION: Clone 11 - Region 94-101

<400> SEQUENCE: 91

Trp Ser Ile Pro Ala Gly Lys Gly
1               5

<210> SEQ ID NO 92
<211> LENGTH: 8
<212> TYPE: PRT
<213> ORGANISM: Artificial Sequence
<220> FEATURE:
<223> OTHER INFORMATION: Clone 12 - Region 94-101

<400> SEQUENCE: 92

Trp Val Ile Pro Arg Glu Asp Asn
1               5

<210> SEQ ID NO 93
<211> LENGTH: 8
<212> TYPE: PRT
<213> ORGANISM: Artificial Sequence
<220> FEATURE:
<223> OTHER INFORMATION: Clone 13 - Region 94-101

<400> SEQUENCE: 93

Trp Ser Ile Pro Gln Ile Met Ala
1               5

<210> SEQ ID NO 94
<211> LENGTH: 8
<212> TYPE: PRT
<213> ORGANISM: Artificial Sequence
<220> FEATURE:
<223> OTHER INFORMATION: Clone 14 - Region 94-101

<400> SEQUENCE: 94

Trp Leu Val Pro Arg Ile Cys Gln
1               5

<210> SEQ ID NO 95
<211> LENGTH: 8
<212> TYPE: PRT
<213> ORGANISM: Artificial Sequence
<220> FEATURE:
<223> OTHER INFORMATION: Clone 15 - Region 94-101

<400> SEQUENCE: 95

Trp Thr Ile Pro Ala Leu Arg Lys
1               5

<210> SEQ ID NO 96
<211> LENGTH: 8
<212> TYPE: PRT
<213> ORGANISM: Artificial Sequence
<220> FEATURE:
<223> OTHER INFORMATION: Clone 16 - Region 94-101

<400> SEQUENCE: 96

Trp His Ile Pro Arg Asp Pro His
1               5

<210> SEQ ID NO 97
<211> LENGTH: 8
<212> TYPE: PRT
```

```
<213> ORGANISM: Artificial Sequence
<220> FEATURE:
<223> OTHER INFORMATION: Clone 17 - Region 94-101

<400> SEQUENCE: 97

Trp Ser Ile Pro Val Ser Gly Gln
1               5

<210> SEQ ID NO 98
<211> LENGTH: 8
<212> TYPE: PRT
<213> ORGANISM: Artificial Sequence
<220> FEATURE:
<223> OTHER INFORMATION: Clone 18 - Region 94-101

<400> SEQUENCE: 98

Trp Thr Val Pro Thr Phe Ile Val
1               5

<210> SEQ ID NO 99
<211> LENGTH: 8
<212> TYPE: PRT
<213> ORGANISM: Artificial Sequence
<220> FEATURE:
<223> OTHER INFORMATION: Clone 19 - Region 94-101

<400> SEQUENCE: 99

Trp Tyr Ile Pro Ala Asn His Lys
1               5

<210> SEQ ID NO 100
<211> LENGTH: 8
<212> TYPE: PRT
<213> ORGANISM: Artificial Sequence
<220> FEATURE:
<223> OTHER INFORMATION: Clone 20 - Region 94-101

<400> SEQUENCE: 100

Trp Val Ile Pro Pro Phe Glu Ser
1               5

<210> SEQ ID NO 101
<211> LENGTH: 8
<212> TYPE: PRT
<213> ORGANISM: Artificial Sequence
<220> FEATURE:
<223> OTHER INFORMATION: Clone 21 - Region 94-101

<400> SEQUENCE: 101

Trp Val Val Pro Asn Pro Ile Ala
1               5

<210> SEQ ID NO 102
<211> LENGTH: 8
<212> TYPE: PRT
<213> ORGANISM: Artificial Sequence
<220> FEATURE:
<223> OTHER INFORMATION: Clone 22 - Region 94-101

<400> SEQUENCE: 102

Trp Gln Ile Pro Val Tyr Ala Val
1               5

<210> SEQ ID NO 103
<211> LENGTH: 8
<212> TYPE: PRT
<213> ORGANISM: Artificial Sequence
```

```
<220> FEATURE:
<223> OTHER INFORMATION: Clone 23 - Region 94-101

<400> SEQUENCE: 103

Trp Gln Ile Pro Thr Ser Ile Ile
1               5

<210> SEQ ID NO 104
<211> LENGTH: 8
<212> TYPE: PRT
<213> ORGANISM: Artificial Sequence
<220> FEATURE:
<223> OTHER INFORMATION: Clone 24 - Region 94-101

<400> SEQUENCE: 104

Trp Met Ile Pro Gly Asp Gly Asp
1               5

<210> SEQ ID NO 105
<211> LENGTH: 8
<212> TYPE: PRT
<213> ORGANISM: Artificial Sequence
<220> FEATURE:
<223> OTHER INFORMATION: Clone 25 - Region 94-101

<400> SEQUENCE: 105

Trp Asp Ile Pro His Asp Asp Ala
1               5

<210> SEQ ID NO 106
<211> LENGTH: 8
<212> TYPE: PRT
<213> ORGANISM: Artificial Sequence
<220> FEATURE:
<223> OTHER INFORMATION: Clone 26 - Region 94-101

<400> SEQUENCE: 106

Trp Ser Ile Pro Ser Val Arg His
1               5

<210> SEQ ID NO 107
<211> LENGTH: 8
<212> TYPE: PRT
<213> ORGANISM: Artificial Sequence
<220> FEATURE:
<223> OTHER INFORMATION: Clone 27 - Region 94-101

<400> SEQUENCE: 107

Trp Phe Ile Pro Lys Gly His Lys
1               5

<210> SEQ ID NO 108
<211> LENGTH: 8
<212> TYPE: PRT
<213> ORGANISM: Artificial Sequence
<220> FEATURE:
<223> OTHER INFORMATION: Clone 28 - Region 94-101

<400> SEQUENCE: 108

Trp Arg Ile Pro Lys Pro Thr Ala
1               5

<210> SEQ ID NO 109
<211> LENGTH: 8
<212> TYPE: PRT
<213> ORGANISM: Artificial Sequence
<220> FEATURE:
```

```
<223> OTHER INFORMATION: Clone 29 - Region 94-101

<400> SEQUENCE: 109

Trp Ala Val Pro Gly Val Cys Gly
1               5

<210> SEQ ID NO 110
<211> LENGTH: 8
<212> TYPE: PRT
<213> ORGANISM: Artificial Sequence
<220> FEATURE:
<223> OTHER INFORMATION: Clone 30 - Region 94-101

<400> SEQUENCE: 110

Trp Arg Ile Pro Gly Glu Met Phe
1               5

<210> SEQ ID NO 111
<211> LENGTH: 8
<212> TYPE: PRT
<213> ORGANISM: Artificial Sequence
<220> FEATURE:
<223> OTHER INFORMATION: Clone 31 - Region 94-101

<400> SEQUENCE: 111

Trp Ser Val Pro Thr Thr Arg Leu
1               5

<210> SEQ ID NO 112
<211> LENGTH: 8
<212> TYPE: PRT
<213> ORGANISM: Artificial Sequence
<220> FEATURE:
<223> OTHER INFORMATION: Clone 32 - Region 94-101

<400> SEQUENCE: 112

Trp Phe Val Pro Gly Pro Ser Val
1               5

<210> SEQ ID NO 113
<211> LENGTH: 8
<212> TYPE: PRT
<213> ORGANISM: Artificial Sequence
<220> FEATURE:
<223> OTHER INFORMATION: Clone 33 - Region 94-101

<400> SEQUENCE: 113

Trp Arg Ile Pro Arg Arg Val Val
1               5

<210> SEQ ID NO 114
<211> LENGTH: 8
<212> TYPE: PRT
<213> ORGANISM: Artificial Sequence
<220> FEATURE:
<223> OTHER INFORMATION: Clone 34 - Region 94-101

<400> SEQUENCE: 114

Trp Thr Leu Pro Ala Trp His His
1               5

<210> SEQ ID NO 115
<211> LENGTH: 8
<212> TYPE: PRT
<213> ORGANISM: Artificial Sequence
<220> FEATURE:
<223> OTHER INFORMATION: Clone 35 - Region 94-101
```

```
<400> SEQUENCE: 115

Trp Thr Ile Pro Val Leu Gly Thr
1               5

<210> SEQ ID NO 116
<211> LENGTH: 8
<212> TYPE: PRT
<213> ORGANISM: Artificial Sequence
<220> FEATURE:
<223> OTHER INFORMATION: Clone 36 - Region 94-101

<400> SEQUENCE: 116

Trp Glu Ile Pro Ile Pro Thr Asn
1               5

<210> SEQ ID NO 117
<211> LENGTH: 8
<212> TYPE: PRT
<213> ORGANISM: Artificial Sequence
<220> FEATURE:
<223> OTHER INFORMATION: Clone 37 - Region 94-101

<400> SEQUENCE: 117

Trp Val Ile Pro Asn Tyr Thr Met
1               5

<210> SEQ ID NO 118
<211> LENGTH: 8
<212> TYPE: PRT
<213> ORGANISM: Artificial Sequence
<220> FEATURE:
<223> OTHER INFORMATION: Clone 38 - Region 94-101

<400> SEQUENCE: 118

Trp Tyr Ile Pro Ala Leu His Trp
1               5

<210> SEQ ID NO 119
<211> LENGTH: 8
<212> TYPE: PRT
<213> ORGANISM: Artificial Sequence
<220> FEATURE:
<223> OTHER INFORMATION: Clone 39 - Region 94-101

<400> SEQUENCE: 119

Trp Gly Ile Pro Thr Pro Glu Glu
1               5

<210> SEQ ID NO 120
<211> LENGTH: 8
<212> TYPE: PRT
<213> ORGANISM: Artificial Sequence
<220> FEATURE:
<223> OTHER INFORMATION: Clone 40 - Region 94-101

<400> SEQUENCE: 120

Trp Glu Ile Pro Met Gly Ala His
1               5

<210> SEQ ID NO 121
<211> LENGTH: 8
<212> TYPE: PRT
<213> ORGANISM: Artificial Sequence
<220> FEATURE:
<223> OTHER INFORMATION: Clone 41 - Region 94-101
```

```
<400> SEQUENCE: 121

Trp Ser Ile Pro Pro Gly Arg Gln
1               5

<210> SEQ ID NO 122
<211> LENGTH: 8
<212> TYPE: PRT
<213> ORGANISM: Artificial Sequence
<220> FEATURE:
<223> OTHER INFORMATION: Clone 42 - Region 94-101

<400> SEQUENCE: 122

Trp Asn Leu Pro Val Lys Ala Pro
1               5

<210> SEQ ID NO 123
<211> LENGTH: 8
<212> TYPE: PRT
<213> ORGANISM: Artificial Sequence
<220> FEATURE:
<223> OTHER INFORMATION: Clone 43 - Region 94-101

<400> SEQUENCE: 123

Trp Glu Val Pro Ala Glu Thr Met
1               5

<210> SEQ ID NO 124
<211> LENGTH: 8
<212> TYPE: PRT
<213> ORGANISM: Artificial Sequence
<220> FEATURE:
<223> OTHER INFORMATION: Clone 44 - Region 94-101

<400> SEQUENCE: 124

Trp Arg Val Pro Asn Pro Thr Gly
1               5

<210> SEQ ID NO 125
<211> LENGTH: 8
<212> TYPE: PRT
<213> ORGANISM: Artificial Sequence
<220> FEATURE:
<223> OTHER INFORMATION: Clone 45 - Region 94-101

<400> SEQUENCE: 125

Trp Leu Ile Pro Lys Pro Phe Ile
1               5

<210> SEQ ID NO 126
<211> LENGTH: 8
<212> TYPE: PRT
<213> ORGANISM: Artificial Sequence
<220> FEATURE:
<223> OTHER INFORMATION: Clone 46 - Region 94-101

<400> SEQUENCE: 126

Trp Thr Val Pro Ser Thr Arg Leu
1               5

<210> SEQ ID NO 127
<211> LENGTH: 8
<212> TYPE: PRT
<213> ORGANISM: Artificial Sequence
<220> FEATURE:
<223> OTHER INFORMATION: Clone 47 - Region 94-101

<400> SEQUENCE: 127
```

Arg Trp Ile Pro Gly Lys Met Val
1               5

<210> SEQ ID NO 128
<211> LENGTH: 8
<212> TYPE: PRT
<213> ORGANISM: Artificial Sequence
<220> FEATURE:
<223> OTHER INFORMATION: Clone 1 - Region 94-101

<400> SEQUENCE: 128

Trp Ile Ile Pro Thr Arg Asp Met
1               5

<210> SEQ ID NO 129
<211> LENGTH: 8
<212> TYPE: PRT
<213> ORGANISM: Artificial Sequence
<220> FEATURE:
<223> OTHER INFORMATION: Consensus sequence 94-101
<220> FEATURE:
<221> NAME/KEY: SITE
<222> LOCATION: 2
<223> OTHER INFORMATION: X is any amino acid
<220> FEATURE:
<221> NAME/KEY: SITE
<222> LOCATION: 6
<223> OTHER INFORMATION: X is any amino acid
<220> FEATURE:
<221> NAME/KEY: SITE
<222> LOCATION: 7
<223> OTHER INFORMATION: X is any amino acid
<220> FEATURE:
<221> NAME/KEY: SITE
<222> LOCATION: 8
<223> OTHER INFORMATION: X is any amino acid

<400> SEQUENCE: 129

Trp Xaa Ile Pro Thr Xaa Xaa Xaa
1               5

<210> SEQ ID NO 130
<211> LENGTH: 245
<212> TYPE: PRT
<213> ORGANISM: Artificial Sequence
<220> FEATURE:
<223> OTHER INFORMATION: EGFP-GGGSGGGSPG

<400> SEQUENCE: 130

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

```
Asp Phe Lys Glu Asp Gly Asn Ile Leu Gly His Lys Leu Glu Tyr Asn
            130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Gly Gly Ser Gly
225                 230                 235                 240

Gly Gly Ser Pro Gly
            245

<210> SEQ ID NO 131
<211> LENGTH: 137
<212> TYPE: PRT
<213> ORGANISM: Artificial Sequence
<220> FEATURE:
<223> OTHER INFORMATION: Y-FASTb

<400> SEQUENCE: 131

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Met Ile
                85                  90                  95

Pro Thr Ser Arg Gly Pro Thr Lys Val Lys Val His Met Lys Lys Ala
            100                 105                 110

Leu Ser Gly Asp Ser Tyr Trp Val Phe Val Lys Arg Val Gly Ser Glu
        115                 120                 125

Gln Lys Leu Ile Ser Glu Glu Asp Leu
    130                 135

<210> SEQ ID NO 132
<211> LENGTH: 154
<212> TYPE: PRT
<213> ORGANISM: Artificial Sequence
<220> FEATURE:
<223> OTHER INFORMATION: Y-FASTb

<400> SEQUENCE: 132

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
```

```
                35                  40                  45
Ile Thr Gly Arg Asp Pro Lys Gln Val Ile Gly Lys Asn Phe Phe Lys
 50                  55                  60

Asp Val Ala Pro Gly Thr Asp Ser Pro Glu Phe Tyr Gly Lys Phe Lys
 65                  70                  75                  80

Glu Gly Val Ala Ser Gly Asn Leu Asn Thr Met Phe Glu Trp Met Ile
                 85                  90                  95

Pro Thr Ser Arg Gly Pro Thr Lys Val Lys Val His Met Lys Lys Ala
                100                 105                 110

Leu Ser Gly Asp Ser Tyr Trp Val Phe Val Lys Arg Val Gly Ser Glu
            115                 120                 125

Gln Lys Leu Ile Ser Glu Glu Asp Leu Gly Ala Gly Ala Pro Lys Lys
        130                 135                 140

Lys Arg Lys Val Pro Lys Lys Lys Arg Lys
145                 150

<210> SEQ ID NO 133
<211> LENGTH: 153
<212> TYPE: PRT
<213> ORGANISM: Artificial Sequence
<220> FEATURE:
<223> OTHER INFORMATION: MGCIKSKGKDSAGGGSb

<400> SEQUENCE: 133

Met Gly Cys Ile Lys Ser Lys Gly Lys Asp Ser Ala Gly Gly Gly Ser
 1               5                  10                  15

Met Glu His Val Ala Phe Gly Ser Glu Asp Ile Glu Asn Thr Leu Ala
                20                  25                  30

Lys Met Asp Asp Gly Gln Leu Asp Gly Leu Ala Phe Gly Ala Ile Gln
            35                  40                  45

Leu Asp Gly Asp Gly Asn Ile Leu Gln Tyr Asn Ala Ala Glu Gly Asp
 50                  55                  60

Ile Thr Gly Arg Asp Pro Lys Gln Val Ile Gly Lys Asn Phe Phe Lys
 65                  70                  75                  80

Asp Val Ala Pro Gly Thr Asp Ser Pro Glu Phe Tyr Gly Lys Phe Lys
                 85                  90                  95

Glu Gly Val Ala Ser Gly Asn Leu Asn Thr Met Phe Glu Trp Met Ile
                100                 105                 110

Pro Thr Ser Arg Gly Pro Thr Lys Val Lys Val His Met Lys Lys Ala
            115                 120                 125

Leu Ser Gly Asp Ser Tyr Trp Val Phe Val Lys Arg Val Gly Ser Glu
        130                 135                 140

Gln Lys Leu Ile Ser Glu Glu Asp Leu
145                 150

<210> SEQ ID NO 134
<211> LENGTH: 422
<212> TYPE: PRT
<213> ORGANISM: Artificial Sequence
<220> FEATURE:
<223> OTHER INFORMATION: Ensconsin-SAGG GSb

<400> SEQUENCE: 134

Met Glu Gln Lys Leu Ile Ser Glu Glu Asp Leu Gly Ala Pro Val Arg
 1               5                  10                  15

Ser Glu Thr Ala Pro Asp Ser Tyr Lys Val Gln Asp Lys Lys Asn Ala
                20                  25                  30
```

Ser Ser Arg Pro Ala Ser Ala Ile Ser Gly Gln Asn Asn His Ser
        35                  40                  45
Gly Asn Lys Pro Asp Pro Pro Val Leu Arg Val Asp Asp Arg Gln
 50                  55                  60
Arg Leu Ala Arg Glu Arg Glu Arg Glu Lys Gln Leu Ala Ala
 65                  70                  75                  80
Arg Glu Ile Val Trp Leu Glu Arg Glu Glu Arg Ala Arg Gln His Tyr
                     85                  90                  95
Glu Lys His Leu Glu Glu Arg Lys Arg Leu Glu Glu Gln Arg Gln
            100                 105                 110
Lys Glu Glu Arg Arg Ala Ala Val Glu Glu Lys Arg Arg Gln Arg
            115                 120                 125
Leu Glu Glu Asp Lys Glu Arg His Glu Ala Val Val Arg Arg Thr Met
130                 135                 140
Glu Arg Ser Gln Lys Pro Lys Gln Lys His Asn Arg Trp Ser Trp Gly
145                 150                 155                 160
Gly Ser Leu His Gly Ser Pro Ser Ile His Ser Ala Asp Pro Asp Arg
                    165                 170                 175
Arg Ser Val Ser Thr Met Asn Leu Ser Lys Tyr Val Asp Pro Val Ile
                180                 185                 190
Ser Lys Arg Leu Ser Ser Ser Ala Thr Leu Leu Asn Ser Pro Asp
            195                 200                 205
Arg Ala Arg Arg Leu Gln Leu Ser Pro Trp Glu Ser Ser Val Val Asn
    210                 215                 220
Arg Leu Leu Thr Pro Thr His Ser Phe Leu Ala Arg Ser Lys Ser Thr
225                 230                 235                 240
Ala Ala Leu Ser Gly Glu Ala Ala Ser Cys Ser Pro Ile Ile Met Pro
                    245                 250                 255
Tyr Lys Ala Ala His Ser Arg Asn Ser Met Asp Arg Pro Lys Leu Phe
                260                 265                 270
Val Thr Pro Pro Glu Gly Ser Ser Ala Gly Gly Ser Met Glu His
            275                 280                 285
Val Ala Phe Gly Ser Glu Asp Ile Glu Asn Thr Leu Ala Lys Met Asp
290                 295                 300
Asp Gly Gln Leu Asp Gly Leu Ala Phe Gly Ala Ile Gln Leu Asp Gly
305                 310                 315                 320
Asp Gly Asn Ile Leu Gln Tyr Asn Ala Ala Glu Gly Asp Ile Thr Gly
                325                 330                 335
Arg Asp Pro Lys Gln Val Ile Gly Lys Asn Phe Phe Lys Asp Val Ala
            340                 345                 350
Pro Gly Thr Asp Ser Pro Glu Phe Tyr Gly Lys Phe Lys Glu Gly Val
            355                 360                 365
Ala Ser Gly Asn Leu Asn Thr Met Phe Glu Trp Met Ile Pro Thr Ser
370                 375                 380
Arg Gly Pro Thr Lys Val Lys Val His Met Lys Lys Ala Leu Ser Gly
385                 390                 395                 400
Asp Ser Tyr Trp Val Phe Val Lys Arg Val Gly Ser Glu Gln Lys Leu
                405                 410                 415
Ile Ser Glu Glu Asp Leu
            420

<210> SEQ ID NO 135
<211> LENGTH: 253
<212> TYPE: PRT

```
<213> ORGANISM: Artificial Sequence
<220> FEATURE:
<223> OTHER INFORMATION: Dronpab

<400> SEQUENCE: 135

Val Ser Val Ile Lys Pro Asp Met Lys Ile Lys Leu Arg Met Glu Gly
1               5                   10                  15

Ala Val Asn Gly His Pro Phe Ala Ile Glu Gly Val Gly Leu Gly Lys
            20                  25                  30

Pro Phe Glu Gly Lys Gln Ser Met Asp Leu Lys Val Lys Glu Gly Gly
        35                  40                  45

Pro Leu Pro Phe Ala Tyr Asp Ile Leu Thr Thr Val Phe Cys Tyr Gly
    50                  55                  60

Asn Arg Val Phe Ala Lys Tyr Pro Glu Asn Ile Val Asp Tyr Phe Lys
65                  70                  75                  80

Gln Ser Phe Pro Glu Gly Tyr Ser Trp Glu Arg Ser Met Asn Tyr Glu
                85                  90                  95

Asp Gly Gly Ile Cys Asn Ala Thr Asn Asp Ile Thr Leu Asp Gly Asp
            100                 105                 110

Cys Tyr Ile Tyr Glu Ile Arg Phe Asp Gly Val Asn Phe Pro Ala Asn
        115                 120                 125

Gly Pro Val Met Gln Lys Arg Thr Val Lys Trp Glu Pro Ser Thr Glu
    130                 135                 140

Lys Leu Tyr Val Arg Asp Gly Val Leu Lys Gly Asp Val Asn Met Ala
145                 150                 155                 160

Leu Ser Leu Glu Gly Gly Gly His Tyr Arg Cys Asp Phe Lys Thr Thr
                165                 170                 175

Tyr Lys Ala Lys Lys Val Val Gln Leu Pro Asp Tyr His Phe Val Asp
            180                 185                 190

His His Ile Glu Ile Lys Ser His Asp Lys Asp Tyr Ser Asn Val Asn
        195                 200                 205

Leu His Glu His Ala Glu Ala His Ser Glu Leu Pro Arg Gln Ala Lys
    210                 215                 220

Gly Ser Glu Gln Lys Leu Ile Ser Glu Glu Asp Leu Gly Ala Gly Ala
225                 230                 235                 240

Pro Lys Lys Lys Arg Lys Val Pro Lys Lys Lys Arg Lys
                245                 250

<210> SEQ ID NO 136
<211> LENGTH: 252
<212> TYPE: PRT
<213> ORGANISM: Artificial Sequence
<220> FEATURE:
<223> OTHER INFORMATION: MGCIKSKGKDSAGGGSb

<400> SEQUENCE: 136

Met Gly Cys Ile Lys Ser Lys Gly Lys Asp Ser Ala Gly Gly Gly Ser
1               5                   10                  15

Val Ser Val Ile Lys Pro Asp Met Lys Ile Lys Leu Arg Met Glu Gly
            20                  25                  30

Ala Val Asn Gly His Pro Phe Ala Ile Glu Gly Val Gly Leu Gly Lys
        35                  40                  45

Pro Phe Glu Gly Lys Gln Ser Met Asp Leu Lys Val Lys Glu Gly Gly
    50                  55                  60

Pro Leu Pro Phe Ala Tyr Asp Ile Leu Thr Thr Val Phe Cys Tyr Gly
65                  70                  75                  80
```

```
Asn Arg Val Phe Ala Lys Tyr Pro Glu Asn Ile Val Asp Tyr Phe Lys
                85                  90                  95

Gln Ser Phe Pro Glu Gly Tyr Ser Trp Glu Arg Ser Met Asn Tyr Glu
            100                 105                 110

Asp Gly Gly Ile Cys Asn Ala Thr Asn Asp Ile Thr Leu Asp Gly Asp
            115                 120                 125

Cys Tyr Ile Tyr Glu Ile Arg Phe Asp Gly Val Asn Phe Pro Ala Asn
130             135                 140

Gly Pro Val Met Gln Lys Arg Thr Val Lys Trp Glu Pro Ser Thr Glu
145             150                 155                 160

Lys Leu Tyr Val Arg Asp Gly Val Leu Lys Gly Asp Val Asn Met Ala
                165                 170                 175

Leu Ser Leu Glu Gly Gly Gly His Tyr Arg Cys Asp Phe Lys Thr Thr
            180                 185                 190

Tyr Lys Ala Lys Lys Val Val Gln Leu Pro Asp Tyr His Phe Val Asp
            195                 200                 205

His His Ile Glu Ile Lys Ser Asp Lys Asp Tyr Ser Asn Val Asn
            210                 215                 220

Leu His Glu His Ala Glu Ala His Ser Glu Leu Pro Arg Gln Ala Lys
225             230                 235                 240

Gly Ser Glu Gln Lys Leu Ile Ser Glu Glu Asp Leu
                245                 250

<210> SEQ ID NO 137
<211> LENGTH: 150
<212> TYPE: PRT
<213> ORGANISM: Artificial Sequence
<220> FEATURE:
<223> OTHER INFORMATION: ATNFSLLKQAGDVEENPGPSRGGGSb

<400> SEQUENCE: 137

Ala Thr Asn Phe Ser Leu Leu Lys Gln Ala Gly Asp Val Glu Glu Asn
1               5                   10                  15

Pro Gly Pro Ser Arg Gly Gly Gly Ser Met Glu His Val Ala Phe Gly
            20                  25                  30

Ser Glu Asp Ile Glu Asn Thr Leu Ala Lys Met Asp Asp Gly Gln Leu
            35                  40                  45

Asp Gly Leu Ala Phe Gly Ala Ile Gln Leu Asp Gly Asp Gly Asn Ile
        50                  55                  60

Leu Gln Tyr Asn Ala Ala Glu Gly Asp Ile Thr Gly Arg Asp Pro Lys
65              70                  75                  80

Gln Val Ile Gly Lys Asn Phe Phe Lys Asp Val Ala Pro Gly Thr Asp
                85                  90                  95

Ser Pro Glu Phe Tyr Gly Lys Phe Lys Glu Gly Val Ala Ser Gly Asn
            100                 105                 110

Leu Asn Thr Met Phe Glu Trp Met Ile Pro Thr Ser Arg Gly Pro Thr
            115                 120                 125

Lys Val Lys Val His Met Lys Lys Ala Leu Ser Gly Asp Ser Tyr Trp
            130                 135                 140

Val Phe Val Lys Arg Val
145                 150

<210> SEQ ID NO 138
<211> LENGTH: 388
<212> TYPE: PRT
<213> ORGANISM: Artificial Sequence
<220> FEATURE:
```

<223> OTHER INFORMATION: mCherry-GSGATNFSLLKQAGDVEENPGPSRGGGSb

<400> SEQUENCE: 138

```
Val Ser Lys Gly Glu Asp Asn Met Ala Ile Ile Lys Glu Phe Met
1               5                   10                  15

Arg Phe Lys Val His Met Glu Gly Ser Val Asn Gly His Glu Phe Glu
            20                  25                  30

Ile Glu Gly Glu Gly Glu Gly Arg Pro Tyr Glu Gly Thr Gln Thr Ala
            35                  40                  45

Lys Leu Lys Val Thr Lys Gly Gly Pro Leu Pro Phe Ala Trp Asp Ile
50                  55                  60

Leu Ser Pro Gln Phe Met Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Val Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
            115                 120                 125

Arg Gly Thr Asn Phe Pro Ser Asp Gly Pro Val Met Gln Lys Lys Thr
130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
                165                 170                 175

Tyr Asp Ala Glu Val Lys Thr Thr Tyr Lys Ala Lys Lys Pro Val Gln
            180                 185                 190

Leu Pro Gly Ala Tyr Asn Val Asn Ile Lys Leu Asp Ile Thr Ser His
            195                 200                 205

Asn Glu Asp Tyr Thr Ile Val Glu Gln Tyr Glu Arg Ala Glu Gly Arg
210                 215                 220

His Ser Thr Gly Gly Met Asp Glu Leu Tyr Lys Gly Ser Gly Ala Thr
225                 230                 235                 240

Asn Phe Ser Leu Leu Lys Gln Ala Gly Asp Val Glu Glu Asn Pro Gly
                245                 250                 255

Pro Ser Arg Gly Gly Gly Ser Met Glu His Val Ala Phe Gly Ser Glu
            260                 265                 270

Asp Ile Glu Asn Thr Leu Ala Lys Met Asp Asp Gly Gln Leu Asp Gly
            275                 280                 285

Leu Ala Phe Gly Ala Ile Gln Leu Asp Gly Asp Gly Asn Ile Leu Gln
            290                 295                 300

Tyr Asn Ala Ala Glu Gly Asp Ile Thr Gly Arg Asp Pro Lys Gln Val
305                 310                 315                 320

Ile Gly Lys Asn Phe Phe Lys Asp Val Ala Pro Gly Thr Asp Ser Pro
                325                 330                 335

Glu Phe Tyr Gly Lys Phe Lys Glu Gly Val Ala Ser Gly Asn Leu Asn
            340                 345                 350

Thr Met Phe Glu Tyr Thr Phe Asp Tyr Gln Met Thr Pro Thr Lys Val
            355                 360                 365

Lys Val His Met Lys Lys Ala Leu Ser Gly Asp Ser Tyr Trp Val Phe
370                 375                 380

Val Lys Arg Val
385
```

<210> SEQ ID NO 139
<211> LENGTH: 374
<212> TYPE: DNA
<213> ORGANISM: Artificial Sequence
<220> FEATURE:
<223> OTHER INFORMATION: PYP-C69G codon-optimized for expression in yeast cells

<400> SEQUENCE: 139

```
atggaacatg ttgcctttgg tagcgaagat atcgagaata ctctagcgaa aatggatgat     60
ggccaattag atgattagc ctttggtgct atacagcttg atggtgatgg caatattctg     120
cagtataatg cagctgaagg agacataaca gggagagatc ccaaacaagt gattggcaag    180
aacttcttca agacgtagc accaggtaca gattctcctg aattttacgg gaaattcaag    240
gaaggagtag catcaggtaa cttgaatacc atgttcgagt atacgtttga ctaccaaatg    300
actccaacca aggttaaagt ccacatgaag aaggctttga gtggtgactc ctattgggtg    360
tttgtcaaaa gggt                                                      374
```

<210> SEQ ID NO 140
<211> LENGTH: 375
<212> TYPE: DNA
<213> ORGANISM: Artificial Sequence
<220> FEATURE:
<223> OTHER INFORMATION: Y-FAST selected by yeast display

<400> SEQUENCE: 140

```
atggaacatg ttgcctttgg tagcgaagat atcgagaata ctctagcgaa aatggatgat     60
ggccaattag atgattagc ctttggtgct atacagcttg atggtgatgg caatattctg     120
cagtataatg cagctgaagg agacataaca gggagagatc ccaaacaagt gattggcaag    180
aacttcttca agacgtagc accaggtaca gattctcctg aattttacgg gaaattcaag    240
gaaggagtag catcaggtaa cttgaatacc atgttcgagt ggatgattcc gacgagtagg    300
gggccaacca aggttaaagt ccacatgaag aaggctttga gtggtgactc ctattgggtg    360
tttgtcaaaa gggtt                                                     375
```

<210> SEQ ID NO 141
<211> LENGTH: 375
<212> TYPE: DNA
<213> ORGANISM: Artificial Sequence
<220> FEATURE:
<223> OTHER INFORMATION: Y-FAST codon-optimized for expression in human cells

<400> SEQUENCE: 141

```
atggagcatg ttgcctttgg cagtgaggac atcgagaaca ctctggccaa aatggacgac     60
ggacaactgg atgggttggc ctttggcgca attcagctcg atggtgacgg gaatatcctg    120
cagtacaatg ctgctgaagg agacatcaca ggcagagatc ccaaacaggt gattgggaag    180
aacttcttca aggatgttgc acctggaacg gattctcccg agttttacgg caaattcaag    240
gaaggcgtag cgtcagggaa tctgaacacc atgttcgaat ggatgatacc gacaagcagg    300
ggaccaacca aggtcaaggt gcacatgaag aaagcccttt ccggtgacag ctattgggtc    360
tttgtgaaac gggtg                                                     375
```

<210> SEQ ID NO 142
<211> LENGTH: 21
<212> TYPE: DNA
<213> ORGANISM: Artificial Sequence

```
<220> FEATURE:
<223> OTHER INFORMATION: Primer AG42

<400> SEQUENCE: 142
ggtcggctag catggaacat g                                              21

<210> SEQ ID NO 143
<211> LENGTH: 50
<212> TYPE: DNA
<213> ORGANISM: Artificial Sequence
<220> FEATURE:
<223> OTHER INFORMATION: Primer AG43
<220> FEATURE:
<221> NAME/KEY: misc_feature
<222> LOCATION: 28
<223> OTHER INFORMATION: /note="n is A or T or G or C"
<220> FEATURE:
<221> NAME/KEY: misc_feature
<222> LOCATION: 29
<223> OTHER INFORMATION: /note="n is A or T or G or C"
<220> FEATURE:
<221> NAME/KEY: misc_feature
<222> LOCATION: 31
<223> OTHER INFORMATION: /note="n is A or T or G or C"
<220> FEATURE:
<221> NAME/KEY: misc_feature
<222> LOCATION: 32
<223> OTHER INFORMATION: /note="n is A or T or G or C"

<400> SEQUENCE: 143
aagttcttgc caatcacttg tttgggmnnm nncctgtta tgtctccttc                50

<210> SEQ ID NO 144
<211> LENGTH: 58
<212> TYPE: DNA
<213> ORGANISM: Artificial Sequence
<220> FEATURE:
<223> OTHER INFORMATION: Primer AG44
<220> FEATURE:
<221> NAME/KEY: misc_feature
<222> LOCATION: 23
<223> OTHER INFORMATION: /note="n is A or T or C or G"
<220> FEATURE:
<221> NAME/KEY: misc_feature
<222> LOCATION: 24
<223> OTHER INFORMATION: /note="n is A or T or C or G"
<220> FEATURE:
<221> NAME/KEY: misc_feature
<222> LOCATION: 26
<223> OTHER INFORMATION: /note="n is A or T or C or G"
<220> FEATURE:
<221> NAME/KEY: misc_feature
<222> LOCATION: 27
<223> OTHER INFORMATION: /note="n is A or T or C or G"
<220> FEATURE:
<221> NAME/KEY: misc_feature
<222> LOCATION: 29
<223> OTHER INFORMATION: /note="n is A or T or C or G"
<220> FEATURE:
<221> NAME/KEY: misc_feature
<222> LOCATION: 30
<223> OTHER INFORMATION: /note="n is A or T or C or G"
<220> FEATURE:
<221> NAME/KEY: misc_feature
<222> LOCATION: 32
<223> OTHER INFORMATION: /note="n is A or T or C or G"
<220> FEATURE:
<221> NAME/KEY: misc_feature
<222> LOCATION: 33
<223> OTHER INFORMATION: /note="n is A or T or C or G"
<220> FEATURE:
<221> NAME/KEY: misc_feature
<222> LOCATION: 35
<223> OTHER INFORMATION: /note="n is A or T or C or G"
<220> FEATURE:
```

```
<221> NAME/KEY: misc_feature
<222> LOCATION: 36
<223> OTHER INFORMATION: /note="n is A or T or C or G"

<400> SEQUENCE: 144
gattggcaag aacttcttca aannknnknn knnknnkaca gattctcctg aattttac      58

<210> SEQ ID NO 145
<211> LENGTH: 58
<212> TYPE: DNA
<213> ORGANISM: Artificial Sequence
<220> FEATURE:
<223> OTHER INFORMATION: Primer AG45
<220> FEATURE:
<221> NAME/KEY: misc_feature
<222> LOCATION: 17
<223> OTHER INFORMATION: /note="n is A or T or C or G"
<220> FEATURE:
<221> NAME/KEY: misc_feature
<222> LOCATION: 18
<223> OTHER INFORMATION: /note="n is A or T or C or G"
<220> FEATURE:
<221> NAME/KEY: misc_feature
<222> LOCATION: 20
<223> OTHER INFORMATION: /note="n is A or T or C or G"
<220> FEATURE:
<221> NAME/KEY: misc_feature
<222> LOCATION: 21
<223> OTHER INFORMATION: /note="n is A or T or C or G"
<220> FEATURE:
<221> NAME/KEY: misc_feature
<222> LOCATION: 23
<223> OTHER INFORMATION: /note="n is A or T or C or G"
<220> FEATURE:
<221> NAME/KEY: misc_feature
<222> LOCATION: 24
<223> OTHER INFORMATION: /note="n is A or T or C or G"
<220> FEATURE:
<221> NAME/KEY: misc_feature
<222> LOCATION: 26
<223> OTHER INFORMATION: /note="n is A or T or C or G"
<220> FEATURE:
<221> NAME/KEY: misc_feature
<222> LOCATION: 27
<223> OTHER INFORMATION: /note="n is A or T or C or G"
<220> FEATURE:
<221> NAME/KEY: misc_feature
<222> LOCATION: 29
<223> OTHER INFORMATION: /note="n is A or T or C or G"
<220> FEATURE:
<221> NAME/KEY: misc_feature
<222> LOCATION: 30
<223> OTHER INFORMATION: /note="n is A or T or C or G"
<220> FEATURE:
<221> NAME/KEY: misc_feature
<222> LOCATION: 32
<223> OTHER INFORMATION: /note="n is A or T or C or G"
<220> FEATURE:
<221> NAME/KEY: misc_feature
<222> LOCATION: 33
<223> OTHER INFORMATION: /note="n is A or T or C or G"
<220> FEATURE:
<221> NAME/KEY: misc_feature
<222> LOCATION: 35
<223> OTHER INFORMATION: /note="n is A or T or C or G"
<220> FEATURE:
<221> NAME/KEY: misc_feature
<222> LOCATION: 36
<223> OTHER INFORMATION: /note="n is A or T or C or G"
<220> FEATURE:
<221> NAME/KEY: misc_feature
<222> LOCATION: 38
<223> OTHER INFORMATION: /note="n is A or T or C or G"
<220> FEATURE:
<221> NAME/KEY: misc_feature
<222> LOCATION: 39
<223> OTHER INFORMATION: /note="n is A or T or C or G"
```

<400> SEQUENCE: 145
tttaaccttg gttggmnnmn nmnmnmnmn mnnmnmnnc tcgaacatgg tattcaag    58

<210> SEQ ID NO 146
<211> LENGTH: 23
<212> TYPE: DNA
<213> ORGANISM: Artificial Sequence
<220> FEATURE:
<223> OTHER INFORMATION: Primer AG46

<400> SEQUENCE: 146
tttgttcgga tccaacccttt ttg    23

<210> SEQ ID NO 147
<211> LENGTH: 20
<212> TYPE: DNA
<213> ORGANISM: Artificial Sequence
<220> FEATURE:
<223> OTHER INFORMATION: Primer AG47

<400> SEQUENCE: 147
cgttccagac tacgctctgc    20

<210> SEQ ID NO 148
<211> LENGTH: 7
<212> TYPE: PRT
<213> ORGANISM: Artificial Sequence
<220> FEATURE:
<223> OTHER INFORMATION: TEV recognition sequence

<400> SEQUENCE: 148

Glu Asn Leu Tyr Phe Gln Gly
1               5

<210> SEQ ID NO 149
<211> LENGTH: 235
<212> TYPE: PRT
<213> ORGANISM: Artificial Sequence
<220> FEATURE:
<223> OTHER INFORMATION: mCherry

<400> SEQUENCE: 149

Val Ser Lys Gly Glu Glu Asp Asn Met Ala Ile Ile Lys Glu Phe Met
1               5                   10                  15

Arg Phe Lys Val His Met Glu Gly Ser Val Asn Gly His Glu Phe Glu
            20                  25                  30

Ile Glu Gly Glu Gly Glu Gly Arg Pro Tyr Glu Gly Thr Gln Thr Ala
        35                  40                  45

Lys Leu Lys Val Thr Lys Gly Gly Pro Leu Pro Phe Ala Trp Asp Ile
    50                  55                  60

Leu Ser Pro Gln Phe Met Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Val Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
        115                 120                 125

Arg Gly Thr Asn Phe Pro Ser Asp Gly Pro Val Met Gln Lys Lys Thr
    130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
            165                 170                 175

Tyr Asp Ala Glu Val Lys Thr Thr Tyr Lys Ala Lys Lys Pro Val Gln
                180                 185                 190

Leu Pro Gly Ala Tyr Asn Val Asn Ile Lys Leu Asp Ile Thr Ser His
        195                 200                 205

Asn Glu Asp Tyr Thr Ile Val Glu Gln Tyr Glu Arg Ala Glu Gly Arg
    210                 215                 220

His Ser Thr Gly Gly Met Asp Glu Leu Tyr Lys
225                 230                 235

<210> SEQ ID NO 150
<211> LENGTH: 364
<212> TYPE: PRT
<213> ORGANISM: Artificial Sequence
<220> FEATURE:
<223> OTHER INFORMATION: mCherryb

<400> SEQUENCE: 150

Val Ser Lys Gly Glu Glu Asp Asn Met Ala Ile Ile Lys Glu Phe Met
1               5                   10                  15

Arg Phe Lys Val His Met Glu Gly Ser Val Asn Gly His Glu Phe Glu
                20                  25                  30

Ile Glu Gly Glu Gly Glu Gly Arg Pro Tyr Glu Gly Thr Gln Thr Ala
            35                  40                  45

Lys Leu Lys Val Thr Lys Gly Gly Pro Leu Pro Phe Ala Trp Asp Ile
50                  55                  60

Leu Ser Pro Gln Phe Met Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Val Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
        115                 120                 125

Arg Gly Thr Asn Phe Pro Ser Asp Gly Pro Val Met Gln Lys Lys Thr
    130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
            165                 170                 175

Tyr Asp Ala Glu Val Lys Thr Thr Tyr Lys Ala Lys Lys Pro Val Gln
                180                 185                 190

Leu Pro Gly Ala Tyr Asn Val Asn Ile Lys Leu Asp Ile Thr Ser His
        195                 200                 205

Asn Glu Asp Tyr Thr Ile Val Glu Gln Tyr Glu Arg Ala Glu Gly Arg
    210                 215                 220

His Ser Thr Gly Gly Met Asp Glu Leu Tyr Lys Gly Gly Ser Met
225                 230                 235                 240

Glu His Val Ala Phe Gly Ser Glu Asp Ile Glu Asn Thr Leu Ala Lys
                245                 250                 255

Met Asp Asp Gly Gln Leu Asp Gly Leu Ala Phe Gly Ala Ile Gln Leu
            260                 265                 270

```
Asp Gly Asp Gly Asn Ile Leu Gln Tyr Asn Ala Ala Glu Gly Asp Ile
            275                 280                 285

Thr Gly Arg Asp Pro Lys Gln Val Ile Gly Lys Asn Phe Phe Lys Asp
290                 295                 300

Val Ala Pro Gly Thr Asp Ser Pro Glu Phe Tyr Gly Lys Phe Lys Glu
305                 310                 315                 320

Gly Val Ala Ser Gly Asn Leu Asn Thr Met Phe Glu Trp Met Ile Pro
                325                 330                 335

Thr Ser Arg Gly Pro Thr Lys Val Lys Val His Met Lys Lys Ala Leu
            340                 345                 350

Ser Gly Asp Ser Tyr Trp Val Phe Val Lys Arg Val
            355                 360

<210> SEQ ID NO 151
<211> LENGTH: 364
<212> TYPE: PRT
<213> ORGANISM: Artificial Sequence
<220> FEATURE:
<223> OTHER INFORMATION: mCherryb

<400> SEQUENCE: 151

Val Ser Lys Gly Glu Glu Asp Asn Met Ala Ile Ile Lys Glu Phe Met
1               5                   10                  15

Arg Phe Lys Val His Met Glu Gly Ser Val Asn Gly His Glu Phe Glu
                20                  25                  30

Ile Glu Gly Glu Gly Glu Gly Arg Pro Tyr Glu Gly Thr Gln Thr Ala
            35                  40                  45

Lys Leu Lys Val Thr Lys Gly Gly Pro Leu Pro Phe Ala Trp Asp Ile
50                  55                  60

Leu Ser Pro Gln Phe Met Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Val Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
        115                 120                 125

Arg Gly Thr Asn Phe Pro Ser Asp Gly Pro Val Met Gln Lys Lys Thr
130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
                165                 170                 175

Tyr Asp Ala Glu Val Lys Thr Thr Tyr Lys Ala Lys Lys Pro Val Gln
            180                 185                 190

Leu Pro Gly Ala Tyr Asn Val Asn Ile Lys Leu Asp Ile Thr Ser His
        195                 200                 205

Asn Glu Asp Tyr Thr Ile Val Glu Gln Tyr Glu Arg Ala Glu Gly Arg
210                 215                 220

His Ser Thr Gly Gly Met Asp Glu Leu Tyr Lys Gly Gly Ser Met
225                 230                 235                 240

Glu His Val Ala Phe Gly Ser Glu Asp Ile Glu Asn Thr Leu Ala Lys
                245                 250                 255

Met Asp Asp Gly Gln Leu Asp Gly Leu Ala Phe Gly Ala Ile Gln Leu
            260                 265                 270
```

```
Asp Gly Asp Gly Asn Ile Leu Gln Tyr Asn Ala Ala Glu Gly Asp Ile
            275                 280                 285

Thr Gly Arg Asp Pro Lys Gln Val Ile Gly Lys Asn Phe Phe Lys Asp
290                 295                 300

Val Ala Pro Gly Thr Asp Ser Pro Glu Phe Tyr Gly Lys Phe Lys Glu
305                 310                 315                 320

Gly Val Ala Ser Gly Asn Leu Asn Thr Met Phe Glu Tyr Thr Phe Asp
                325                 330                 335

Tyr Gln Met Thr Pro Thr Lys Val Lys Val His Met Lys Lys Ala Leu
            340                 345                 350

Ser Gly Asp Ser Tyr Trp Val Phe Val Lys Arg Val
            355                 360

<210> SEQ ID NO 152
<211> LENGTH: 371
<212> TYPE: PRT
<213> ORGANISM: Artificial Sequence
<220> FEATURE:
<223> OTHER INFORMATION: mCherryb

<400> SEQUENCE: 152

Val Ser Lys Gly Glu Glu Asp Asn Met Ala Ile Ile Lys Glu Phe Met
1               5                   10                  15

Arg Phe Lys Val His Met Glu Gly Ser Val Asn Gly His Glu Phe Glu
                20                  25                  30

Ile Glu Gly Glu Gly Glu Gly Arg Pro Tyr Glu Gly Thr Gln Thr Ala
            35                  40                  45

Lys Leu Lys Val Thr Lys Gly Gly Pro Leu Pro Phe Ala Trp Asp Ile
50                  55                  60

Leu Ser Pro Gln Phe Met Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Val Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
        115                 120                 125

Arg Gly Thr Asn Phe Pro Ser Asp Gly Pro Val Met Gln Lys Lys Thr
130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
                165                 170                 175

Tyr Asp Ala Glu Val Lys Thr Thr Tyr Lys Ala Lys Lys Pro Val Gln
            180                 185                 190

Leu Pro Gly Ala Tyr Asn Val Asn Ile Lys Leu Asp Ile Thr Ser His
        195                 200                 205

Asn Glu Asp Tyr Thr Ile Val Glu Gln Tyr Glu Arg Ala Glu Gly Arg
210                 215                 220

His Ser Thr Gly Gly Met Asp Glu Leu Tyr Lys Gly Ser Ser Ser Glu
225                 230                 235                 240

Asn Leu Tyr Phe Gln Gly Met Glu His Val Ala Phe Gly Ser Glu Asp
                245                 250                 255

Ile Glu Asn Thr Leu Ala Lys Met Asp Asp Gly Gln Leu Asp Gly Leu
            260                 265                 270
```

```
Ala Phe Gly Ala Ile Gln Leu Asp Gly Asp Gly Asn Ile Leu Gln Tyr
            275                 280                 285

Asn Ala Ala Glu Gly Asp Ile Thr Gly Arg Asp Pro Lys Gln Val Ile
        290                 295                 300

Gly Lys Asn Phe Phe Lys Asp Val Ala Pro Gly Thr Asp Ser Pro Glu
305                 310                 315                 320

Phe Tyr Gly Lys Phe Lys Glu Gly Val Ala Ser Gly Asn Leu Asn Thr
                325                 330                 335

Met Phe Glu Trp Met Ile Pro Thr Ser Arg Gly Pro Thr Lys Val Lys
            340                 345                 350

Val His Met Lys Lys Ala Leu Ser Gly Asp Ser Tyr Trp Val Phe Val
            355                 360                 365

Lys Arg Val
        370
```

FLUOROGEN ACTIVATING AND SHIFTING TAG (FAST)

FIELD OF INVENTION

The present invention pertains to the field of fluorescent labelling of proteins. In particular, the present invention relates to a functional derivative of a Photoactive Yellow Protein (PYP), or a functional fragment thereof, for fluorescently labelling particles, e.g. proteins, or surfaces, whose fluorescence can be turned on and off at will by addition or withdrawal of a non-toxic fluorogenic ligand. In some embodiment, the functional derivative of the invention is capable of binding reversibly a fluorogenic chromophore of formula (I), and is capable of enhancing the brightness of the said fluorogenic chromophore upon complexation; of inducing the spectral shift of the said fluorogenic chromophore through the ionization of an auxochromic group thereof, and binds said fluorogenic chromophore with a renewal time suitable for displaying an apparent photostability.

BACKGROUND OF INVENTION

Understanding living systems requires to be able to observe the dynamics of cellular proteins in real-time with a very high resolution both in space and time. In this context, fluorescence has become the read-out of choice for observing or detecting proteins in living cells or living organisms.

The selective detection of a protein of interest by fluorescence microscopy requires the presence of a fluorescent probe that acts as a contrast agent. This probe can be intrinsic, i.e. be part of the native protein, or extrinsic, i.e. specifically attached to the protein. Most of the time, a protein of interest does not possess a specific intrinsic probe that can give a unique optical signature for fluorescence imaging. Therefore, functionalization of the protein with a fluorescent probe displaying photophysical properties not present in the biological system under study ensures a specific optical signature. The method of choice for obtaining a specific labeling in living cells is to fuse the protein of interest to an additional polypeptide, a so-called tag, which can become fluorescent by an autocatalytic process generating a fluorophore, as in the green fluorescent protein (GFP), or act as an anchor for the specific and tight (covalent or non-covalent) binding of a fluorophore.

In this context, an ideal fluorescent protein-based probe must (i) not perturb the function of the protein it is attached to, which includes not interfering with the overall folding of the native protein, not interfering with the localization of the protein, not changing its interaction with partners, (ii) be functional in the cellular compartment where the protein acts no matter what the pH or redox conditions are, and in the conditions of living of the cells or organisms under study, (iii) enable the imaging of the protein with time resolution compatible with the time scales found among biological processes. This latter point means that ideally a protein-based fluorescent probe must (i) be fluorescent as soon as the fusion protein is folded to report on early stage of the protein life, (ii) be photostable on long-term to allow for quantitative observation of proteins involved in slow dynamic cellular processes. This latter point is particularly important as quantitative observation of fluorescently labeled proteins by fluorescence microscopy is often limited by the photobleaching of the fluorophore. Indeed, as organic fluorophores can only experience a limited number of excitation-emission photocycles resulting in the production of only a limited number of photons before being photochemically destroyed, continuous observation longer than few seconds or few minutes is in general impossible in fluorescence microscopy, which is particularly problematic for long-term tracking or single-molecule imaging.

Specific fluorescent labelling of a protein of interest in living cells is generally achieved through the use of an additional polypeptide, a so-called tag, which is fused to the protein of interest. This is easily done with the currently available DNA recombinant technology: the DNA sequence encoding the additional polypeptide is cloned in frame with the DNA sequence encoding the protein of interest. The resulting DNA sequence encodes a chimeric protein resulting from the fusion of the two polypeptides.

Among the known technologies, the additional peptidic tag can become fluorescent by itself through an autocatalytic process. This is the case for the green fluorescent protein (GFP) identified in the jellyfish *Aequorea Victoria*. The covalent chromophore of GFP, the parahydroxybenzylidene-5-imidazolinone (p-HBI) results from the cyclization/dehydration/oxidation of a triad Gly/Tyr/Ser in the protein backbone. This approach benefits from the fully genetically encoding of the fluorophore as the chromophore forms from the peptidic sequence of GFP. There is therefore an absolute specificity of the fluorescent labeling when using GFP as a fluorescent probe. Several GFP-like proteins have been discovered or engineered to obtain a collection of GFP-like proteins with photophysical properties in the whole visible spectrum. However, this approach suffers from several limitations. First, the autocatalytic maturation of the fluorophore within the protein beta-barrel is a slow multi-step process with a half-time between 40 minutes and 2 hours for most fluorescent proteins (Chudakov et al., 2010): there is thus a lag time between the end of the protein folding and the appearance of the fluorescence, which prevent the study of early stage of the protein life. The second limitation is that molecular $O_2$ is necessary during the oxidation steps involved in the fluorophore formation, which limits the use of such GFP-like fluorescent proteins to environments with $O_2$ (>3 µM) (Hansen et al., 2001), and prevents their use as reporters in anoxic or hypoxic biological systems. The third limitation is the photostability of the GFP-like fluorescent proteins. The photobleaching halftime (required to reduce the emission rate to 50% from an initial emission rate of 1,000 photons/s per fluorescent protein) for common GFP-like fluorescent proteins is typically between 5 and 200 s (Shaner et al., 2005). Finally, the size of the GFP-like fluorescent proteins, comprised between 25 and 30 kDa, has been shown in some cases to modify the function of the protein it is fused to.

Alternative fluorescent proteins relying on a small apoprotein that strongly binds covalently or non-covalently an endogenous fluorogenic cofactor are also used. The binding leads to an exaltation of the cofactor brightness. Fluorescence exaltation results from constraining the fluorogenic cofactor within a particular conformation, favoring radiative deexcitation. Relying on the binding of an endogenous cofactor enables to overcome the necessity for molecular oxygen allowing working under anoxic conditions. Moreover, most of the known alternative cofactor-based fluorescent proteins are much smaller than GFP, which is an advantage to minimize the risk of perturbing the function of the studied protein.

Among these alternative fluorescent proteins, bacteriophytochromes binding covalently biliverdin were engineered into near-infrared fluorescent proteins such as IFP1.4 (Shu et al., 2009), iRFP (Filonov et al., 2011) and Wi-Phy (Auldridge et al., 2012). However, these proteins have a long maturation time (halftime 2 hours) because they require the covalent attachment of the biliverdin cofactor. Moreover, they are multimeric, which can modify the function and localization of the studied protein. Finally they show photostability half time between 50 and 450 s, which is of the same order of magnitude than the GFP-like fluorescent proteins.

Flavin mononucleotide (FMN)-binding green fluorescent proteins were engineered from Light-oxygen-voltage-sensing (LOV) domains (Chapman et al., 2008; Drepper et al., 2007; Shu et al., 2011). These proteins bind non-covalently FMN with subnanomolar affinity. They have been shown to be a good substitute of GFP for studies in anaerobic conditions.

Recently, a green fluorescent protein called UnaG was identified from unagi eel (Kumagai et al., 2013); its fluorescence results from the non-covalent tight binding of bilirubin with subnamolar affinity. The formation of the fluorescent protein is fast and does not require oxygen.

In parallel of these developments, a hybrid concept has been proposed based on engineered single-chain antibodies acting as fluorogen-activating proteins (FAP), which bind noncovalently well-known synthetic fluorogens (mostly molecular rotors and cyanines) (Ozhalici-Unal et al., 2008; Shank et al., 2009; Szent-Gyorgyi et al., 2008). Single-chain antibody (scFv) reporters generating fluorescence from otherwise weakly fluorescent thiazole orange and malachite green have been isolated by screening scFvs libraries by fluorescence activating cell sorting (FACS) (Szent-Gyorgyi et al., 2008). However ScFv-based FAP contains disulfide linkages, and are therefore adapted only for use in non-reducing environments, such as the cell surface and the secretory apparatus.

However, there is still a need in the art for a tunable protein-based reporting system for imaging fusion proteins comprising a protein of interest fused to a fluorescent tag in living cells and in multi-cellular organisms, wherein said reporting system implies a highly dynamic binding to a fluorogen, thereby allowing the fluorescence to be switched on and off rapidly by addition or withdrawing of the fluorogen, opening new opportunities for multiplexing imaging.

SUMMARY

This invention thus relates to a polypeptide comprising a functional photoactive yellow protein (PYP) derivative or a functional fragment thereof, wherein said polypeptide or fragment thereof binds reversibly a fluorogenic chromophore with:
- a $K_D$ ranging from about 0.05 to about 10 μM when measured at a temperature of about 25° C., preferably ranging from about 0.1 to about 2 μM, more preferably ranging from about 0.13 to about 1.02 μM; and/or
- a $k_{off}$ ranging from about 1 to about 50 s$^{-1}$ when measured at a temperature of about 25° C., preferably from about 5 to about 20 s$^{-1}$, more preferably from about 6.3 to about 17 s$^{-1}$; and/or
- a $k_{on}$ ranging from about 0.1×10$^7$ to about 50×10$^7$ M$^{-1}$s$^{-1}$ when measured at a temperature of about 25° C., preferably from about 1×10$^7$ to about 10×10$^7$ M$^{-1}$s$^{-1}$, more preferably from about 3×10$^7$ to about 6.3×10$^7$ M$^{-1}$s$^{-1}$.

In one embodiment, the polypeptide binds reversibly a fluorogenic chromophore of formula (I):

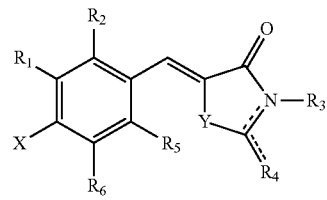

formula (I)

wherein
R1, R2, R5 and R6 may be identical or different and each represents H, halo, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl; and
R3 represents a non-binding doublet (i.e. a free pair of electrons) or H, halo, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy or haloalkyl;
R4 is a single or a double bound, interrupted or terminated by S, O or N atom, optionally substituted by at least one group selected from H, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl;
X is OH, SH, NHR7, or N(R7)$_2$, wherein R7 is H, halo, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl; and
Y is O, NH or S;
wherein said polypeptide enhances the brightness of the said fluorogenic chromophore upon complexation thereto;
wherein said polypeptide induces the spectral shift of the said fluorogenic chromophore through the ionization of an auxochromic group thereof, and
wherein said polypeptide binds said fluorogenic chromophore with a renewal time suitable for displaying an apparent photostability.

In a particular embodiment, the said fluorogenic chromophore has the formula (II):

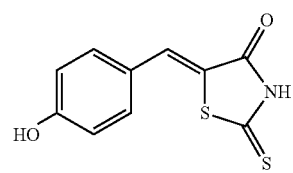

formula (II)

In a particular embodiment, the dissociation constant (KD) of said polypeptide with said fluorogenic chromophore ranges from about 0.1 μM to about 10 μM, preferably from about 0.5 μM to 5 μM, and preferably from 1 μM to about 2 μM.

In one embodiment, the fluorogenic chromophore has a formula (II), (III), (IV), (V), (VI), (VII) or (VIII):

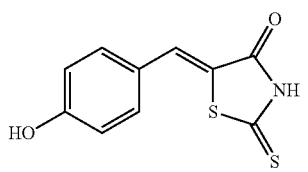

formula (II)

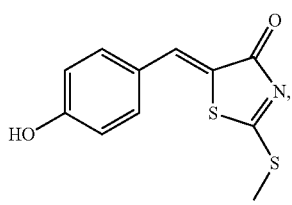

formula (III)

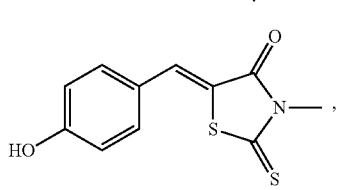

formula (IV)

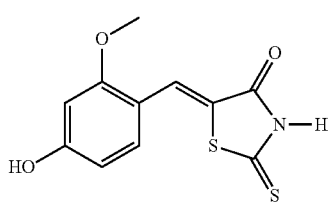

formula (V)

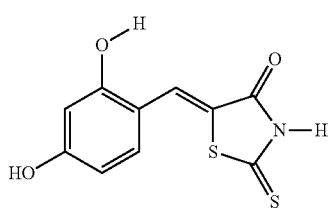

formula (VI)

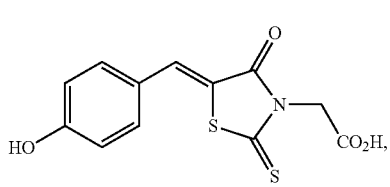

formula (VII)

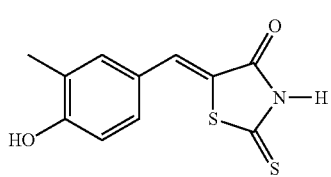

formula (VIII)

preferably said fluorogenic chromophore has a formula (II) (HBR) or a formula (VIII) (HMBR).

In a particular embodiment, the said polypeptide comprises or is a functional derivative of a PYP having a sequence selected from the group comprising SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80 or SEQ ID NO: 81, or a functional fragment thereof, preferably said polypeptide is a derivative of SEQ ID NO: 48.

In a particular embodiment, the said polypeptide comprises a functional PYP derivative, or a functional fragment thereof, comprising at least one amino acid substitution, addition or deletion in at least one of the amino acid regions 52-53, 65-69 and/or 94-101, with reference to SEQ ID NO: 48.

In a particular embodiment, the said polypeptide comprises a functional PYP derivative, or a functional fragment thereof, comprising at least one amino acid substitution, addition or deletion in the amino acid region 94-101, with reference to SEQ ID NO: 48.

In a particular embodiment, the said polypeptide comprises a functional PYP derivative, or a functional fragment thereof, comprising at least one of:
  a proline at position 97,
  a tryptophane at position 94,
  an amino acid residue with branched aliphatic side chain, preferably isoleucine, valine or leucine, at position 96, and/or
  a threonine at position 98,
with reference to SEQ ID NO: 48.

In a particular embodiment, the said polypeptide comprises a functional PYP derivative comprising an amino acid region 94-101 of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127 or SEQ ID NO: 128; with reference to SEQ ID NO: 48, preferably an amino acid region 94-101 of SEQ ID NO: 83 with reference to SEQ ID NO: 48.

In a particular embodiment, the said polypeptide comprises or consists in an amino acid sequence selected from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 or SEQ ID NO: 47, or a functional fragment thereof, preferably SEQ ID NO: 3 or a functional fragment thereof.

The present invention further concerns a fluorescent reporter comprising a polypeptide of the invention.

The present invention further relates to a fusion protein comprising a polypeptide as described hereinabove fused to a protein of interest.

The present invention further relates to the use of a polypeptide of the invention or the fusion protein of the invention for quantifying and/or detecting protein activity, protein localization, protein-protein interactions, and/or protein relocation in any solid or liquid sample, cell or tissues or organisms of interest.

The present invention further concerns the use of a fluorogenic chromophore having the formula (I):

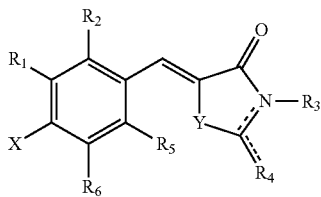

formula (I)

wherein
R1, R2, R3, R4, R5, R6, X and Y are as defined above, for reversibly coloring a particle, preferably a protein, or a surface.

In a particular embodiment, the said fluorogenic chromophore for the use of the invention has the formula (II):

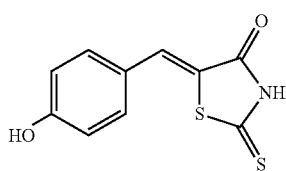

formula (II)

The present invention further concerns a complex formed by the polypeptide and the fluorogenic chromophore according to the invention.

The present invention further concerns a polynucleotide encoding the polypeptide according to the invention or the fusion protein of the invention.

The present invention further concerns a vector comprising the polynucleotide according to the invention.

The present invention further concerns a method for fluorescently labelling or coloring a surface or a particle, preferably a protein of interest, comprising the steps of (i) binding the polypeptide of the invention to the said surface or particle, and (ii) providing a fluorogenic chromophore, preferably a fluorogenic chromophore of the invention.

Another object of the invention is a method for sequentially labelling proteins (preferably in a cell), comprising the use of at least two polypeptides (preferably two PYP derivatives of the invention or two fusion proteins of the invention) binding to at least two fluorogenic chromophore with:
  a $K_D$ ranging from about 0.05 to about 10 μM when measured at a temperature of about 25° C., preferably ranging from about 0.1 to about 2 μM, more preferably ranging from about 0.13 to about 1.02 μM; and/or
  a $k_{off}$ ranging from about 1 to about 50 s$^{-1}$ when measured at a temperature of about 25° C., preferably from about 5 to about 20 s$^{-1}$, more preferably from about 6.3 to about 17 s$^{-1}$; and/or a $k_{on}$ ranging from about 0.1×10$^7$ to about 50×10$^7$ M$^{-1}$s$^{-1}$ when measured at a temperature of about 25° C., preferably from about 1×10$^7$ to about 10×10$^7$ M$^{-1}$s$^{-1}$, more preferably from about 3×10$^7$ to about 6.3×10$^7$ M$^{-1}$s$^{-1}$,
wherein the method of the invention comprises:
  contacting said sample with a first fluorogenic chromophore;
  measuring fluorescence;
  washing the sample to turn the fluorescence off;
  contacting said sample with a second fluorogenic chromophore;
  measuring fluorescence;
  washing the sample to turn the fluorescence off;
  repeating the previous steps with each fluorogenic chromophore.

Another object of the invention is a method of identifying PYP derivatives capable of binding to a fluorogenic chromophore with:
  a $K_D$ ranging from about 0.05 to about 10 μM when measured at a temperature of about 25° C., preferably ranging from about 0.1 to about 2 μM, more preferably ranging from about 0.13 to about 1.02 μM; and/or
  a $k_{off}$ ranging from about 1 to about 50 s$^{-1}$ when measured at a temperature of about 25° C., preferably from about 5 to about 20 s$^{-1}$, more preferably from about 6.3 to about 17 s$^{-1}$; and/or
  a $k_{on}$ ranging from about 0.1×10$^7$ to about 50×10$^7$ M$^{-1}$s$^{-1}$ when measured at a temperature of about 25° C., preferably from about 1×10$^7$ to about 10×10$^7$ M$^{-1}$s$^{-1}$, more preferably from about 3×10$^7$ to about 6.3×10$^7$ M$^{-1}$s$^{-1}$,
wherein said method comprises
  randomly mutating (such as, for example, by saturation mutagenesis) a PYP sequence (wherein the PYP sequence is selected from SEQ ID NO: 48-81, preferably SEQ ID NO: 48),
  measuring the kinetic constant of association of mutated PYP with the fluorogenic chromophore, and
  selecting mutated PYP with specified $K_D$, $k_{on}$ and/or $k_{off}$.

The present invention further relates to a fluorogenic chromophore having a formula (III) or (V):

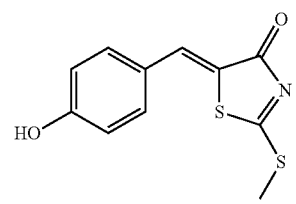

formula (II)

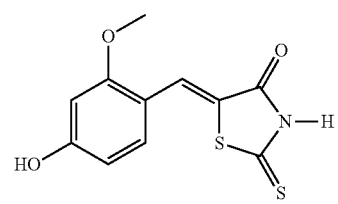

formula (V)

DEFINITIONS

As used herein, the term "derivative" of a protein may refer to a fragment or to a variant of said protein.

As used herein, the term "halo" means fluoro, chloro, bromo or iodo. Preferred halo groups are fluoro and chloro.

As used herein, the term "hydroxyl" refers to the —OH function.

As used herein, the term "aryl" refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6- tetralinyl, naphthalen-1- or -2-yl, 4-, 5-, 6 or 7-indenyl, 1-2-, 3-, 4- or 5- acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

As used herein, the term "alkyl" refers to a hydrocarbyl radical of formula $C_nH_{2n+1}$ wherein n is a number greater than or equal to 1. Generally, alkyl groups of this invention comprise from 1 to 12 carbon atoms, preferably from 1 to 6 carbon atoms. Alkyl groups may be linear or branched and may be substituted as indicated herein. Suitable alkyl groups include methyl, ethyl, propyl (n-propyl, i-propyl, n- butyl), butyl (i-butyl, s-butyl and t-butyl), pentyl and its isomers (e.g. n-pentyl, iso-pentyl), and hexyl and its isomers (e.g. n-hexyl, iso-hexyl).

As used herein, the term "cycloalkyl" refers to a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl.

As used herein, the term "heteroalkyl" refers to alkyl group having at least one atom that is not carbon or hydrogen; preferably, said atom is selected from N, S, P or 0.

As used herein, the term "heterocycloalkyl" refers to a cycloalkyl group having at least one atom that is not carbon or hydrogen; preferably, said atom is selected from N, S, P or O.

As used herein, the term "oxo" refers to the —C=O function.

As used herein, the term "nitro" refers to the —NO$_2$ function.

As used herein, the term "amido" refers to the —NR—CO— function wherein R may be —H or an alkyl group.

As used herein, the term "carboxy" refers to the —COOH function.

As used herein, the term "amino" refers to a —NH$_2$ group or any group derived thereof by substitution of one or two hydrogen atom by an organic aliphatic or aromatic group. Preferably, groups derived from —NH$_2$ are alkylamino groups, i.e. N-alkyl groups, comprising monoalkylamino and dialkylamino. According to a specific embodiment, the term "amino" refers to NH$_2$, NHMe or NMe$_2$.

As used herein, the term "cyano" refers to the —C≡N function.

As used herein, the term "haloalkoxy" refers to any alkoxy group substituted by one or more halo group.

As used herein, the term "alkoxy" refers to any O-alkyl group.

As used herein, the term "haloalkyl" refers to any alkyl group substituted by one or more halo group. Examples of preferred haloalkyl groups are CF$_3$, CHF$_2$ and CH$_2$F.

As used herein, the term "peptide" refers to a linear polymer of amino acids of less than 50 amino acids linked together by peptide bonds. Moreover, the terms "protein" and "polypeptide" may be used interchangeably, unless otherwise specified. In one embodiment, a "polypeptide" refers to a linear polymer of at least 50 amino acids linked together by peptide bonds; and a protein specifically refers to a functional entity formed of one or more peptides or polypeptides, and optionally of non-polypeptides cofactors.

As used herein, the term "about" preceding a figure means plus or less 10% of the value of said figure.

Within the context of the present invention, by "fluorogenic chromophore", it is meant a chromophore, the brightness of which can be significantly enhanced by an environmental change. The fluorogenic chromophore of the invention is substantially non-fluorescent in solution under its free form, but brightens up when placed into an environment constraining its conformation and excluding the non-fluorescent deexcitation of its excited state. In a particular embodiment of the invention, the free dye (i.e. the fluorogenic chromophore) is almost invisible in solution and becomes fluorescent upon binding of a protein scaffold which encases the said fluorogenic compound in a cavity of the protein.

By "fluorescence quantum yield", it is meant the ratio of the number of photons emitted to the number of photons absorbed by the fluorogenic chromophore.

By "fluorophore", it is meant a fluorescent chemical compound that can re-emit light upon light excitation.

DETAILED DESCRIPTION

This invention thus relates to polypeptide comprising a functional photoactive yellow protein (PYP) derivative or a functional fragment thereof,
wherein said polypeptide binds reversibly a fluorogenic chromophore with:
  a $K_D$ ranging from about 0.05 to about 10 µM when measured at a temperature of about 25° C., preferably ranging from about 0.1 to about 2 µM, more preferably ranging from about 0.13 to about 1.02 µM; and/or
  a $k_{off}$ ranging from about 1 to about 50 s$^{-1}$ when measured at a temperature of about 25° C., preferably from about 5 to about 20 s$^{-1}$, more preferably from about 6.3 to about 17 s$^{-1}$; and/or
  a $k_{on}$ ranging from about 0.1×10$^7$ to about 50×10$^7$ M$^{-1}$s$^{-1}$ when measured at a temperature of about 25° C., preferably from about 1×10$^7$ to about 10×10$^7$ M$^{-1}$s$^{-1}$, more preferably from about 3×10$^7$ to about 6.3×10$^7$ M$^{-1}$s$^{-1}$.

Methods for measuring $K_D$, $k_{on}$ and $k_{off}$ constants are well known in the art, and include, for example, those described by Scatchard et al. (Ann. N.Y. Acad. Sci. USA 51:660 (1949)). In one embodiment, $K_D$, $k_{on}$ and $k_{off}$ constants are determined using series of stopped-flowed experiments, such as, for example, as described in the Examples.

Advantageously, the polypeptide of the invention binds the fluorogenic chromophore reversibly, i.e. through non-covalent interactions.

Preferably, the polypeptide of the invention is a tag, which means that the polypeptide of the invention may be fused to a protein of interest, thereby allowing detection of the protein of interest.

The present invention further relates to an engineered fusion protein comprising a protein of interest fused to a polypeptide of the invention. In one embodiment, the polypeptide of the invention is fused in N-term of the protein of interest. In another embodiment, the polypeptide of the invention is fused in C-term of the protein of interest. In one embodiment, the polypeptide of the invention is fused to the protein of interest via a linker. Examples of linker that may be used are well known by the skilled artisan and include, without limitation, $(GGS)_n$, $(GGGS)_n$, or any $X_n$ sequence, wherein X is any amino acid and wherein n preferably ranges from 1 to 25.

In one embodiment, said polypeptide enhances the brightness of the said fluorogenic chromophore upon complexation thereto. Within the present invention, by "enhancing the brightness", it is meant that the fluorogenic chromophore of the invention, once complexed with the polypeptide of the invention or with any other suitable polypeptide, displays an exalted fluorescence. In a particular embodiment, the exalted fluorescence results from the encasing of the fluorogenic chromophore into a specific protein scaffold which prevents its non-fluorescent deexcitation from its excited state. In a particular embodiment, the brightness enhancement results from the stabilization of the phenolate form of the fluorogenic chromophore.

In a particular embodiment, the fluorescence quantum yield of the fluorogenic chromophore encased in a protein cavity of the invention ranges from 1% to 100%, preferably from about 1 to about 50%, and more preferably from about 6 to about 33%.

In another embodiment, the brightness of the polypeptide of the invention in presence of a fluorogenic chromophore ranges from about 2000 to about 20000 $M^{-1}cm^{-1}$, preferably from about 2500 to about 15000 $M^{-1}cm^{-1}$.

Advantageously, the fact that the free fluorogenic chromophore is almost invisible in solution avoids the need for washing, thereby allowing instant labelling of the object (preferably the protein of interest) tagged with the polypeptide of the invention in presence of the fluorogenic chromophore of the invention.

In another embodiment, said polypeptide induces the spectral shift of the said fluorogenic chromophore through the ionization of an auxochromic group thereof. Within the present invention, by "inducing the spectral shift", it is meant that the said polypeptide contains a distribution of charges or hydrogen bond network suitable for maintaining the specific ionization of the fluorogenic chromophore. As a result, the natural chromatic pattern of said fluorogenic chromophore is altered, due to a change in ionization state: the ionization of the auxochromic group of the fluorogenic chromophore thus results in a positive spectral shift corresponding to a bathochromic shift (also called "red shift"). Upon change of the ionization state, the absorption and/or the emission of the fluorogenic chromophore for use in the invention therefore shifts to the red. In a particular embodiment of the invention, the change of ionization state resulting in the induced spectral shift of the fluorogenic chromophore results from the specific binding thereof in the cavity of a protein scaffold, and more preferably in the cavity of an engineered PYP derivative of the invention, or a fragment thereof.

The induced spectral shift of the invention advantageously allows discriminating between the signal originating from the fluorogenic chromophore bound to the engineered protein of the invention from unspecific immobilization of the fluorogen by interfering cellular components. As the fluorogenic chromophore bound to the engineered protein scaffold absorbs in a wavelength range where the unbound or the non-specifically bound fluorogen does not absorb, it can specifically be excited by choosing the appropriate wavelength of excitation (see FIG. 1). The protein tag of the invention is thus called Fluorogen Activating and Shifting Tag (FAST), and in particular Y-FAST (for Yellow Fluorogen Activating and Shifting Tag).

In one embodiment, the spectral shift of the fluorogenic chromophore induced by the polypeptide of the invention is an at least 50 nm red shift, preferably an at least 60 nm red shift, and more preferably an about 70 nm red shift.

In another embodiment, said polypeptide binds said fluorogenic chromophore with a renewal time suitable for displaying an apparent photostability. Within the present invention, by "binding with a renewal time suitable for displaying an apparent photostability", it is meant that the polypeptide of the invention binds the fluorogenic chromophore with a good specificity but with an affinity that allows a continuous renewal of the fluorogenic chromophore bound within the cavity of the polypeptide of the invention. In a particular embodiment of the invention, the renewal time of the fluorogenic chromophore complexed with the polypeptide of the invention is of from about 1 ms to about 10 s, preferably from about 10 ms to about 1000 ms, and more preferably from about 50 ms to about 200 ms.

It therefore results that if the non-covalently bound fluorogenic chromophore is photo-destroyed by local illumination, a fresh one from the external reservoir that constitutes the solution will replace it, leading to an apparent photostable combination of the polypeptide of the invention and of the fluorogenic chromophore.

In a particular embodiment, the dissociation constant ($K_D$) of the polypeptide of the invention with the fluorogenic chromophores of the invention ranges from 10 nM to 25 µM, and is preferably comprised between about 0.1 µM and about 10 µM, preferably between about 0.1 µM to about 5 µM, preferably from about 0.1 µM to about 1 µM. In one embodiment, the dissociation constant ($K_D$) of the polypeptide of the invention with the fluorogenic chromophores of the invention ranges from about 1 µM to about 2 µM.

In a particular embodiment, the renewal time of the fluorogenic chromophore complexed with the polypeptide of the invention is of from 1 ms to 10 s when the concentration of the said fluorogenic chromophore in solution is substantially identical to the $K_D$ of the polypeptide of the invention. As a result, the polypeptide and the fluorogenic chromophore of the invention advantageously provide a solution to a long felt need in the art, since they allow surfaces and objects, more specifically proteins, to be labelled fluorescently in avoiding the photobleaching resulting from the photodamaging of usual fluorophores.

Preferably, said fluorogenic chromophore has a formula (I):

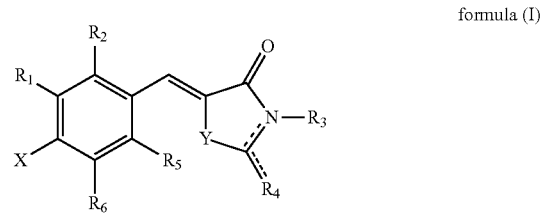

formula (I)

wherein

R1, R2, R5 and R6 may be identical or different and each represents H, halo, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl;

R3 represents a non-binding doublet (i.e. a free pair of electrons) or H, halo, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl;

R4 is a single or a double bound, interrupted or terminated by S, O or N atom, optionally substituted by at least one group selected from H, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl;

X is OH, SH, NHR7, or N(R7)$_2$, wherein R7 is H, halo, hydroxyl, aryl, alkyl, cycloalkyl, heteroalkyl or heterocycloalkyl group, saturated or unsaturated, linear or branched, optionally substituted by at least one group selected from halo, hydroxyl, oxo, nitro, amido, carboxy, amino, cyano, haloalkoxy, haloalkyl; and Y is O, NH or S;

In a particular embodiment, the fluorescence quantum yield of the acidic and/or basic forms of the fluorogenic chromophore in solution is lower than 0.5%, preferably lower than 0.3%, preferably lower than 0.1%, more preferably lower than 0.05%. Methods for measuring the fluorescence quantum yield are well known in the art.

In a particular embodiment, the fluorogenic chromophore that is bound by the polypeptide of the invention is selected in the group comprising the fluorogens of formula (II), (III), (IV), (V), (VI), (VII) or (VIII):

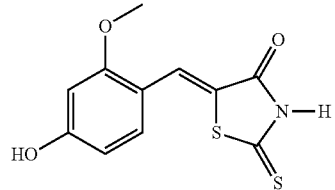

formula (II)

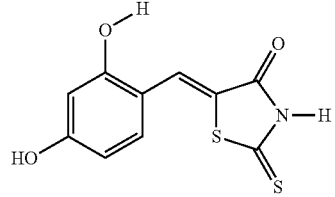

formula (III)

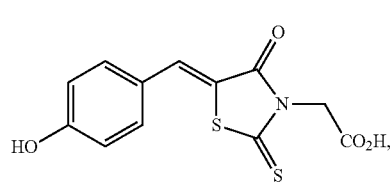

formula (IV)

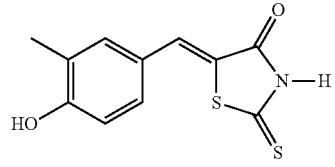

formula (V)

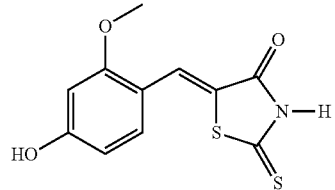

formula (V)

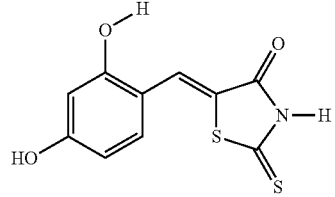

formula (VI)

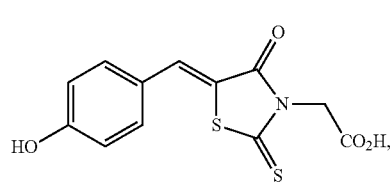

formula (VII)

and

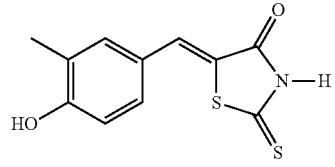

formula (VIII)

The present invention further relates to a fluorogen of formula (III) or (V):

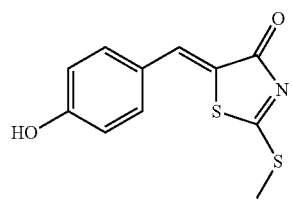

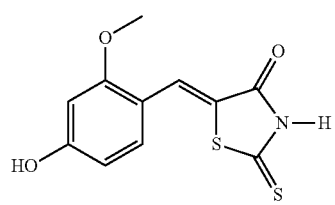

In an embodiment, the fluorogenic chromophore has the formula (II), and corresponds to the 4-hydroxybenzylidene-rhodanine or (Z)-5-(4-hydroxybenzylidene)-2-thioxo-1,3-thiazolidin-4-one (or HBR):

formula (II)

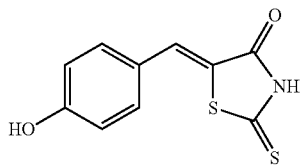

In a particular embodiment, HBR is prepared by the following method:

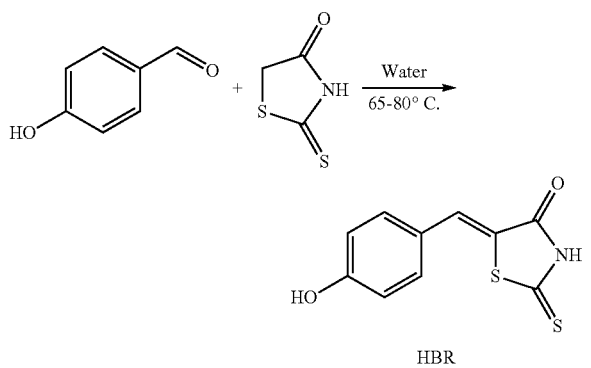

HBR

In another embodiment, the fluorogenic chromophore has the formula (IV), and corresponds to the (Z)-5-(4-hydroxybenzylidene)-3-methyl-2-thioxothiazolidin-4-one (or HBMR):

formula (IV)

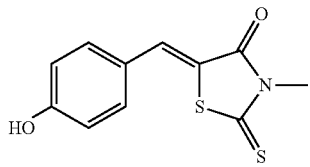

In another embodiment, the fluorogenic chromophore has the formula (VII), and corresponds to the (Z)-2-(5-(4-hydroxybenzylidene)-4-oxo-2-thioxothiazolidin-3-yl)acetic acid (or HBAAR):

formula (VII)

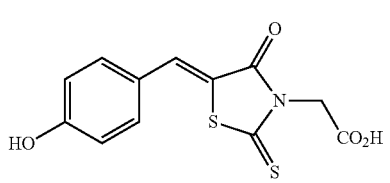

In another embodiment, the fluorogenic chromophore has the formula (VI), and corresponds to the (Z)-5-(2,4-Dihydroxybenzylidene)-2-thioxo-1,3-thiazolidin-4-one (or DHBR):

formula (VI)

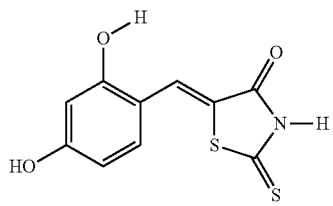

In another embodiment, the fluorogenic chromophore has the formula (V), and corresponds to the (Z)-5-(4-hydroxy-3-methoxybenzylidene)-2-thioxo-1,3-thiazolidin-4-one (or HMOBR):

formula (V)

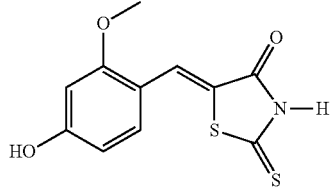

In another embodiment, the fluorogenic chromophore has the formula (VIII), and corresponds to the (Z)-5-(4-hydroxy-3-methylbenzylidene)-2-thioxo-1,3-thiazolidin-4-one (or HMBR).

formula (VIII)

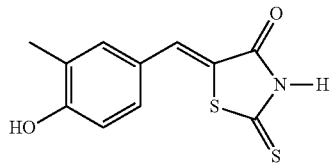

In one embodiment, HBMR, HBAAR, DHBR, HMOBR and HMBR are prepared by an equivalent method to the hereinabove method described for preparing HBR.

Preferably, the fluorogenic chromophore of the invention is HBR or HMBR.

In one embodiment, the fluorogenic chromophore is HBR, and the polypeptide of the invention binds reversibly HBR with:
- a $K_D$ ranging from about 0.1 to about 10 µM when measured at a temperature of about 25° C., preferably ranging from about 0.5 to about 2 µM, more preferably ranging from about 0.59 to about 1.02 µM; and/or
- a $k_{off}$ ranging from about 1 to about 50 s$^{-1}$ when measured at a temperature of about 25° C., preferably from about 5 to about 20 s$^{-1}$, more preferably from about 8 to about 17 s$^{-1}$; and/or
- a $k_{on}$ ranging from about 0.1×10$^7$ to about 50×10$^7$ M$^{-1}$s$^{-1}$ when measured at a temperature of about 25° C., preferably from about 1×10$^7$ to about 10×10$^7$ M$^{-1}$s$^{-1}$, more preferably of about 3×10$^7$ M$^{-1}$s$^{-1}$.

In another embodiment, the fluorogenic chromophore is HMBR, and the polypeptide of the invention binds reversibly HMBR with:
- a $K_D$ ranging from about 0.05 to about 10 µM when measured at a temperature of about 25° C., preferably ranging from about 0.1 to about 1 µM, more preferably of about 0.13 µM; and/or a $k_{off}$ ranging from about 1 to about 50 s$^{-1}$ when measured at a temperature of about 25° C., preferably from about 5 to about 10 s$^{-1}$, more preferably of about 6.3 s$^{-1}$; and/or a $k_{on}$ ranging from about 0.1×10$^7$ to about 50×10$^7$ M$^{-1}$s$^{-1}$ when measured at a temperature of about 25° C., preferably from about 5×10$^7$ to about 10×10$^7$ M$^{-1}$s$^{-1}$, more preferably of about 6.3×10$^7$ M$^{-1}$s$^{-1}$.

Within the present invention, by "Photoactive yellow protein" or "PYP", it is meant a photoreceptor protein isolated, for instance, from purple photosynthetic bacteria *Ectothiorhodospira halophila* (*Halorhodospira halophila*). The PYP is a relatively small protein (14 kDa), which may thus advantageously be used as a protein tag for labelling other proteins. In the wild-type PYP, a chromophore, formed by p-coumaric acid binds PYP to the 69$^{th}$ cysteine residue thereof through a thioester bond.

Within the present invention, by "functional PYP derivative", it is meant a PYP variant that has been tailored for accepting the above disclosed family of fluorogenic chromophores of the invention. The PYP derivative of the invention is in particular composed of an engineered protein scaffold that has the capacity of specifically and reversibly binding the said fluorogenic chromophore as defined above, with $K_D$, $k_{on}$ and/or $k_{off}$ as defined hereinabove.

These variants encompass, for example, a polypeptide that has the same activity as the aforementioned polypeptide and that comprises an amino acid sequence with, in the amino acid sequence of the aforementioned polypeptide, one or more deleted, substituted, inserted and/or added amino acids. Two or more different types of modifications selected from deletion, substitution, insertion, and addition may be carried out concurrently.

The PYP variant of the present invention also encompasses "partial peptides or polypeptides" of PYP. A partial peptide or polypeptide of PYP can be exemplified by a partial peptide or polypeptide comprising an amino acid sequence in which a portion of the amino acid sequence of PYP runs uninterrupted, wherein the partial peptide or polypeptide preferably has the same activity as said PYP. Such a partial peptide or polypeptide can be exemplified by an amino acid sequence comprising at least 20 and preferably at least 50 of the amino acid residues in the amino acid sequence of PYP. This peptide or polypeptide preferably contains the amino acid sequence that corresponds to the region that is involved with the activity of PYP. In addition, the partial peptide or polypeptide used in the present invention may also be a partial peptide or polypeptide as yielded by a modification of this peptide wherein 1 or a plurality of amino acid residues (for example, approximately 1 to 20, more preferably approximately 1 to 10, and even more preferably approximately 1 to 5) is deleted from, substituted in, inserted into, and/or added to its amino acid sequence. The partial peptide or polypeptide used in the present invention can also be used as an antigen for antibody production.

In one embodiment, a variant of PYP is an amino acid sequence comprising at least 8 contiguous amino acids, preferably of at least 10, 20 or at least 50, or at least 100, or at least 125 contiguous amino acids of PYP.

In another embodiment, a variant of PYP is a polypeptide having at least 70%, 75%, 80%, 90%, 95%, or at least 96%, 97%, 98%, 99% identity with the amino acid sequence of PYP.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Within the present invention, by "functional fragment", it is meant an incomplete PYP or an incomplete PYP derivative which has retained its ability to bind specifically and reversibly the above disclosed fluorogenic chromophores, with $K_D$, $k_{on}$ and/or $k_{off}$ as defined hereinabove. In one embodiment, said functional fragment is capable of enhancing the brightness and the spectral shift thereof, in accordance with the above discussed mechanisms.

In one embodiment of the invention, a fragment is an amino acid sequence of at least 8 amino acids (preferably contiguous amino acids), preferably of at least 10, 15, 20, 25, 30, 40, 50, 60, 70, 80, 90, 100, 110, 120 amino acids (preferably contiguous amino acids).

In one embodiment of the invention, a fragment of PYP or of a variant thereof comprises amino acids 70-125, 80-120, 90-110 or 94-101 (wherein the numbering of the amino acid sequences is made by reference to the sequence of SEQ ID NO: 48).

In another embodiment, a fragment of PYP or of a variant thereof comprises amino acids 1-101, 10-101, 20-101, 30-101, 40-101, 50-101, 60-101, 70-101, 80-101, 90-101, 90-110, 90-120 or 90-125 (wherein the numbering of the amino acid sequences is made by reference to the sequence of SEQ ID NO: 48).

In a particular embodiment of the present invention, the polypeptide according to the present invention comprises a functional derivative of a PYP from a species selected from the group consisting of *Halorhodospira halophila, Halomonas boliviensis* LC1, *Halomonas* sp. FAJ-1, *Rheinheimera* sp. A13L, *Iodomarina loihiensis, Thiorhodospira sibirica* ATCC 700588, *Rhodothalassium salexigens, Roseomonas cervicalis* ATCC 49957, *Rhodobacter sphaeroides, Leptospira wolbachii, Rhodobacter capsulatus, Rhodospirillum centenum, Leptospira vanthielii, Leptospira terpstrae, Leptospira biflexa* serovar Patoc strain 'Patoc 1 (Paris)', *Lep-* tospira meyeri, Leptospira yanagawae, Salinibacter ruber DSM 13855, Burkholderia phytofirmans PsJN, Phaeospirillum fulvum, Acidithiobacillus thiooxidans, Acidithiobacillus caldus SM-1, Gammaproteobacterium NORS-3, Methylotenera versatilis 301, Leptothrix cholodnii SP-6, Caenispirillum salinarum, Stigmatella aurantiaca DW4/3-1, Massilia timonae, Methyloversatilis universalis FAM 5, Spirosoma linguale DSM 74, Rhodopseudomonas palstris BisB5, Sorangium cellulosum 'So ce 56' or Rhodomicrobium vannielii ATCC 17100.

In a particular embodiment, the polypeptide of the invention comprises a functional derivative or a functional fragment of a PYP having a sequence selected from the group consisting of SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80 and SEQ ID NO: 81.

In a particular embodiment, the polypeptide of the invention comprises a functional derivative from a PYP having the sequence of SEQ ID NO: 48, corresponding to the C69G sequence of the PYP of Halorhodospira halophila.

In a particular embodiment of the invention, the polypeptide of the invention comprises a functional derivative from a PYP selected in the group consisting of SEQ ID NO: 48-81, or a functional fragment thereof, wherein at least one, preferably at least two, preferably at least three, preferably at least four, preferably at least five, preferably at least six, preferably at least seven, preferably all amino acid have been deleted, substituted or added in at least one, two or all of the amino acid sequences 52-53, 65-69 and/or 94-101 (wherein the numbering of the amino acid sequences is made by reference to the sequence of SEQ ID NO: 48).

Amino acids 52-53 in SEQ ID NO: 48 corresponds to amino acids 52-53 in SEQ ID NO: 49-55, 68, 70, 72 and 79; to amino acids 51-52 in SEQ ID NO: 56, 57, 59, and 77; to amino acids 45-46 in SEQ ID NO: 60; to amino acids 49-50 in SEQ ID NO: 66, 73, 74, 76, 78 and 81; to amino acids 53-54 in SEQ ID NO: 75; to amino acids 41-42 in SEQ ID NO: 58 and 61; to amino acids 47-48 in SEQ ID NO: 62-65 and 69; to amino acids 38-39 in SEQ ID NO: 67; to amino acids 39-40 in SEQ ID NO: 71; and to amino acids 35-36 in SEQ ID NO: 80.

Amino acids 65-69 in SEQ ID NO: 48 corresponds to amino acids 65-69 in SEQ ID NO: 49-55, 68, 70, 72 and 79; to amino acids 64-68 in SEQ ID NO: 56, 57, 59, and 77; to amino acids 58-62 in SEQ ID NO: 60; to amino acids 62-66 in SEQ ID NO: 66, 73, 74, 76, 78 and 81; to amino acids 66-70 in SEQ ID NO: 75; to amino acids 54-58 in SEQ ID NO: 58 and 61; to amino acids 60-64 in SEQ ID NO: 62-65 and 69; to amino acids 51-55 in SEQ ID NO: 67; to amino acids 52-56 in SEQ ID NO: 71; and to amino acids 48-52 in SEQ ID NO: 80.

Amino acids 94-101 in SEQ ID NO: 48 corresponds to amino acids 94-101 in SEQ ID NO: 49-55, 70, 77 and 79; to amino acids 94-99 in SEQ ID NO: 68; to amino acids 93-100 in SEQ ID NO: 56, 57, and 59; to amino acids 92-99 in SEQ ID NO: 73 and 76; to amino acids 89-96 in SEQ ID NO: 62-65 and 69; to amino acids 95-102 in SEQ ID NO: 72 and 75; to amino acids 90-97 in SEQ ID NO: 74; to amino acids 91-98 in SEQ ID NO: 66 and 81; to amino acids 83-90 in SEQ ID NO: 58 and 61; to amino acids 87-94 in SEQ ID NO: 60 and 78; to amino acids 77-84 in SEQ ID NO: 67 and 80; and to amino acids 78-85 in SEQ ID NO: 71.

In a further particular embodiment, the polypeptide comprises a functional derivative from a PYP selected in the group consisting of SEQ ID NO: 48-81, or a fragment thereof, wherein at least one, preferably at least two, preferably at least three, preferably at least four, preferably at least five, preferably at least six, preferably at least seven, preferably all amino acid have been deleted, substituted or added in the amino acid sequence 94-101, by reference to the sequence of SEQ ID NO: 48.

In a particular embodiment, the polypeptide of the invention comprises a functional derivative from a PYP selected in the group consisting of SEQ ID NO: 48-81, or a functional fragment thereof, comprising at least one, preferably at least two, preferably at least three, preferably at least four, preferably all of the modifications selected in the group consisting of:
  an amino acid substitution by a proline at position 97,
  an amino acid substitution by a tryptophane at position 94,
  an amino acid substitution by an amino acid residue with branched aliphatic side chain, preferably isoleucine, valine or leucine, at position 96, and/or
  an amino acid substitution by a threonine at position 98,
wherein the numbering of the amino acid sequences is made by reference to the sequence of SEQ ID NO: 48.

Amino acid 94 in SEQ ID NO: 48 corresponds to amino acid 94 in SEQ ID NO: 49, 50-55, 68, 70, 77 and 79; to amino acid 93 in SEQ ID NO: 56, 57, and 59; to amino acid 92 in SEQ ID NO: 73 and 76; to amino acid 89 in SEQ ID NO: 62-65 and 69; to amino acid 95 in SEQ ID NO: 72 and 75; to amino acid 90 in SEQ ID NO: 74; to amino acid 91 in SEQ ID NO: 66 and 81; to amino acid 83 in SEQ ID NO: 58 and 61; to amino acid 87 in SEQ ID NO: 60 and 78; to amino acid 77 in SEQ ID NO: 67 and 80; and to amino acid 78 in SEQ ID NO: 71.

Amino acid 96 in SEQ ID NO: 48 corresponds to amino acid 96 in SEQ ID NO: 49, 50-55, 68, 70, 77 and 79; to amino acid 95 in SEQ ID NO: 56, 57, and 59; to amino acid 94 in SEQ ID NO: 73 and 76; to amino acid 91 in SEQ ID NO: 62-65 and 69; to amino acid 97 in SEQ ID NO: 72 and 75; to amino acid 92 in SEQ ID NO: 74; to amino acid 93 in SEQ ID NO: 66 and 81; to amino acid 85 in SEQ ID NO: 58 and 61; to amino acid 89 in SEQ ID NO: 60 and 78; to amino acid 79 in SEQ ID NO: 67 and 80; and to amino acid 80 in SEQ ID NO: 71.

Amino acid 97 in SEQ ID NO: 48 corresponds to amino acid 97 in SEQ ID NO: 49, 50-55, 68, 70, 77 and 79; to amino acid 96 in SEQ ID NO: 56, 57, and 59; to amino acid 95 in SEQ ID NO: 73 and 76; to amino acid 92 in SEQ ID NO: 62-65 and 69; to amino acid 98 in SEQ ID NO: 72 and 75; to amino acid 93 in SEQ ID NO: 74; to amino acid 94 in SEQ ID NO: 66 and 81; to amino acid 86 in SEQ ID NO: 58 and 61; to amino acid 90 in SEQ ID NO: 60 and 78; to amino acid 80 in SEQ ID NO: 67 and 80; and to amino acid 91 in SEQ ID NO: 71.

Amino acid 98 in SEQ ID NO: 48 corresponds to amino acid 98 in SEQ ID NO: 49, 50-55, 68, 70, 77 and 79; to amino acid 97 in SEQ ID NO: 56, 57, and 59; to amino acid 96 in SEQ ID NO: 73 and 76; to amino acid 93 in SEQ ID NO: 62-65 and 69; to amino acid 99 in SEQ ID NO: 72 and 75; to amino acid 94 in SEQ ID NO: 74; to amino acid 95 in SEQ ID NO: 66 and 81; to amino acid 87 in SEQ ID NO: 58 and 61; to amino acid 91 in SEQ ID NO: 60 and 78; to amino acid 81 in SEQ ID NO: 67 and 80; and to amino acid 82 in SEQ ID NO: 71.

In one embodiment, the polypeptide of the invention comprises a functional derivative of a PYP having an amino acid sequence 94-101, by reference to the sequence of SEQ ID NO: 48, having the following sequence: WX$_1$IPTX$_2$X$_3$X$_4$ (SEQ ID NO: 129), wherein X$_1$, X$_2$, X$_3$ and X$_4$ each independently are any amino acid.

In a particular embodiment, the polypeptide of the invention comprises a functional derivative or fragment of a PYP having an amino acid sequence 94-101, by reference to the sequence of SEQ ID NO: 48, selected in the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127 or SEQ ID NO: 128.

In a particular embodiment, the polypeptide of the invention comprises or consists in a sequence selected in the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 or SEQ ID NO: 47, or a functional fragment thereof. Preferably, the polypeptide of the invention comprises or consists in SEQ ID NO: 3.

In one embodiment, the polypeptide of the invention comprises a sequence as described hereinabove, in particular a sequence selected from SEQ ID NO: 1 to SEQ ID NO: 47, wherein a circular (or cyclic) permutation has been carried out, i.e the order of the amino acids have been changed in the amino acid sequence, without impacting the three-dimensional structure of the polypeptide of the invention.

In one embodiment, the polypeptide of the invention comprises the following regions: C-term of a sequence selected from SEQ ID NO: 1 to SEQ ID NO: 47—optional linker —N-term of a sequence selected from SEQ ID NO: 1 to SEQ ID NO: 47.

In one embodiment, the polypeptide of the invention comprises (from N-term to C-term): a first methionine—amino acids 115 to 125 of SEQ ID NO: 1 (or any equivalent region in SEQ ID NO: 2 to 47)—an optional linker—amino acids 2 to 114 of SEQ ID NO: 1 (or any equivalent region in SEQ ID NO: 2 to 47).

In one embodiment, the polypeptide of the invention is monomeric, i.e. the polypeptide of the invention is encoded as a unique amino acid sequence. In another embodiment, the polypeptide of the invention is multimeric, in particular heteromultimeric (such as, for example, it comprises two monomers), wherein each of the monomer is independently expressed, and monomers interact together so as to form the polypeptide of the invention. In other words, in one embodiment, the three dimensional structure of the polypeptide of the invention results from the folding of a single amino acid chain, whereas in another embodiment, the three dimensional structure of the polypeptide of the invention results from the independent folding of at least two amino acid chain and from the interaction thereof.

The invention further concerns a polynucleotide encoding a polypeptide of the invention, as defined above. Another object of the invention is a vector comprising a polynucleotide of the invention.

In a particular embodiment, the polypeptide of the invention is further fused to a protein of interest, thereby constituting the engineered protein of the invention. Proteins of interest to be fused to the PYP derivative of the invention comprise any polypeptide of interest allowing to monitor any one of protein or enzyme activities, analyte concentrations, protein-protein interactions and membrane potential.

In a particular embodiment, the polypeptide of the invention may in particular be used for quantifying and/or detecting protein activity, protein localization, protein-protein interactions, and/or protein relocation in any solid or liquid sample, as well as in any cell or tissues or organisms of interest using fluorescence as readout.

In a particular embodiment, the polypeptide of the invention can be used for structural studies based on (i) protein labeling to study protein localization, protein motility and protein turnover; (ii) organelle labeling to study organelle structure, organelle fusion, organelle fission or organelle turnover; (iii) cell labeling to study cell morphology and to track cell movement; (iv) organism labeling for whole body imaging and transgenics detection.

In a particular embodiment, the polypeptide of the invention can be used for designing functional assays, including (i) assays to study activation, inhibition or co-activation of target promoters; (ii) assays for drug design based on promoter activation, protein turnover or optical biosensors.

In a particular embodiment, the polypeptide of the invention may be used in vitro and/or in vivo for biological research, including molecular biology, cell biology, developmental biology, neurobiology, immunology and physiology. The detection of the tagged protein of interest may be performed by any method enabling fluorescence quantification known in the art, including epifluorescence microscopy, confocal microscopy, super-resolution microscopy, spectrofluorimetry, Fluorescence correlation spectroscopy, and flow cytometry.

In a particular embodiment, the polypeptide of the invention can be expressed in fusion with any protein of interest within the cell or host organism of interest by inserting (via transformation, transfection . . . ) a polynucleotide according to the invention which encodes the chimeric engineered polypeptide of the invention.

In a particular embodiment the polypeptide of the invention can be immobilized onto a surface, including particle, oil droplet, polymer scaffold, bead, chip, plate, slide, sheet, film, fibers, medical device, surgical instrument, implant, biological tissues, or other structure. Such functionalized surfaces could be used to design traceable objects for applications in nanotechnology (e.g. nanoparticle detection), biomedical sciences (e.g. surgical implant).

In a particular embodiment, the polypeptide of the invention may be used for reversible coloring and fluorescence emission of various types of surfaces, including particle, oil droplet, polymer scaffold, bead, chip, plate, slide, sheet, film, paper, hairs, skin, textile fibers, medical device, surgical instrument, implant, biological tissues, or other structures. In a particular embodiment, in the context of reversible tattooing, such functionalized surfaces could be used to reliably but transiently labeling or decorating surfaces.

In a particular embodiment, the polypeptide of the invention may be used for latent printing on various types of surfaces, including particle, oil droplet, polymer scaffold, bead, chip, plate, slide, sheet, film, paper, textile fibers, medical device, surgical instrument, implant, biological tissues, or other structures. In a particular embodiment, in the context of security printing, such functionalized surfaces could be used to latently encoding information revealed with an appropriate ink.

The present invention further relates to the use of a polypeptide of the invention for use in FRET experiments. In one embodiment, the polypeptide of the invention plays the acceptor in a pair with a donor such as, for example, CFP. In another embodiment, the polypeptide of the invention plays the donor in a pair with an acceptor, such as, for example, mCherry.

The present invention further concerns the use of a fluorogenic chromophore of formula (I) as hereinabove described for reversibly coloring a particle or a surface.

In a particular embodiment, the present invention concerns the use of a fluorogenic chromophore of formula (II), (III), (IV), (V), (VI), (VII) or (VIII) as described hereinabove for reversibly coloring a particle or a surface.

In a particular embodiment, the present invention concerns the use of a fluorogenic chromophore of formula (II) (HBR) for reversibly coloring a particle or a surface.

In a particular embodiment, the present invention concerns the use of a fluorogenic chromophore of formula (VIII) (HMBR) for reversibly coloring a particle or a surface.

In a particular embodiment of the present invention, the said fluorogenic chromophore is used for coloring reversibly a protein of interest.

In a particular embodiment of the invention, the recited use of the fluorogenic chromophore further comprises the use of a polypeptide capable of binding reversibly the fluorogenic chromophore, further capable of enhancing the brightness of the said fluorogenic chromophore through the motion restriction thereof, and capable of inducing the spectral shift of the said fluorogenic chromophore through the ionization of an auxochromic group thereof.

In a particular embodiment, the recited use further comprises the presence of a polypeptide of the invention.

The invention further concerns a complex formed by a polypeptide according to the invention with a fluorogenic chromophore according to the invention.

The present invention finally concerns a method for fluorescently labelling or coloring a surface or a particle, preferably a protein, comprising the steps of binding a polypeptide of the invention to the surface or particle and providing a fluorogenic chromophore of the invention.

The present invention further relates to a method of identifying PYP derivatives capable of binding to a fluorogenic chromophore with:
a $K_D$ ranging from about 0.05 to about 10 μM when measured at a temperature of about 25° C., preferably ranging from about 0.1 to about 2 μM, more preferably ranging from about 0.13 to about 1.02 μM; and/or
a $k_{off}$ ranging from about 1 to about 50 s$^{-1}$ when measured at a temperature of about 25° C., preferably from about 5 to about 20 s$^{-1}$, more preferably from about 6.3 to about 17 s$^{-1}$; and/or
a $k_{on}$ ranging from about $0.1 \times 10^7$ to about $50 \times 10^7$ M$^{-1}$s$^{-1}$ when measured at a temperature of about 25° C., preferably from about $1 \times 10^7$ to about $10 \times 10^7$ M$^{-1}$s$^{-1}$, more preferably from about $3 \times 10^7$ to about $6.3 \times 10^7$ M$^{-1}$s$^{-1}$,
wherein said method comprises
randomly mutating (such as, for example, by saturation mutagenesis) a PYP sequence (wherein the PYP sequence is selected from SEQ ID NO: 48-81, preferably SEQ ID NO: 48),
measuring the kinetic constant of association of mutated PYP with the fluorogenic chromophore, and
selecting mutated PYP with $K_D$, $k_{on}$ and/or $k_{off}$ as described hereinabove.

The present invention further relates to a method for sequentially labelling proteins (preferably in a cell), comprising the use of at least two polypeptides (preferably two PYP derivatives as hereinabove described) binding to at least two fluorogenic chromophore with:
a $K_D$ ranging from about 0.05 to about 10 μM when measured at a temperature of about 25° C., preferably ranging from about 0.1 to about 2 μM, more preferably ranging from about 0.13 to about 1.02 μM; and/or
a $k_{off}$ ranging from about 1 to about 50 s$^{-1}$ when measured at a temperature of about 25° C., preferably from about 5 to about 20 s$^{-1}$, more preferably from about 6.3 to about 17 s$^{-1}$; and/or
a $k_{on}$ ranging from about $0.1 \times 10^7$ to about $50 \times 10^7$ M$^{-1}$s$^{-1}$ when measured at a temperature of about 25° C., preferably from about $1 \times 10^7$ to about $10 \times 10^7$ M$^{-1}$s$^{-1}$, more preferably from about $3 \times 10^7$ to about $6.3 \times 10^7$ M$^{-1}$s$^{-1}$,
wherein the method of the invention comprises:
contacting said sample with a first fluorogenic chromophore;
measuring fluorescence;
washing the sample to turn the fluorescence off;
contacting said sample with a second fluorogenic chromophore;
measuring fluorescence;
washing the sample to turn the fluorescence off;
repeating the previous steps with each fluorogenic chromophore.

The present invention further relates to a method for sequentially labelling proteins (preferably in a cell), comprising the use of at least one polypeptide (preferably two PYP derivatives as hereinabove described) binding to at least two fluorogenic chromophore with:
a $K_D$ ranging from about 0.05 to about 10 μM when measured at a temperature of about 25° C., preferably ranging from about 0.1 to about 2 μM, more preferably ranging from about 0.13 to about 1.02 μM; and/or
a $k_{off}$ ranging from about 1 to about 50 s$^{-1}$ when measured at a temperature of about 25° C., preferably from about 5 to about 20 s$^{-1}$, more preferably from about 6.3 to about 17 s$^{-1}$; and/or
a $k_{on}$ ranging from about $0.1 \times 10^7$ to about $50 \times 10^7$ M$^{-1}$s$^{-1}$ when measured at a temperature of about 25° C., preferably from about $1 \times 10^7$ to about $10 \times 10^7$ M$^{-1}$s$^{-1}$, more preferably from about $3 \times 10^7$ to about $6.3 \times 10^7$ M$^{-1}$s$^{-1}$,
and of at least one photoswitchable polypeptide (such as, for example, Dronpa)
wherein the method of the invention comprises:
visualizing the photoswitchable polypeptide;
measuring fluorescence;
switching off the photoswitchable polypeptide;

contacting said sample with a fluorogenic chromophore;
measuring fluorescence;
washing the sample to turn the fluorescence off;
repeating the previous steps with each fluorogenic chromophore and/or with each photoswitchable polypeptide.

In one embodiment, the sample comprises engineered proteins, wherein said engineered proteins are fusion proteins between a protein of interest to be labelled and a polypeptide binding to a fluorogenic chromophore as hereinabove described.

In one embodiment, washing steps are sub-minute washing steps, such as, for example, with a duration of about 10 sec, 20 sec, 30 sec, 40 sec, 50 sec or 60 sec.

The protein tag of the present invention thus presents the following advantages:
  the yellow fluorescence can be turned on and off at will by addition or withdrawal of the fluorogenic ligand;
  the absorption red shift enables to distinguish free and bound fluorogen via the choice of the excitation wavelength, thus increasing specificity;
  it enables efficient labeling of proteins in various hosts from microorganisms to mammalian cells and zebrafish embryos;
  it enables to monitor rapid processes (such as, for example, protein synthesis) in near real-time; and
  it may be used for multiplexing experiments.

BRIEF DESCRIPTION OF THE DRAWINGS

FIG. 14A-C show the absorption (14A) and fluorescence (14B-C) spectra of HMBR±Y-FAST (14A-B), and Y-FAST with HBR and HMBR (14C). HBR, HMBR and Y-FAST were respectively at 2 µM, 2 µM and 40 µM in PBS pH 7.4 at 25° C.

FIG. 15A to F are a set of graphs and images showing an analysis of the specificity of labeling of Y-FAST in yeast (15A, C, D) and bacteria (15B, E, F) with HBR and HMBR by flow cytometry (15A-B) and confocal microscopy (15C-F).

(FIG. 18A-B display the comparison of the fluorescence brightness of EGFP, UnaG, Y-FAST (labeled with 5 μM HMBR) and Venus expressed in HeLa cells upon excitation at 488 nm. FIG. 18A shows the confocal micrographs of representative cells (Ex/Em 488/493-797 nm; scale bars 10 μm). Side-by-side images were recorded using the same settings for direct comparison of the fluorescence intensities. FIG. 18B displays the quantification of the fluorescence brightness of the different proteins (n=15-30 cells).

FIGS. 19A, B, C and D are a set of images showing that Y-FAST enables specific labeling of fusion proteins in various subcellular locations. FIG. 19A-C show the confocal micrographs of live HeLa cells expressing Y-FAST (labeled with 5 μM HMBR) fused to (19A) a nuclear localization signal (NLS), (19B) a membrane targeting sequence (Lyn11), and (19C) the microtubule-binding protein Ensconsin. Images of cells expressing Dronpa-based constructs are shown as comparison (Ex/Em 488/493-797 nm).

FIG. 20A: mCherry fused to Y-FAST was expressed in vitro in the cell-free PURE system in presence of 20 μM HBR at 25° C.

FIG. 21A-B: HeLa cells expressing mCherry-Y-FAST were grown in a microfluidic channel and repeatedly incubated with HMBR-containing culture medium for 20 s and HMBR-free culture medium for 40 s. A multifunctional fluidic controller enabled several cycles of labeling/unlabeling. HMBR concentration was 5 μM. FIG. 21A shows the confocal timelapse showing two cycles of labeling/unlabeling (Ex/Em 488/493-575 nm). FIG. 21B shows the temporal evolution of the cell fluorescence upon addition (+) and removal (−) of HMBR.

EXAMPLES

Figure 1:
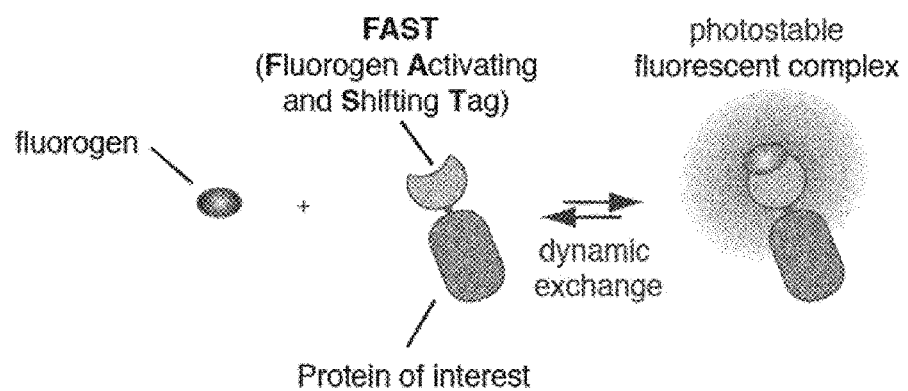
FIG. 1 is a drawing showing the general mechanism of FAST (Fluorogen Activating and Shifting Tag), as well as its use for fluorescently labelling proteins of interest in avoiding the standard issues of photobleaching. The disclosed fluorogen corresponds to the fluorogenic chromophore of the invention, and the disclosed fluorogen activating and shifting protein tag fused to the protein of interest corresponds to the polypeptide of the invention.

The present invention is further illustrated by the following examples.

Material and Methods

Measurement of the Thermokinetic Properties of the Fluorogen/Protein Complexes

The Model

Considering that the fluorogen and the polypeptide interact to provide a fluorescent complex, we adopted a two-state model to analyze the thermodynamics and the kinetics of the interaction. Denoting the fluorogen, the polypeptide and the complex respectively A, B, and AB, the interaction $$A + B \underset{k_{off}}{\overset{k_{on}}{\rightleftharpoons}} AB \tag{1}$$

is characterized by the rate constants $k_{on}$ and $k_{off}$ associated to the forward and backward reactions respectively, and the association thermodynamic constant K (=1/$K_D$) equal to the ratio $k_{on}/k_{off}$.

Calculation of the Equilibrium State

Denoting $A_{tot}$ and $B_{tot}$ the total concentrations of A and B, the concentrations $A_{fin}$, $B_{fin}$, and $AB_{fin}$ of the three species A, B, and AB at equilibrium are $$AB_{fin} = \frac{[K(A_{tot} + B_{tot}) + 1] - \sqrt{[K(A_{tot} + B_{tot}) + 1]^2 - 4K^2 A_{tot} B_{tot}}}{2K} \tag{2}$$

$$A_{fin} = A_{tot} - AB_{fin} \tag{3}$$

$$B_{fin} = B_{tot} - AB_{fin} \tag{4}$$

When $A_{tot} \gg B_{tot}$ as in the present series of experiments, the expressions (2-4) become $$AB_{fin} = \frac{KA_{tot}}{KA_{tot}+1} B_{tot} \quad (5)$$

$$A_{fin} = A_{tot} \quad (6)$$

$$B_{fin} = \frac{1}{KA_{tot}+1} B_{tot} \quad (7)$$

Measurement of the Association Constant K

The experimental observable is the fluorescence emission. Neglecting the brightness of the empty polypeptide B, the fluorescence intensity $I_F$ results from the contributions of the fluorogen A and its complex AB with respective brightnesses $Q_A$ and $Q_{AB}$ such that:

$$I_F = Q_A A + Q_{AB} AB \quad (8)$$

The thermodynamic constant K was determined by analyzing the dependence of the fluorescence intensity $I_F$ on the total concentration of the fluorogen $A_{tot}$ at constant concentration of the protein $B_{tot}$. We first extracted the bound fraction equal to $AB_{fin}/B_{tot}$ by (i) correcting $I_F(A_{tot})$ from the free fluorogen contribution ($Q_A A_{tot}$) and (ii) dividing the resulting corrected fluorescence intensity $I_{F,corr}(A_{tot})$ by its upper value $I_{F,corr}^\infty$ at large enough $A_{tot}$ concentrations such that $AB_{fin} = B_{tot}$. We subsequently fitted the dependence of the bound fraction on $A_{tot}$ with Eq.(9) derived from Eq.(8) to retrieve K.

$$\frac{AB_{fin}}{B_{tot}} = \frac{I_{F,corr}(A_{tot})}{I_{F,corr}^\infty} = \frac{I_F - Q_A A_{tot}}{I_{F,corr}^\infty} = \frac{KA_{tot}}{KA_{tot}+1} \quad (9)$$

Dependence on Temperature of the Association Constant K

The association constant K for HBR and HMBR was determined at different temperatures in the 25-45° C. range in order to obtained the enthalpy $\Delta H^\circ$ and the entropy $\Delta S^\circ$ associated to the reaction (1). Note that we verified by circular dichroism, that Y-FAST was stable in the considered temperature range in order to ascertain that our two-state model was valid for the subsequent analyses.

We extracted the enthalpy $\Delta H^\circ$ and the entropy $\Delta S^\circ$ associated to the reaction (1) from the linear dependence of lnK on 1/T given in Eq.(10), which has been derived upon assuming that $\Delta H^\circ$ and $\Delta S^\circ$ do not depend on temperature in the considered temperature range $$\ln K(T) = -\frac{\Delta H^\circ}{RT} + \frac{\Delta S^\circ}{R} \quad (10)$$

Calculation of the Temporal Evolution of the Concentrations

We next extracted the rate constants $k_{on}$ and $k_{off}$ from the temporal evolution of the concentrations A, B, and AB of the three species A, B, and AB using stopped-flow experiments. Considering that the two feeding syringes respectively contain A and B such that their respective initial concentrations in the cuvette after fast mixing are $A_{tot}$ and $B_{tot}$, the instantaneous concentrations of A, B, and AB in the cuvette, A, B, and AB, monotonously evolve towards the equilibrium concentrations $A_{fin}$, $B_{fin}$, and $AB_{fin}$ which are given by the expressions (2-4).

The differential equation governing the temporal evolution of the concentrations A, B, and AB is $$-\frac{dA}{dt} = -\frac{dB}{dt} = \frac{dAB}{dt} = k_{on} A \times B - k_{off} AB \quad (11)$$

Following a development previously reported (Bourdoncle et al, J Am Chem Soc 128, 11094-11105, 2006), we obtained $$AB = AB_{fin} \left\{ 1 - \frac{\exp\left(-\frac{t}{\tau}\right)}{1 + AB_{fin} k_{on} \tau \left[1 - \exp\left(-\frac{t}{\tau}\right)\right]} \right\} \quad (12)$$

$$A = A_{tot} - AB \quad (13)$$

$$B = B_{tot} - AB \quad (14)$$

with $$\tau = \frac{1}{k_{on}(A_{fin} + B_{fin}) + k_{off}} \quad (15)$$

Measurement of the Rate Constants $k_{on}$ and $k_{off}$

Extraction of the rate constants $k_{on}$ and $k_{off}$ at a given temperature has been performed by analyzing the temporal dependence of the fluorescence intensity in a series of stopped-flow experiments. We first derived Eq.(16) from Eqs.(8, 12, 13).

$$I_F(t) = Q_A A_{tot} + (Q_{AB} - Q_A) AB_{fin} \left\{ 1 - \frac{\exp\left(-\frac{t}{\tau}\right)}{1 + AB_{fin} k_{on} \tau \left[1 - \exp\left(-\frac{t}{\tau}\right)\right]} \right\} \quad (16)$$

Upon noting after preliminary fits and simulations that $AB_{fin} k_{on} \tau \ll 1$, we could further simplify the fitting equation and eventually adopted Eq.(17) to extract the relaxation time $\tau$.

$$I_F(t) = Q_A A_{tot} + (Q_{AB} - Q_A) AB_{fin} \left\{ 1 - \exp\left(-\frac{t}{\tau}\right) \right\} \quad (17)$$

Above 25° C., the relaxation time $\tau$ was found below the temporal resolution of our stopped-flow instrument under the relevant conditions of initial concentrations $A_{tot}$ and $B_{tot}$ to perform this series of experiments. Therefore, we considered to measure the relaxation time and the rate constants $k_{on}$ and $k_{off}$ at lower temperatures, and to subsequently extrapolate their values at higher temperatures upon adopting the Arrhenius expression to account for the temperature-dependence of the rate constants $k_{on}(T)$ and $k_{off}(T)$ $$k_{on}(T) = A_{on} \exp\left(-\frac{E_{a,on}}{RT}\right) \quad (18)$$

$$k_{off}(T) = A_{off} \exp\left(-\frac{E_{a,off}}{RT}\right) \quad (19)$$

where $A_{on}$ and $A_{off}$, and $E_{a,on}$ and $E_{a,off}$ respectively denote the frequency factors, and the activation energies associated to the forward and backward reaction (1).

We used two different approaches to extract the rate constants $k_{on}$ and $k_{off}$ from the relaxation time $\tau$:

We first measured $\tau$ at 15° C. in a series of experiments in which we used various initial concentrations $A_{tot}$ and $B_{tot}$. This series of experiments enabled to independently extract $k_{on}$ and $k_{off}$ at 15° C.: We found $(2.5\pm0.4)\times10^7$ $M^{-1}s^{-1}$ and $4.1\pm0.7$ $s^{-1}$, and $(2.0\pm0.5)\times10^7$ $M^{-1}$ $s^{-1}$ and $2.1\pm0.5$ $s^{-1}$ for HBR and HMBR respectively;

We then measured $\tau$ at various temperatures spanning the 10-25° C. range in series of experiments in which we used various initial concentrations $A_{tot}$ and $B_{tot}$. The latter variations being too narrow to independently extract $k_{on}$ and $k_{off}$ as above, we relied on the expression $K=k_{on}/k_{off}$ and on the temperature-dependence of the association constant K to extract the values of $k_{on}$ and $k_{off}$ from the relaxation time $\tau$ in the considered temperature range. In particular, the values of $k_{on}$ and $k_{off}$ extracted at 15° C. were in close agreement with the values determined previously.

Chemical Synthesis.

Commercially available rhodanine (Alfa Aesar), 3-methylrhodanine (Aldrich), rhodanine-3-acetic acid (Aldrich), 4-hydroxybenzaldehyde (Acros), 2,4-dihydroxybenzaldehyde (Aldrich), 4-hydroxy-2-methoxybenzaldehyde (Fluka), 4-hydroxy-3-methylbenzaldehyde (Acros) were used as starting materials without further purification. Analytical and thin layer chromatography (TLC): Merck silica gel 60 F-254 precoated plates; detection by UV (254 nm). NMR spectra were recorded on a AC Bruker spectrometer at 300 MHz for $^1$H and 75.5 MHz for $^{13}$C; chemical shifts are reported in ppm with protonated solvent as internal reference $^1$H, $CHD_2SOCD_3$ in $CD_3SOCD_3$ 2.52 ppm, $CHD_2OD$ in $CD_3COD$ 3.34 ppm; $^{13}$C, $^{13}CD_3SOCD_3$ in $CD_3SOCD_3$ 40.4 ppm; Coupling constants J in Hz. Mass spectra (chemical ionization and electronic impact with $NH_3$) were performed by the Service de Spectrométrie de Masse de Chimie ParisTech. Microanalyses were performed by the Service de Microanalyses de Gif sur Yvette.

(Z)-5-(4-hydroxybenzylidene)-2-thioxo-1,3-thiazolidin-4-one (HBR)—A solution containing rhodanine (202 mg; 1.52 mmol) and 4-hydroxybenzaldehyde (195 mg; 1.60 mmol) in 110 mL of water was stirred at 65-80° C. for 10 days. After cooling to room temperature and standing overnight, the precipitate was filtered over a glass filter. After drying over $P_2O_5$, HBR was obtained as a dark yellow powder (235 mg; 65%). $^1$H-NMR (300 MHz, CD3OD) δ (ppm) 7.57 (s, 1 H), 7.45 (d, J=8.7 Hz, 2 H), 6.94 (d, J=8.7 Hz, 2 H).

(Z)-5-(4-hydroxybenzylidene)-3-methyl-2-thioxothiazolidin-4-one (HBMR)—Same as HBR. 3-Methylrhodanine (200 mg; 1.36 mmol), 4-hydroxybenzaldehyde (174 mg; 1.42 mmol), water (110 mL); stirring at 65° C. for 8 days. HBMR as a yellow powder (286 mg; 84%). $^1$H-NMR (300 MHz, DMSO-d6) δ(ppm) 7.76 (s, 1 H), 7.54 (d, J=9.0 Hz, 2H), 6.95 (d, J=9.0 Hz, 2 H), 3.41 (s, 3 H).

(Z)-2-(5-(4-hydroxybenzylidene)-4-oxo-2-thioxothiazolidin-3-yl)acetic acid (HBAAR) —Same as HBR. Rhodanine-3-acetic acid (202 mg; 1.06 mmol), 4-hydroxybenzaldehyde (136 mg; 1.11 mmol), water (110 mL); stirring at 65° C. for 8 days. HBAAR as a yellow powder (127 mg; 41%). $^1$H-NMR (300 MHz, DMSO-d6) δ(ppm) 10.57 (s, 1H), 7.83 (s, 1 H), 7.58 (d, J=8.7 Hz, 2 H), 6.97 (d, J=8.7 Hz, 2 H), 4.75 (s, 2 H).

(Z)-5-(2,4-Dihydroxybenzylidene)-2-thioxo-1,3-thiazolidin-4-one (DHBR)3,5,6—Same as HBR. Rhodanine (200 mg; 1.50 mmol), 2,4-dihydroxybenzaldehyde (216 mg; 1.56 mmol), water (110 mL); stirring at 65° C. for 8 days. DHBR as a brown powder (138 mg; 36%). $^1$H-NMR (300 MHz, DMSO-d6) δ(ppm) 10.66 (s, 1 H), 10.34 (s, 1H), 7.82 (s, 1 H), 7.17 (d, J=9.0 Hz, 1 H), 6.44 (d, J=9.0 Hz, 1 H), 6.43 (s, 1H); $^{13}$C-NMR (75.5 MHz, DMSO-d6) δ(ppm) 196.2, 170.1, 162.9, 160.3, 131.6, 128.5, 119.2, 112.3, 109.3, 103.0; Mass spec (CI/$NH_3$) [M+H$^+$]: 254.0; Anal calc. for $C_{10}H_7NO_3S_2$, 0.29 $H_2O$ (MW: 253+5; water was present in the $^1$H-NMR spectrum) C: 46.69%, H: 2.95%, N: 5.42%, S, 24.81%; Found C: 46.72%, H: 2.80%, N: 5.45%, S, 26.25%.

(Z)-5-(4-hydroxy-3-methoxybenzylidene)-2-thioxo-1,3-thiazolidin-4-one (HMOBR)—Same as HBR. Rhodanine (200 mg; 1.50 mmol), 4-hydroxy-2-methoxybenzaldehyde (237 mg; 1.56 mmol), water (140 mL); stirring at 65° C. for 8 days. HMOBR as a dark yellow powder (239 mg; 60%). $^1$H-NMR (300 MHz, DMSO-d6) δ(ppm) 10.57 (s, 1H), 7.77 (s, 1 H), 7.26 (d, J=8.4 Hz, 1 H), 6.57 (dd, J=8.4 Hz and 3.6 Hz, 1 H), 6.54 (d, J=3.6 Hz, 1 H), 3.87 (s, 3 H); $^{13}$C-NMR (75.5 MHz, DMSO-d6) δ(ppm) 196.3, 170.1, 163.2, 160.9, 132.2, 128.0, 120.8, 113.3, 109.5, 99.9, 56.2; Mass spec (CI/$NH_3$) [M+H$^+$]: 268.0; Anal calc. for $C_{11}H_9NO_3S_2$ (MW: 267) C: 49.42%, H: 3.39%, N: 5.24%, S, 23.99%; Found C: 49.15%, H: 3.47%, N: 5.30%, S, 24.21%.

(Z)-5-(4-hydroxy-3-methylbenzylidene)-2-thioxo-1,3-thiazolidin-4-one (HMBR)—Same as HBR. Rhodanine (200 mg; 1.50 mmol), 4-hydroxy-3-methylbenzaldehyde (213 mg; 1.56 mmol), water (130 mL); stirring at 65° C. for 8 days. HMBR as a yellow powder (198 mg; 53%). $^1$H-NMR (300 MHz, DMSO-d6) δ(ppm) 10.39 (s, 1H), 7.54 (s, 1 H), 7.35 (d, J=2.7 Hz, 1 H), 7.33 (dd, J=7.8 Hz and 2.7 Hz, 1 H), 6.96 (d, J=7.8 Hz, 1 H), 2.19 (s, 3H); $^{13}$C-NMR (75.5 MHz, DMSO-d6) δ(ppm) 196.1, 170.0, 159.2, 134.1, 133.2, 131.1, 126.0, 124.3, 121.2, 116.1, 16.4; Mass spec (CI/$NH_3$) [M+H$^+$]: 252.0; Anal calc. for $C_{11}H_9NO_2S_2$ (MW: 251) C: 52.57%, H: 3.61%, N: 5.57%, S, 25.52%; Found C: 52.68%, H: 3.64%, N: 5.58%, S, 25.58%.

Cloning

The gene of *Halorhodospira halophila* PYP-C69G codon-optimized for expression in yeast (SEQ ID NO: 139), the gene Y-FAST codon-optimized for expression in yeast (SEQ ID NO: 140) and the gene of Y-FAST codon-optimized for expression in human cells (SEQ ID NO: 141) were synthesized by Eurofins Genomics. The plasmid pAG14 enabling the expressing of PYP-C69G in fusion to Aga2p for expression at the yeast cell surface was obtained by inserting the gene of PYP-C69G (sequence codon-optimized for expression in yeast) between Nhe I and BamH I restriction sites in the pCTCON2 vector. The plasmids pAG86, pAG87, pAG88, pAG89, pAG90, pAG91 and pAG95 enabling the bacterial expression of respectively clone 2 (SEQ ID NO: 2), clone 3 (=Y-FAST, SEQ ID NO: 3), clone 4 (SEQ ID NO: 4), clone 5 (SEQ ID NO: 5), clone 6 (SEQ ID NO: 6) and PYP-C69G (SEQ ID NO: 48) with a N-terminal His-tag were obtained by inserting the gene encoding ENLYFQG-cloneX (sequence selected by yeast display) (X=2-6)(or PYP-C69G) between Nhe I and Xho I restriction sites in the pET28a vector (the sequence ENLYFQG (SEQ ID NO: 148) corresponds to the sequence recognized by the TEV protease, enabling removal of the His-tag by TEV digestion). The plasmids pAG96 and pAG97 enabling the mammalian expression of mCherry (SEQ ID NO: 149) fused to Y-FAST or to PYP-C69G were obtained by cloning the sequence encoding mCherry-GGGS-Y-FAST (SEQ ID NO: 150) (or PYP-C69G, SEQ ID NO: 151) between Bgl II and Not I restriction sites in the pIRES vector (Clontech). The plasmids pAG29, pAG104, pAG105, pAG106, pAG55 and pAG59 enabling the mammalian expression of respectively EGFP, Y-FAST, Y-FAST-NLS, Lyn11-Y-FAST, Ensconsin-Y-FAST, Dronpa-NLS, Lyn11-Dronpa were obtained by inserting the sequence encoding EGFP-GGGSGGGSPG (SEQ ID NO: 130), Y-FAST-GSEQKLISEEDL (SEQ ID NO: 131), Y-FAST-GSEQKLISEEDLGAGAPKKKRKVP-KKKRK (SEQ ID NO: 132), MGCIKSKGKDSAGGGS-Y-FAST-GSEQKLISEEDL (SEQ ID NO: 133), Ensconsin-SAGGGS-Y-FAST-GSEQKLISEEDL (SEQ ID NO: 134), Dronpa-GSEQKLISEEDLGAGAPKKKRKVPKKKRK (SEQ ID NO: 135), and MGCIKSKGKDSAGGGS-Dronpa-GSEQKLISEEDL (SEQ ID NO: 136) between Bgl II and Not I restriction sites in the pIRES vector. The plasmids pAG113 and pAG114 enabling the synthesis of the mRNA encoding mCherry-P2A-Y-FAST and mCherry-P2A-PYP-C69G for zebrafish injection were obtained by inserting the sequence coding for mCherry-GSGATNFSLLKQAGD-VEENPGPSRGGGS-Y-FAST (SEQ ID NO: 137) (or PYP-C69G, SEQ ID NO: 138) between BamH I and SnaB I in a modified version of pCS2. The plasmid pAG101 enabling the expression of mCherry-Y-FAST under the control of a T7 promoter for in vitro protein synthesis was obtained by inserting the sequence coding for mCherry-GSSSENLY-FQG-Y-FAST (SEQ ID NO: 152) between Nhe I and Xho I restriction sites in the pET28a vector. All sequences were verified by DNA sequencing.

Physico-Chemical Experiments pH measurements were performed on a Standard pH meter PHM210 Radiometer Analytical (calibrated with aqueous buffers at pH 4 and 7 or 10) with a Crison 5208 Electrode (Barcelona, Spain). UV/Vis absorption spectra were recorded in 1 cm×1 cm quartz cuvettes (Hellma) on a diode array UV/Vis spectrophotometer (Evolution array, Thermo Scientific). Corrected fluorescence spectra upon one-photon excitation were recorded with a Photon Technology International QuantaMaster QM-1 spectrofluorimeter (PTI, Monmouth Junction, NJ) equipped with a Peltier cell holder (TLC50, Quantum Northwest, Shoreline, Wash.). The overall emission quantum yields after one-photon excitation $\phi$ were calculated from the relation:

$$\phi = \phi_{ref} \frac{1 - 10^{-A_{ref}(\lambda_{exc})}}{1 - 10^{-A(\lambda_{rec})}} \frac{D}{D_{ref}} \left(\frac{n}{n_{ref}}\right)^2$$

where the subscript ref stands for standard samples. $A(\lambda_{exc})$ is the absorbance at the excitation wavelength $\lambda_{exc}$, D is the integrated emission spectrum, and n is the refractive index for the solvent. The uncertainty for the experimental value of $\phi$ was estimated to be ±20%. The standard fluorophore for the quantum yields measurements was Fluorescein in sodium hydroxide 0.1 M with $_{ref}$=0.92. The titration experiments used for the determination of the thermodynamic constants were performed on a SpectraMax®M5e (Molecular Devices) plate-reader. The on- and off-rate constants were determined by stopped-flow experiments using a RX2000 rapid kinetic stopped flow accessory (Applied Photophysics, Leatherhead, UK). The circular dichroism spectra were recorded on a J-815 circular dichroism spectropolarimeter (Jasco). The photobleaching experiments were performed on a the Photon Technology International QuantaMaster QM-1 spectrofluorimeter (PTI, Monmouth Junction, NJ) equipped with a Peltier cell holder (TLC50, Quantum Northwest, Shoreline, Wash.).

Yeast Display

Library Construction. The yeast display libraries were constructed from the gene of PYP-C69G by saturation mutagenesis using NNK degenerated primers. Library 1 randomized at positions 52, 53, 65, 66, 67, 68, 69 was constructed as followed: two PCR fragments were generated using the pairs of primers AG42/AG43 and AG44/AG46, then assembled by PCR using AG42/AG46 (primers are listed below). The PCR product was digested with Nhe I and BamH I, and then ligated in pCTCON2 using Nhe I/BamH I restriction sites. Large-scale transformation performed by electroporation in DH10B E. coli cells led to 7×10$^7$ transformants. DNA was then minipreped, and retransformed in EBY100 yeast strain using large-scale high-efficiency transformation protocol, leading to 8×10$^7$ transformants. Library 2 randomized at 94, 95, 96, 97, 98, 99, 100, 101 was constructed as followed: a PCR product was generated using the pair of primers AG42/AG45. The PCR product was digested with Nhe I and Sty I, and then ligated in pAG14 using Nhe I/Sty I restriction sites. Large-scale transformation performed by electroporation in DH10B E. coli cells led to 3×10$^7$ transformants. DNA was then minipreped, and retransformed in EBY100 yeast strain using large-scale high-efficiency transformation protocol, leading to 8×10$^6$ transformants. Library 3 randomized at 52, 53, 65, 66, 67, 68, 69, 94, 95, 96, 97, 98, 99, 100, 101 was constructed as followed: two PCR fragments were generated using the pairs of primers AG42/AG43 and AG44/AG45, then assembled by PCR using AG42/AG45. The PCR product was digested with Nhe I and Sty I, and then ligated in pAG14 using Nhe I/Sty I restriction sites. Large-scale transformation performed by electroporation in DH10B E. coli cells led to 1.5×10$^7$ transformants. DNA was then minipreped, and retransformed in EBY100 yeast strain using large-scale high-efficiency transformation protocol, leading to 8×10$^7$ transformants.

AG42 (SEQ ID NO: 142):
5'-GGTCGGCTAGCATGGAACATG-3'

AG43 (SEQ ID NO: 143):
5'-AAGTTCTTGCCAATCACTTGTTTGGGMNNMNNCCCTGTTATGTCTCCTTC-3'

AG44 (SEQ ID NO: 144):
5'-GATTGGCAAGAACTTCTTCAAANNKNNKNNKNNKNNKACAGATTCTCCTGAATTTTAC-3'

AG45 (SEQ ID NO: 145):
5'-TTTAACCTTGGTTGGMNNMNNMNNMNNMNNMNNMNNMNNCTCGAACATGGTATTCAAG-3'

AG46 (SEQ ID NO: 146):
5'-TTTGTTCGGATCCAACCCTTTTG-3'

AG47 (SEQ ID NO: 147):
5'-CGTTCCAGACTACGCTCTGC-3'

Selection. Libraries (typically 1×10$^{10}$ cells) were grown overnight (30° C., 280 rpm) in 1 L of SD (20 g/L dextrose, 6.7 g/L yeast nitrogen base, 1.92 g/L yeast synthetic dropout without tryptophane, 7.44 g/L NaH$_2$PO$_4$ and 10.2 g/L Na$_2$HPO$_4$-7H$_2$O, 1% penicillin-streptomycin 10,000 U/mL). 1×10$^{10}$ cells yeast cells were then collected and grown for 36 h (23° C., 280 rpm) in 1L SG (20 g/L galactose, 2 g/L dextrose, 6.7 g/L yeast nitrogen base, 1.92 g/L yeast synthetic dropout without tryptophane, 7.44 g/L NaH$_2$PO$_4$, 10.2 g/L Na$_2$HPO$_4$-7H$_2$O, 1% penicillin-streptomycin 10,000 U/mL). 6×10$^8$ induced cells were then pelleted by centrifugation (25° C., 3 min, 2,500 g), washed with 10 mL DPBS-BSA (137 mM NaCl, 2.7 mM KCl, 4.3 mM Na$_2$HPO$_4$, 1.4 mM KH$_2$PO$_4$, 1 g/L bovine serum albumin, pH 7.4), and incubated for 30 min at room temperature in 200 µL of 1/250 primary antibody chicken anti-c-Myc IgY (Life Technologies) solution in DPBS-BSA. Cells were then washed with 10 mL DPBS-BSA, and incubated in 200 µL of 1/100 secondary antibody Alexa Fluor® 647—goat anti-rabbit IgG (Life Technologies) solution in DPBS-BSA for 30 min on ice. After washing with DPBS-BSA, cells were incubated in 10 mL DPBS-BSA supplemented with 20 µM HBR, and sorted on a MoFlo™ XDP High-Speed Cell Sorter equipped with a 488 nm and a 633 nm laser. The sorted cells were collected in SD, grown overnight (30° C., 240 rpm) and spread on SD plates (SD supplemented with 182 g/L sorbitol, 15 g/L agar). Plates were incubated for 60 h at 30° C. The cell lawn was collected in SD supplemented with 30% glycerol, aliquoted and frozen or directly used in the next round.

Protein Expression and Purification

Expression vectors were transformed in Rosetta(DE3) pLysS *E. coli* (New England Biolabs). Cells were grown at 37° C. in Lysogeny Broth (LB) medium complemented with 50 µg/ml kanamycin and 34 µg/ml chloramphenicol to OD600 nm 0.6. Expression was induced for 4 h by adding isopropyl β-D-1-thiogalactopyranoside (IPTG) to a final concentration of 1 mM. Cells were harvested by centrifugation (6,000 g for 15 min at 4° C.) and frozen. Cell pellet was resuspended in lysis buffer (phosphate buffer 50 mM, NaCl 150 mM, MgCl$_2$ 2.5 mM, protease inhibitor, DNase, pH 7.4) and sonicated (5 min at 20% of amplitude). The lysate was incubated 2 h at 4° C. to allow DNA digestion by DNase. Cellular fragments were removed by centrifugation (15,000 g for 1 h at 4° C.). The supernatant was incubated overnight at 4° C. under gentle agitation with Ni-NTA agarose beads in Phosphate buffered saline (PBS) (sodium phosphate 50 mM, NaCl 150 mM, pH 7.4) complemented with 10 mM Imidazole. Beads were washed with 20 volumes of PBS complemented with 20 mM Imidazole, and with 5 volumes of PBS complemented with 40 mM Imidazole. His-tagged proteins were eluted with 5 volumes of PBS complemented with 0.5 M Imidazole. Extensive dialysis enabled to exchange buffer with PBS. His-tag was cleaved by incubation the protein sample with His-tagged Tobacco Etch Virus protease (TEV) for 18 h at 18° C. After removal of the TEV protease using Ni-NTA beads, the protein sample was eventually extensively dialyzed against 2.5 mM sodium phosphate buffer for subsequent lyophilization. Lyophilized proteins were stored at 4° C.

Analytical size-exclusion chromatography was performed at 16° C. on an Äkta Purifier system (GE Healthcare) equipped with a superdex 200 5/150 GL column and calibrated with Dextran blue, Ferritine, Conalbumine, Carbonic Anhydrase, Aldolase, Ovalbumine and Ribonuclease. Pre-equilibration of the column was performed with pH 7.4 PBS (sodium phosphate 50 mM, NaCl 150 mM). The elution flow rate was set at 0.2 ml/min.

Cell Free Protein Synthesis

The cell-free protein synthesis was performed using the PURExpress in vitro Protein Synthesis Kit (New England Biolabs) according to the manufacturer's protocol. Luminescence emissions were followed over time using a SpectraMax®M5e plate-reader (Molecular Devices).

Mammalian Cell Culture

HEK293 and HeLa cells were cultured in DMEM supplemented with phenol red, Glutamax I, 10% fetal calf serum and 1% penicillin-streptomycin at 37° C. within a 5% $CO_2$ atmosphere. For microscopy imaging, cells were seeded in µDish IBIDI (Biovalley) coated with poly-L-lysine. Cells were transiently transfected using Genejuice (Merck) according to the manufacturer's protocol. Before imaging, cells were washed with PBS and incubated in DMEM without phenol red complemented with HBR or HMBR at the indicated concentration (final DMSO content 0.033%).

Neuron Cultures

Cultures of dissociated spinal cord neurons were prepared from Sprague-Dawley rats (at embryonic day 14) as described previously. Neurons were maintained in neurobasal medium containing B27, 2 mM glutamax, 5 U/ml penicillin and 5 µg/ml streptomycin at 36° C. and 5% $CO_2$, co-transfected at day in vitro DIV15 with Y-FAST-Gephyrin and mCerulean-Gephyrin plasmid DNA using Lipofectamine 2000 (Invitrogen), and used for experiments on DIV17. Neurons were imaged at 35° C. in MEM medium without phenol red, containing 33 mM glucose, 20 mM HEPES, 2 mM glutamax, 1 mM sodium pyruvate and B27. HMBR was added by bath application at a final concentration of 10 µM in imaging buffer.

Zebrafish Experiments

Zebrafish were maintained and staged according to Westerfield. Experiments were performed using the standard Ab wild type strain. The embryos were incubated at 28° C. The animal facility obtained a French agreement from the ministry of agriculture for all the experiments performed (agreement n° C. 75-05-12). mRNA synthesis was performed using the mMESSAGE mMACHINE Transcription Kit (Ambion Inc). Equivalent volume of 100 ng/ml mRNA was injected into one-cell stage embryos. Embryos were allowed to grow in Volvic mineral water until imaging.

Fluorescence Analysis

Flow cytometry analysis was performed on an Accuri C6 (BD Biosciences). Confocal micrographs were acquired on a Zeiss LSM 710 Laser Scanning Microscope equipped with a Plan Apochromat 63×/1.4 NA oil immersion objective. ZEN software was used to collect the data. Images were analyzed with Image J. Spinning-disk confocal micrographs were acquired on a Nikon Eclipse Ti microscope equipped with a 4×/0.15 N.A objective and a coolSnap HQ2/CDD-camera (Princeton Instrument). Metamorph premier 7.6 software (Molecular Devices) was used to collect the data.

Microfluidic-Controlled on/Off Labeling.

A rapid prototyping technique has been used for the device fabrication. A digital cutting machine (Graphtec, CE6000) was used to produce a 0.5 mm wide microfluidic channel in a 0.5 mm thick silicone layer, which was supported by a 50 µm thick plastic film. After removing the plastic film and oxygen plasma treatment, the silicone layer was bonded to a 5 mm thick layer of polydimethylsiloxane (PDMS) which was prepared by casting a mixture of A and B components of RTV 615 (GE, France) at a 10:1 w/w ratio on a flat silicon wafer and curing it at 80° C. for 2 h. Then, inlet and outlet holes were punched with a metal tube for connections. Afterward, the silicone-PDMS complex was bonded to a 160 µm thick cover slide after oxygen plasma treatment. Finally, the whole device was put in a 80° C. oven for 10 min. Before cell seeding, the device was sterilized under UV exposure for more than 30 min. A solution of fibronectin at 50 µg/ml concentration in 0.1 M $NaHCO_3$ (pH 8) was injected into the channel and incubated at 37° C. for 30 min. The channel was washed three times with PBS solution, then 200 µL cell suspension with a cell density of 100,000 cells/ml was introduced in the device and the whole system was incubated at 37° C. for 1 h. Dynamic control of the cellular staining-imaging processes was achieving by using a multifunctional fluidic controller (FC-PVL-II, Meso-BioSystem). The alternative injection of normal and HMBR-containing culture medium into the microfluidic channel was controlled with a home-made project downloaded to the controller so that the whole staining-imaging processes could be performed in an automatic way.

Fluorescence Resonance Energy Transfer Experiments

Considering its spectral properties, Y-FAST can be used a priori as a donor in a FRET pair with mCherry. To demonstrate this, we determined the yield of the fluorescence resonance energy transfer of electronic excitation in the fusion protein Y-FAST-mCherry by performing a series of cuvette experiments keeping constant the conditions for recording both absorption and emission spectra.

We recorded the absorption and emission ($\lambda_{exc}$=470 nm) spectra of 1.5 µM Y-FAST-mCherry in absence and in presence of 250 nM HMBR. In a second step, we recorded the absorption and the emission ($\lambda_{exc}$=470 nm) spectra of 1.5 µM Y-FAST in the presence of 250 nM HMBR.

Denoting 1, 2, and 3 the species Y-FAST-mCherry, HMBR:Y-FAST-mCherry, and HMBR:Y-FAST, and $\varepsilon_i(\lambda_{exc})$ and $I_i(\lambda_{exc},\lambda_{em})$ the molar absorption coefficient at $\lambda_{exc}$ and the intensity of fluorescence emission at $\lambda_{en}$, of the species i, the yield $\phi_{ET}$ of the fluorescence resonance energy transfer of electronic excitation has been extracted by two different methods from the results of the described series of experiments:

We first extracted $\phi_{ET}$ from the variation of the fluorescence emission of the donor HMBR:Y-FAST. Hence, we wrote:

$$\phi_{ET} = 1 - \frac{I_2(470,550)}{I_3(470,550)} \quad (2)$$

and found $\phi_{ET}$=0.5±0.1;

We alternatively extracted $\phi_{ET}$ from the variation of the fluorescence emission of the acceptor mCherry. Hence, we wrote:

$$\phi_{ET} = \frac{[I_2(470,616) - (I_1(470,616) + I_3(470,616))]}{\left(\frac{\varepsilon_1(470)}{\varepsilon_3(470)}I_1(470,616) - I_3(470,616)\right)} \quad (3)$$

and found $\phi_{ET}$=0.25±0.15. This second derivation is notably less reliable since it propagates errors from a large number of experiments.

Once $\phi_{ET}$ determined, we next extracted an order of magnitude of the average distance R between HMBR and the mCherry chromophore from assuming fluorescence resonance energy transfer to be governed by the Förster mechanism. Hence we wrote $$R = R_0 \left(\frac{1}{\phi_{ET}} - 1\right)^{\frac{1}{6}} \quad (4)$$

where $R_0$ (in nm) designates the Förster distance defined as)

$$R_0 = 0.021(\kappa^2 \Phi_3 n^{-4} \int_0^\infty I_3(\lambda)\varepsilon_1(\lambda)\lambda^4 d\lambda)^{1/6} \quad (5)$$

where $\kappa^2$ is the orientational factor (subsequently taken equal to ⅔ upon assuming the donor and the acceptor to sample all orientations), $\Phi_3$ is the fluorescence quantum yield of HMBR:Y-FAST ($\Phi_3$=0.33), n is the average refractive index of the medium in the wavelength range where spectral overlap is significant (n=1.33), $I_3(\lambda)$ is the normalized fluorescence spectrum of HMBR:Y-FAST so that $$\int_0^\infty I_3(\lambda)d\lambda = 1 \quad (6)$$

$\varepsilon_i(\lambda)$ is the molar absorption coefficient of Y-FAST-mCherry (in $M^{-1} \cdot cm^{-1}$), and $\lambda$ is the wavelength (in nm). We found R=5±1 nm, in good agreement with the distance of the two chromophores in our construct containing Y-FAST (modeled as a sphere of diameter ~2 nm), a GSSSENLYFQG linker of length ~3 nm (considering ~0.3 nm per residue), and mCherry (modeled as a cylinder with a ~2 nm diameter and a ~4 nm height).

Example 1

Design of a New Fluorogenic Chromophore—Identification of HBR

A fluorogenic chromophore capable to show high fluorescence increase when immobilized in a rigid environment such as a protein cavity, and exhibiting a shifted absorption upon ionization of an auxochromic group was designed.

It is known in the art that the chromophore of GFP, i.e. parahydroxybenzylidene-5-imidazolinone (p-HBI), displays an extremely weak fluorescence quantum yield when the protein is unfolded, but said fluorescence quantum yield increases by $10^4$-fold in the barrel tertiary protein structure (Heim et al., 1995; Tsien, 1998). Further, the protonated form of p-HBI absorbs at 397 nm while its deprotonated form absorbs at 475 nm. These photophysical properties of p-HBI originate from its typical donor-acceptor conjugated structure, where phenol/phenolate act as electron-donating groups and the imidazolidinone ring acts as the electron-withdrawing group.

New fluorogenic chromophores were designed, upon retaining the hydroxybenzylidene moiety of the GFP chromophore, and in replacing the thioester group by other headgroups exhibiting a broad range of electron-withdrawing properties. The phenol ring, which acts as an ionizable electron-donating group, was conjugated to various electron-withdrawing groups via a double bond. The new fluorogenic chromophores were further designed such that their steric hindrance remains globally compatible with a PYP cavity. Depending on the selected headgroup, the resulting fluorogenic chromophores were expected to have different absorption wavelengths and modulated pK values for the phenol group, such that the phenolate state could be generated only within the protein cavity of an engineered protein (preferably PYP) but not in the external medium.

Derivatives of p-HBI were prepared by replacing the electron-withdrawing imidazolidinone with other electron-withdrawing moieties. The new fluorogenic chromophores were synthesized in good yields by condensation of a head group containing activated methylene group onto a p-hydroxy-benzaldehyde possibly substituted in one or several of its benzenic positions.

The stability of the synthesized compounds was evaluated in aqueous solutions at neutral pH. Unstable and/or non-soluble compounds were not further studied. The photochemical and acido-basic properties of the remaining compounds were thus analyzed. Acid-base titrations were performed in aqueous solution by recording absorption and emission spectra as a function of pH. All investigated compounds exhibited a pK around neutrality with higher absorption wavelength for the phenolate state ranging from 330 to 450 nm.

The analysis then focused on a candidate compound absorbing at the highest wavelength for which the photophysical features of the phenol and phenolate states were analyzed in highly viscous glycerol solutions at low temperature to assay the effect of motion restriction.

The identified compound was shown to correspond to 5-(4-hydroxybenzylidene)-2-thioxothiazolidin-4-one, also called 4-hydroxybenzylidene-rhodanine (HBR). HBR is notably characterized by an electron-donating phenol conjugated via a double bond to an electron-withdrawing 2-thioxothiazolidin-4-one moiety, also called rhodanine. HBR showed significant brightness enhancement upon restriction of the fluorogen motion during the lifetime of the excited state of its acidic and basic forms.

Figure 2:
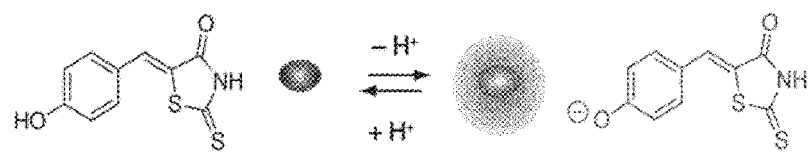
FIG. 2 is a mix of drawings and graphs depicting the structures of the protonated state and the unprotonated state of HBR (top), the absorption spectra of HBR in solution at pH 6.9 and 10.1 (bottom left), plots of the absorbance at 397 nm and 449 nm in function of pH (bottom right).
Figure 2:
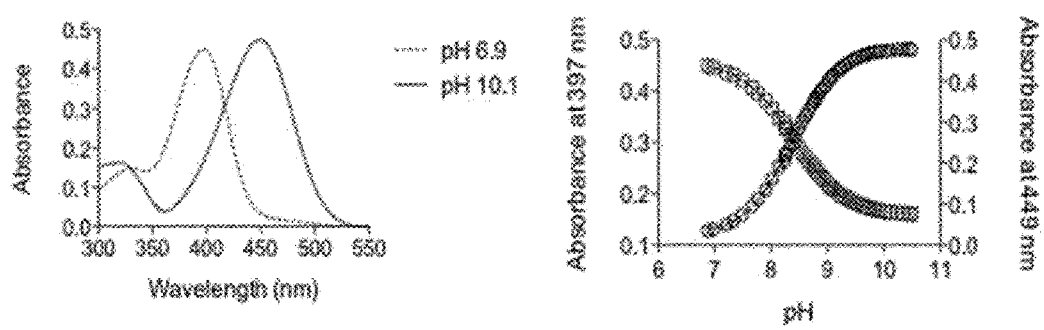
Figure 3:
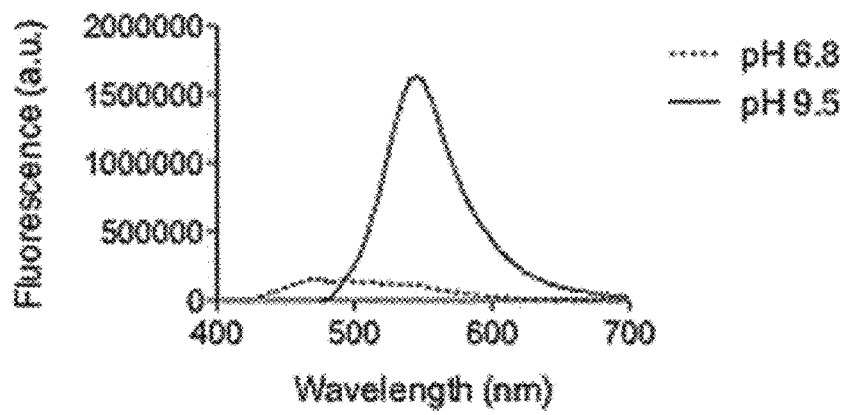
FIG. 3 is a graph depicting the fluorescence spectrum of HBR in solution at pH 6.8 and 9.5 (excitation wavelength 417 nm, isosbestic point).

The protonated phenol state of HBR was indeed shown to strongly absorb violet light (maximal absorption wavelength 397 nm), while the phenolate state strongly absorbs blue light (maximal absorption wavelength 449 nm) (FIG. 2). This red-shift in absorption upon ionization can be explained by the stronger electronic donation of the negatively charged phenolate. The possible fluorescence increase of HBR was evaluated by restricting the motion thereof in monitoring the influence of medium viscosity on HBR fluorescence emission. With a pKA of 8.4±0.1, HBR is mainly protonated at physiological pH, which enabled to forecast it could undergo a specific red shift upon binding-induced deprotonation within a tailored protein cavity. In aqueous solution, both acidic and basic states of HBR are weakly fluorescent (FIG. 3), emitting respectively at 470 and 545 nm with 0.02% and 0.3% fluorescence quantum yields. Six- and three-fold increases of the fluorescence quantum yield were respectively observed for the acidic and the basic states of HBR when glycerol content was increased from 0 to 40% (v/v), demonstrating that motion restriction could enhance HBR fluorescence.

These results enabled to conclude that, when excited by blue light at physiological pH, free HBR would be almost non-fluorescent (because it is protonated and therefore does not considerably absorb light in this wavelength domain) but HBR bound into a protein cavity complementary to its basic form would be strongly fluorescent because of both ionization (leading to red-shifted light absorption) and motion restriction (increasing the quantum yield of fluorescence).

Additional experiments showed that HBR could be synthesized in one step by condensation of the rhodanine or 2-thioxothiazolidin-4-one with the 4-hydroxybenzaldehyde in water.

Example 2

Design of PYP Derivatives

Fluorescent HBR-binding proteins were designed by remodeling the active site of the C69G photoactive yellow protein (PYP) from *Halorhodospira halophila* of SEQ ID NO: 48.

PYP is a 14 kDa monomeric disulfide-free blue-light photoreceptor, whose photosensing behavior relies on the photoisomerization of a para-hydroxycinnamoyl (HC) chromophore covalently attached to Cys69. The monomeric state and small size of PYP render this protein very attractive to design a new protein tag.

A directed evolution strategy of PYP was designed, based on yeast display, for remodeling the chromophore pocket of the apo-PYP-C69G of SEQ ID NO: 48 in order to obtain a cavity able to bind HBR in its basic blue-absorbing state and enhancing its fluorescence. The choice of apo-PYP as starting scaffold was driven by the likeness of the structures of HBR and the natural HC chromophore of PYP. Additionally, as the binding pocket of apo-PYP accommodates the HC chromophore in its deprotonated form, we hoped to benefit from this favorable cavity for stabilizing bound HBR in its deprotonated blue absorbing form.

Using the available PYP crystal structure (Borgstahl et al., 1995), the loops and residues in close proximity with the HC chromophore were identified, then randomized by saturation mutagenesis (Airaksinen and Hovi, 1998; Derbyshire et al., 1986; Miyazaki and Arnold, 1999; Steffens and Williams, 2007; Wang et al., 2007; Zheng, 2004). Three different libraries were constructed from the sequence encoding apo-PYP-C69G. Library 1 was obtained upon randomization of loops 52-53 and 65-69 of apo-PYP-C69G, library 2 was obtained upon randomization of loop 94-101 of apo-PYP-C69G, and library 3 was obtained upon randomization of the three loops 52-53, 65-69 and 94-101 (FIG. 4).

Figure 4:
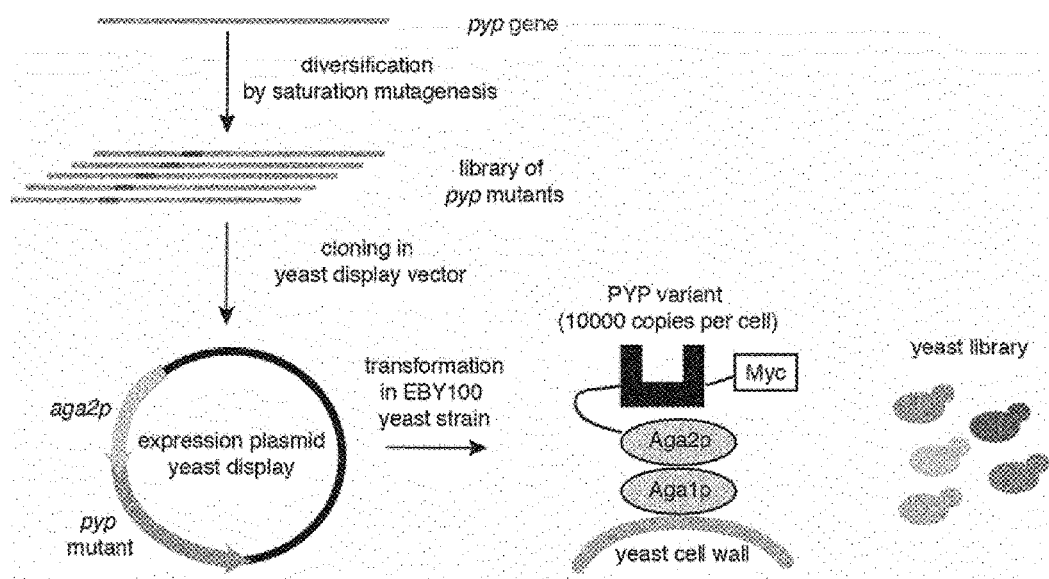
FIG. 4 is a drawing depicting the strategy for the creation of the yeast display libraries.

The three libraries were cloned into the yeast display pCTCON2 vector (Chao et al., 2006) to express the PYP variants as fusion to the adhesion subunit of the yeast agglutinin protein Aga2p, which attaches to the yeast cell wall through disulfide bonds to Aga1p (FIG. 4). High efficiency transformation (Gietz and Schiestl, 2007) in EBY100 yeast strain gave large yeast display libraries with $10^7$-$10^8$ diversity.

Figure 5:
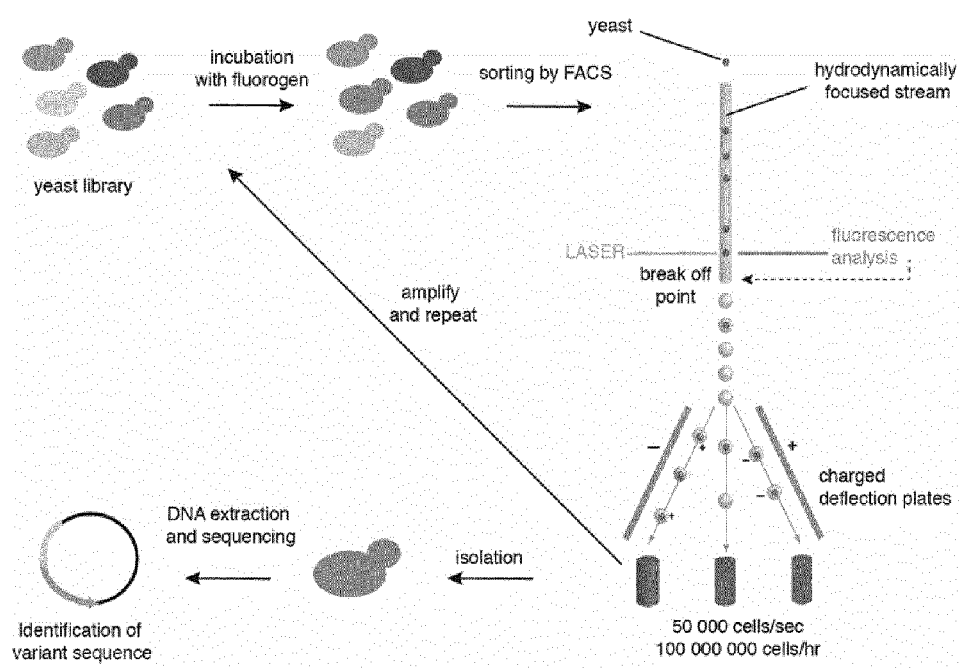
FIG. 5 is a drawing depicting the protocol applied for screening the yeast display libraries by fluorescence activating cell sorting (FACS).

Fluorescent HBR-binding PYP variants were identified by sorting the constructed yeast display libraries by Fluorescence Activating Cell Sorting (FACS) (Shapiro, 2003) (FIG. 5). The yeast populations were sorted in presence of HBR in PBS at pH 7.4 (since FACS is based on hydrodynamic flow focusing, cells can remain in presence of HBR until the detection step).

A 488 nm laser line for the excitation and a 540±30 nm filter to select the fluorescence emission were used for selecting the fluorescent cells. Three rounds of enrichment were performed on the separate libraries, then the obtained enriched cell populations were pooled together and three additional rounds of enrichment were realized on the mixture.

After this step of enrichment, 144 individual clones were tested for HBR-specific fluorescence.

Figure 6:
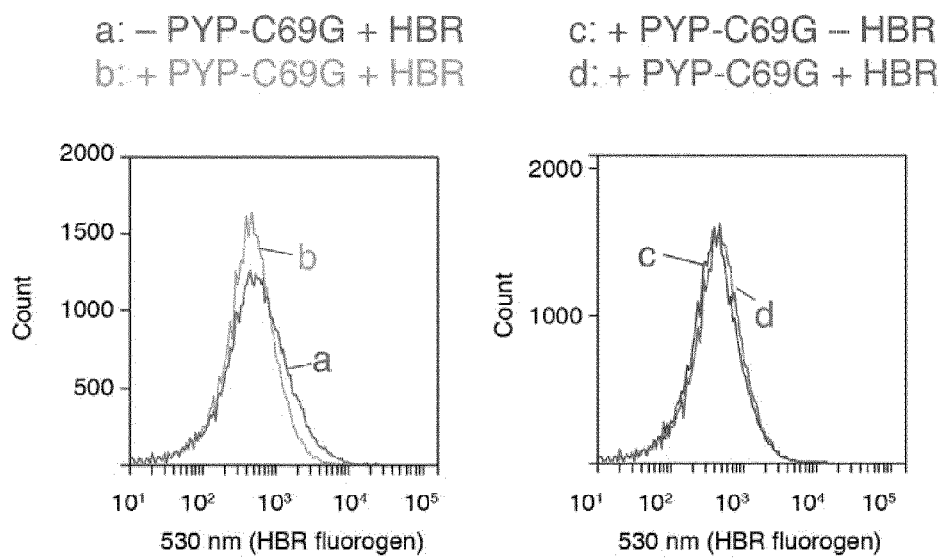
FIG. 6 is a graph depicting flow cytometry analysis of yeast cells expressing (+) or not (−) at the cell surface either PYP-C69G (of SEQ ID NO: 48) with (+) or without (−) 20 µM HBR. The plots show the fluorescence of the population at 530 nm due to HBR binding and activation (excitation 488 nm).
Figure 7:
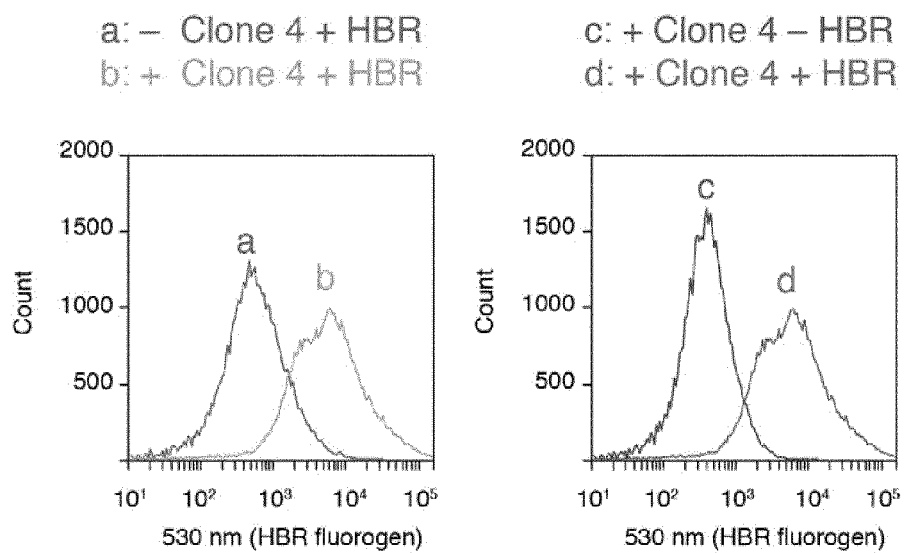
FIG. 7 is a graph depicting flow cytometry analysis of yeast cells expressing (+) or not (−) at the cell surface either an HBR-binding PYP derivative (clone 4 of SEQ ID NO: 4) of the invention with (+) or without (−) 20 µM HBR. The plots show the fluorescence of the population at 530 nm due to HBR binding and activation (excitation 488 nm).
Figure 8:
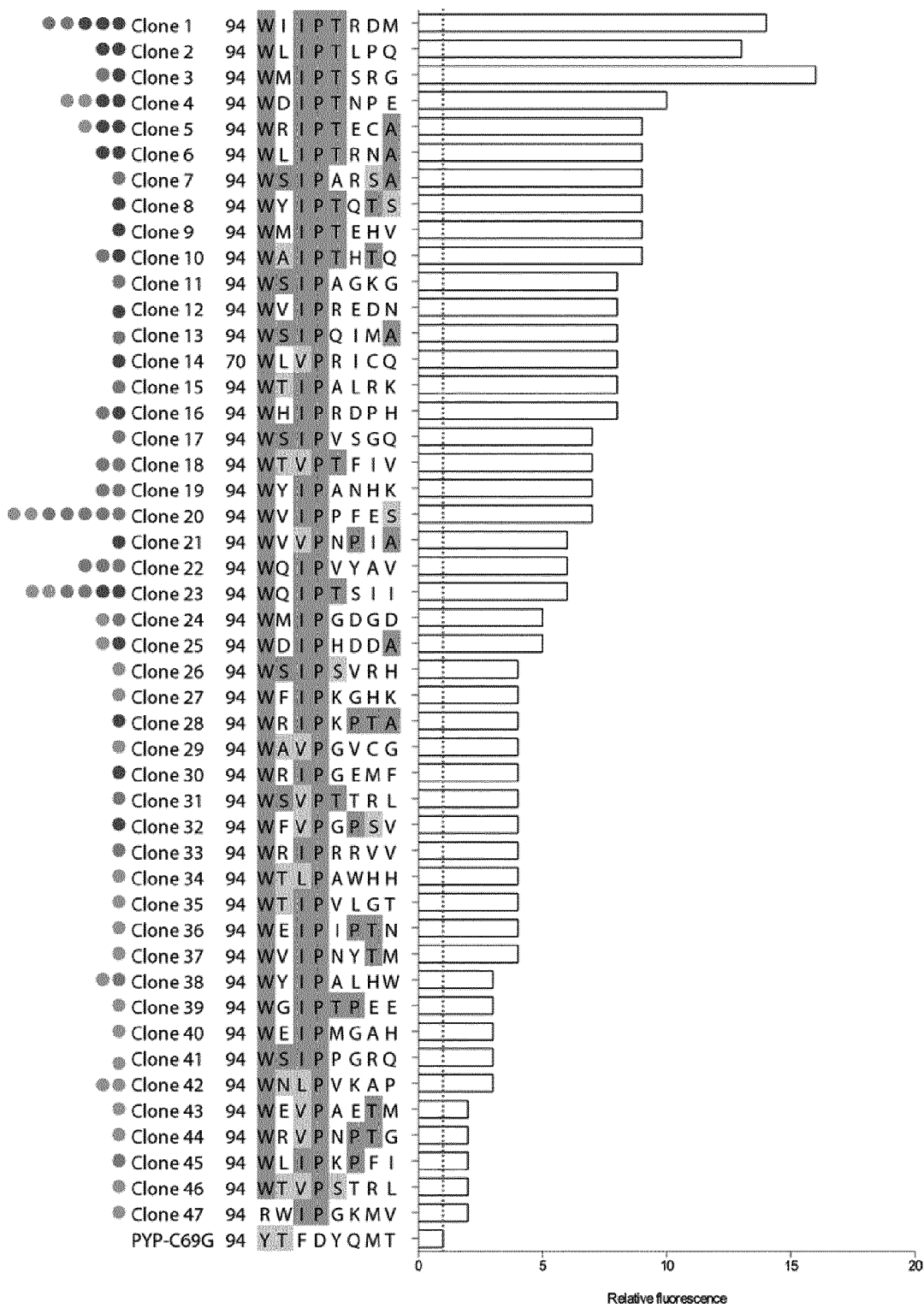
FIG. 8 is a drawing depicting the mutated residues 94-101 of the 47 identified fluorescent HBR-binding PYP variants (of SEQ ID NOs: 1-47, respectively). The figure shows also the relative fluorescence increase observed when analyzing the corresponding monoclonal yeast populations by flow cytometry.
Figure 9A:
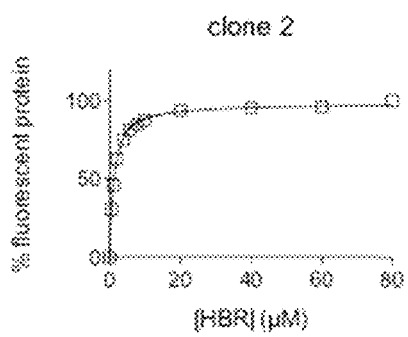
FIGS. 9 A, B, C, D and E display graphs depicting the titration curves used for determining the dissociation constants of the five fluorescent HBR-binding PYP variants (clones 2, 3, 4, 5, and 6, of SEQ ID NOs: 2, 3, 4, 5 and 6 respectively). Data=mean±SD of 3 experiments.
Figure 9B:
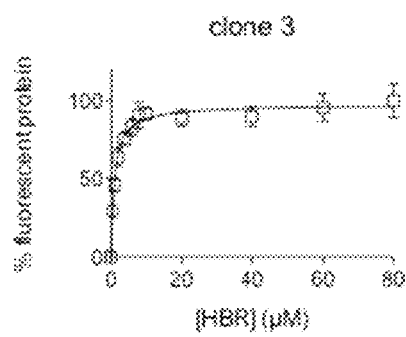
Figure 9C:
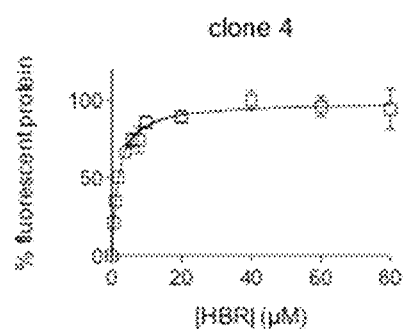
Figure 9D:
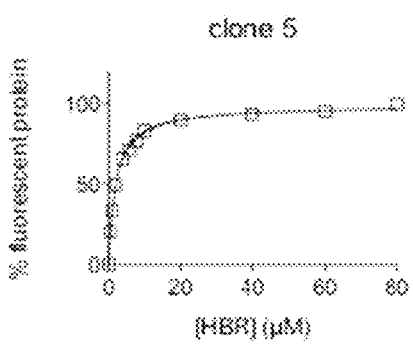
Figure 9E:
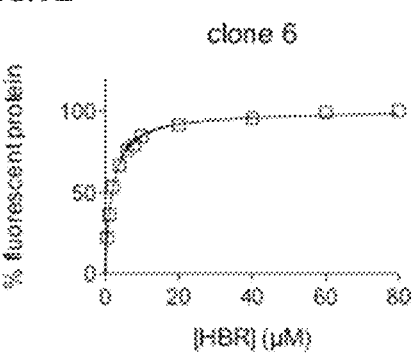

The fluorescence of the corresponding monoclonal yeast populations was analyzed in presence or absence of HBR by flow cytometry, and 80 clones showing HBR-specific fluorescence were identified (FIGS. 6 and 7). Further to DNA sequencing, these 80 clones were shown to correspond to 47 distinct variants (FIG. 8+SEQ ID NOs: 1-47). All the identified fluorescent HBR-binding PYP variants were shown to belong to the library 2, obtained by randomizing the loop 94-101 (which gates the entrance of the binding pocket). The emergence of the consensus sequence WxIPTxxx (SEQ ID NO: 129) confirmed convergence of the selection process.

The mutation D97P appears to be present in all variants.
Further, the mutation Y94W was identified in all variants but one.

In position 96, the aromatic phenylalanine present in apo-PYP was shown to be always replaced by residues with branched aliphatic side-chain. Isoleucine, valine and leucine appear respectively 36, 9 and 2 times.

In position 98, the mutation Y98T was observed 13 times.
This mutation was more specifically observed in nine of the ten clones inducing the highest fluorescence exaltation.

Some of the identified variants were further characterized in vitro. The variant proteins were expressed as His-tag fusions in Rosetta-DE3 *E. coli* strain and purified by Ni-NTA affinity chromatography. The His-tag was eventually removed by proteolytic cleavage. Size-exclusion chromatography (SEC) enabled to verify the monomeric state of the different variants.

The affinity of the selected variants for HBR was next evaluated by titration experiments using fluorescence exaltation to assay complex formation (FIG. 9). Dissociation constants ($K_D$) ranging from 1 to 2 μM were obtained for the different fluorescent proteins (see Table 1 below), confirming specific HBR binding.

TABLE 1 presents the dissociation constants of five fluorescent HBR-binding PYP variants (clones 2, 3, 4, 5, and 6).

| | Res. 94-101 | Sequence Number | Oligo-merization | $K_D$ (μM) |
|---|---|---|---|---|
| Clone 2 | WLIPTLPQ | SEQ ID NO: 82 | Monomer | 0.59 ± 0.02 |
| Clone 3 | WMIPTSRG | SEQ ID NO: 83 | Monomer | 0.62 ± 0.05 |
| Clone 4 | WDIPTNPE | SEQ ID NO: 84 | Monomer | 0.97 ± 0.08 |
| Clone 5 | WRIPTECA | SEQ ID NO: 85 | Dimer | 1.02 ± 0.03 |
| Clone 6 | WLIPTRNA | SEQ ID NO: 86 | | 0.93 ± 0.03 |
| PYP | YTFDYQMT | | Monomer | |

Figure 10A:
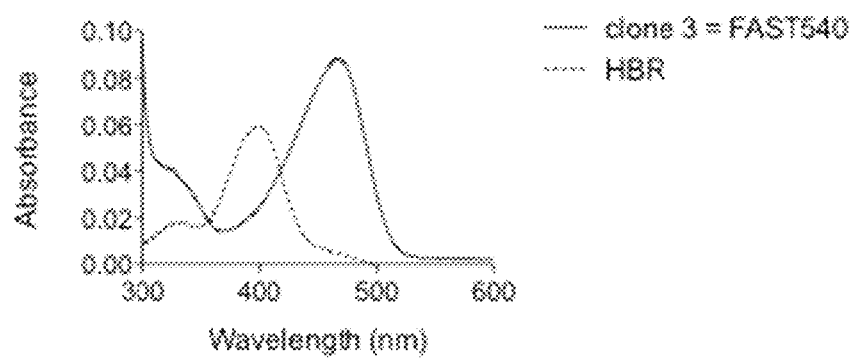
FIGS. 10 A and B display graphs depicting absorption and emission spectra of HBR and Y-FAST (HBR+clone 3 of SEQ ID NO: 3) in solution (PBS pH 7.4). [HBR]=2 µM, [apo-Y-FAST]=40 µM.
Figure 10B:
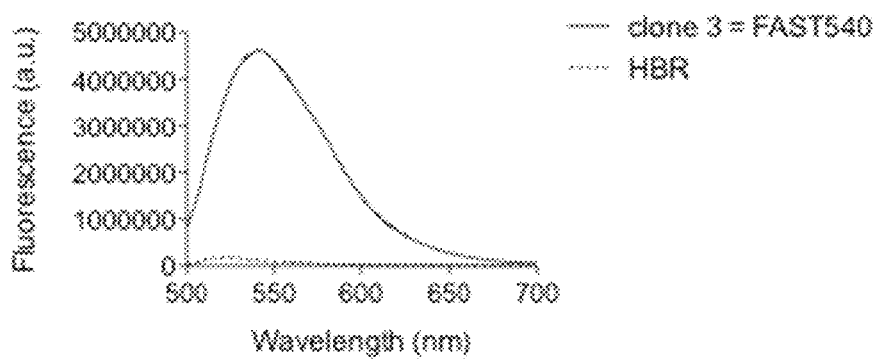

The photophysical properties of the engineered fluorescent proteins were more precisely characterized. Unlike HBR that strongly absorbed violet light (maximal absorption wavelength 397 nm) in PBS pH 7.4, five fluorescent HBR-binding PYP variants were shown to strongly absorb blue light (maximal absorption wavelength 470 nm) (FIG. 10 and Table 2 below). This 70 nm red-shift in absorption was in accordance with HBR being bound within the PYP-variant cavity in its deprotonated state. This red-shift in absorption upon binding was also accompanied with a large fluorescence increase at 540 nm (FIG. 10 and Table 2 below). The five fluorescent HBR-binding PYP variants displayed fluorescence quantum yields between 6 and 9%, giving brightness between 2500 $M^{-1}cm^{-1}$ and 4000 $M^{-1}cm^{-1}$, values comparable with those of some GFP-like fluorescent proteins, such as monomeric DsRed and mPlum (see Table 2 below).

The best fluorescent HBR-binding PYP variant (also referred to as clone 3 in the results) was named FAST540 or Y-FAST, where FAST means Fluorogen Activating and Shifting Tag, and 540 indicates the emission wavelength of the resulting fluorescent protein.

| Protein | $\lambda_{abs}$ (nm) | $\lambda_{em}$ (nm) | Extinction coefficient ($M^{-1}cm^{-1}$) | Fluorescence quantum yield | brightness | Relative brightness (% of EGFP) |
|---|---|---|---|---|---|---|
| Clone 2 | 466 | 540 | 46,000 | 0.06 | 2,800 | 8.3 |
| Clone 3 = Y-FAST | 467 | 542 | 44,000 | 0.09 | 4,000 | 12 |
| Clone 4 | 468 | 541 | 41,000 | 0.06 | 2,500 | 7.4 |
| Clone 5 | 468 | 542 | 47,000 | 0.06 | 2,800 | 8.3 |
| Clone 6 | 467 | 539 | 43,000 | 0.07 | 3,000 | 9.0 |
| mCFP[a] | 433 | 475 | 32,500 | 0.40 | 13,000 | 39 |
| EGFP[a] | 488 | 507 | 56,000 | 0.60 | 33,600 | 100 |
| EYFP[a] | 514 | 527 | 83,400 | 0.61 | 51,000 | 152 |
| mDsRed[a] | 556 | 586 | 35,000 | 0.10 | 3,500 | 10 |
| mPlum[a] | 590 | 649 | 41,000 | 0.10 | 4,100 | 12 |

[a]ref: N C Shaner, P A Steinbach, R Y Tsien Nat. Meth. 12, 905 (2005)

Table 2 presents the absorption and emission properties of five fluorescent HBR-binding PYP variants (clones 2, 3, 4, 5, and 6).

The fluorescent complex formed instantaneously (by eye) upon addition of HBR to Y-FAST. The determination of the on- and off-rate kinetic constants enabled to quantify the rapid formation of the complex (the relaxation time of binding is 30 ms at 25° C. when [HBR]=KD) and showed the short residence time of HBR in the bound state (the reciprocal of the off-rate constant is 60 ms at 25° C.), demonstrating that the binding is not only rapid but also highly dynamic (Table 3).

TABLE 3

Thermokinetic and photophysical properties of the complex between Y-FAST and HBR or HMBR at 25° C. (KD dissociation constant; $k_{ON}$ on-rate kinetic constant; $k_{OFF}$ off-rate kinetic constant; $\lambda_{abs}$ wavelength of maximal absorption; $\lambda_{em}$ wavelength of maximal emission; ε molar absorption coefficient at $\lambda_{abs}$; φ fluorescence quantum yield; εφ brightness). Buffer: PBS pH 7.4.

| | $K_D$ μM | $10^{-7} \times k_{ON}$ $M^{-1}s^{-1}$ | $k_{OFF}$ $s^{-1}$ | $\lambda_{abs}$ nm | $\lambda_{em}$ nm | ε $M^{-1}cm^{-1}$ | φ % | εφ $M^{-1}cm^{-1}$ |
|---|---|---|---|---|---|---|---|---|
| HBR | 0.62 ± 0.05 | 3* (2.9 ± 5[§]) | 17* (8.5 ± 1.2[§]) | 467 | 537 | 44,000 | 9 | 4,000 |
| HMBR | 0.13 ± 0.01 | 6.3 ± 0.9 | 6.3 ± 0.7 | 481 | 555 | 45,000 | 33 | 15,000 |

*Kinetic constants at 25° C. extrapolated from kinetic parameters;
[§]Kinetic constants determined experimentally at 20° C.

Figure 12A:
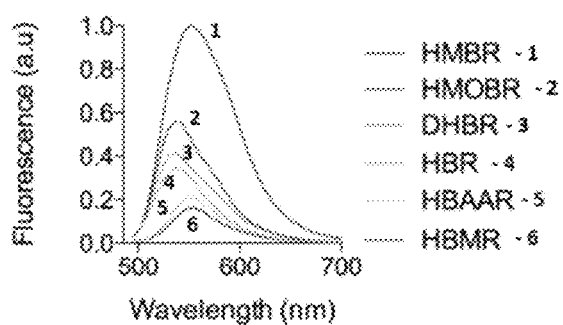
FIGS. 12A and B show fluorescence spectra (12A) of HBR analogs (12B) in presence of Y-FAST. HBR analogs (2 µM) were incubated with Y-FAST (40 µM) in PBS pH 7.4. Spectra were recorded at 25° C. (Ex 470 nm) with the exact same settings for direct comparison.
Figure 12B:
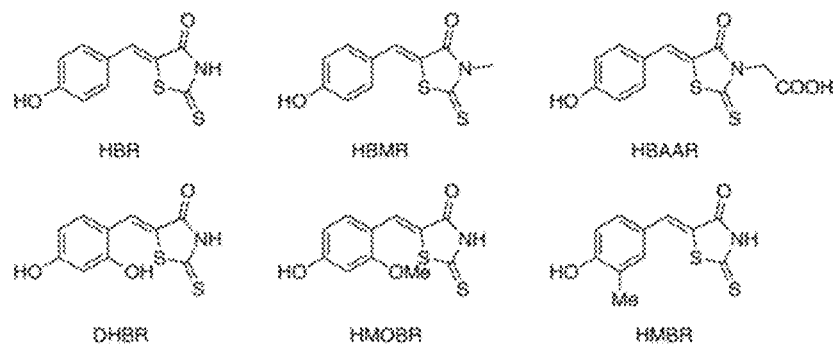
Figure 13:
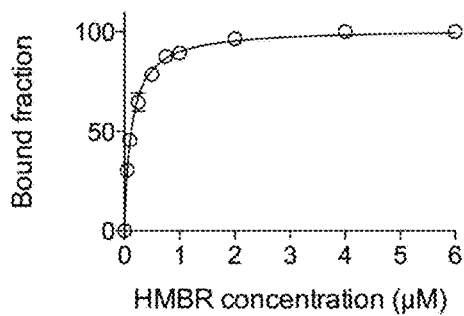
FIG. 13 is a graph showing the affinity of Y-FAST for HMBR. The graph shows the evolution of the bound fraction at equilibrium in function of HMBR concentration. Y-FAST concentration was 50 nM. The titration experiments were performed at 25° C. in PBS pH 7.4. Data represent mean±sem of 4 replicates. Least squares fit (line) gave the dissociation constant KD.

To improve the fluorescence performance of the system, we next introduced minor modifications on the fluorogen (FIG. 12). HMBR, which bears an additional methyl group on the aromatic ring, binds Y-FAST with a fivefold higher affinity (Table 3 and FIG. 13). The resulting complex still displays a red-shifted absorption and exhibits an enhanced fluorescence quantum yield of 33% (FIG. 14, Table 3), reaching thus the fluorescence performance of common fluorescent proteins. Determination of the on- and off-rate kinetic constants (Table 3) showed that, despite the gain in affinity, the binding was still fast (the relaxation time is 70 ms at 25° C. when [HMBR]=$K_D$) with rapid HMBR exchange between its free and bound states (the residence time is 160 ms at 25° C.).

To demonstrate that Y-FAST could be used for imaging fusion proteins by fluorescence microscopy, Y-FAST fused to Aga2p was expressed on the cell-surface of yeast cells.

Figure 11:
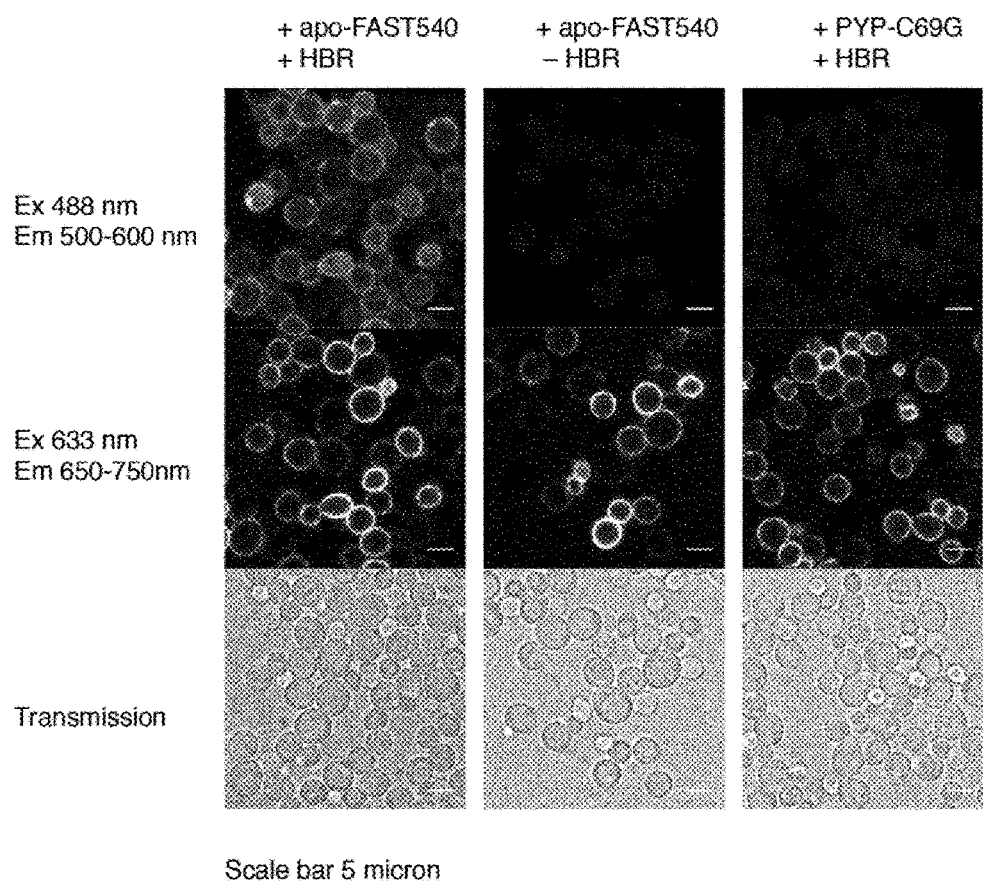
FIG. 11 displays photographs depicting confocal micrographs of yeast cells expressing either apo-Y-FAST of SEQ ID NO: 3 or PYP-C69G of SEQ ID NO: 48 (negative control) in presence of 20 µM HBR. Apo-Y-FAST and PYP-C69G bear a myc-tag for immunolabeling with Alex633-conjugated antibody. The green channel (Ex 488 nm-Em 500-600 nm) shows the specific fluorescence resulting from the excitation of Y-FAST with a 488 nm laser. The red channel (Ex 633 nm-Em 650-750 nm) shows the fluorescence resulting from the excitation of the Alexa633 with a 633 nm laser.

The yeast cells were imaged in presence of HBR with a confocal microscope and showed specific labeling of the cell-surface proteins (FIG. 11), demonstrating the ability of Y-FAST to act as a fluorescent tag for protein detection in living cells.

Figure 14A:
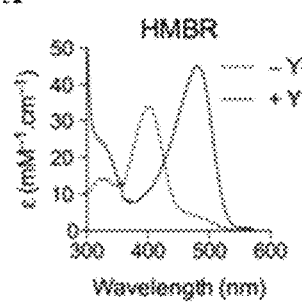
FIGS. 14A, B, C and D are a set of graphs and images showing that Y-FAST is a Yellow Fluorescence-Activating and absorption-Shifting Tag engineered from the photoactive yellow protein.
Figure 14B:
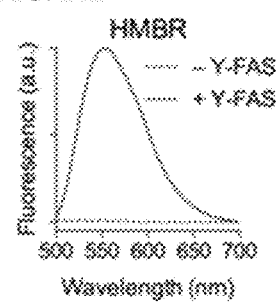
Figure 14C:
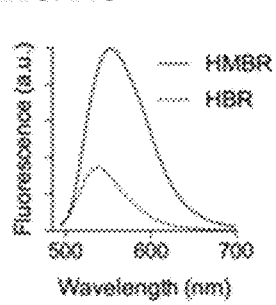
Figure 14D:
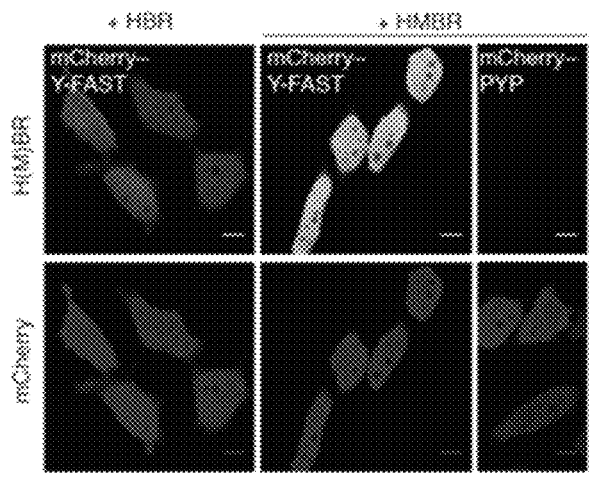
FIG. 14D shows the confocal micrographs of live Hela cells expressing mCherry-Y-FAST or mCherry-PYP labeled with 20 µM HBR or 5 µM HMBR (H(M)BR: Ex/Em 488/493-575 nm; mCherry: Ex/Em 543/578-797 nm; scale bars 10 µm). Images were recorded using the exact same settings for direct comparison of the fluorescence intensities. Plot shows fluorescence quantification of n=15-30 cells.
Figure 15A:
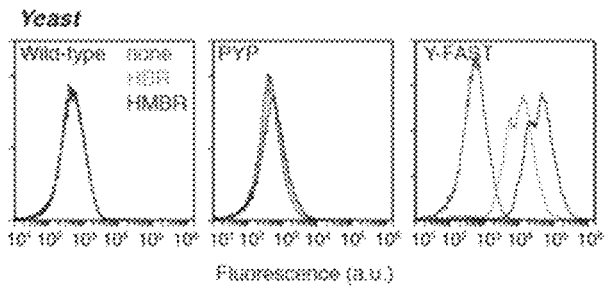
Figure 15B:
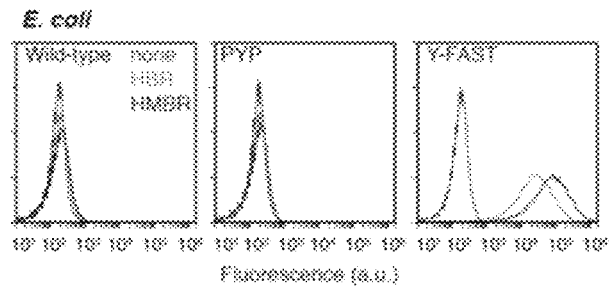
Figure 16:
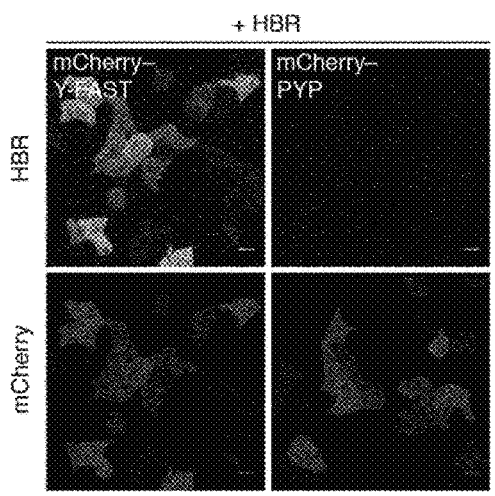
FIG. 16 is a set of confocal micrographs of live HEK293 cells expressing mCherry-Y-FAST or mCherry-PYP labeled with 20 µM HBR (HBR: Ex/Em 488/493-575 nm; mCherry: Ex/Em 543/578-797 nm; scale bars 10 µm). Images were recorded using the exact same settings for direct comparison of the fluorescence intensities.
Figure 17:
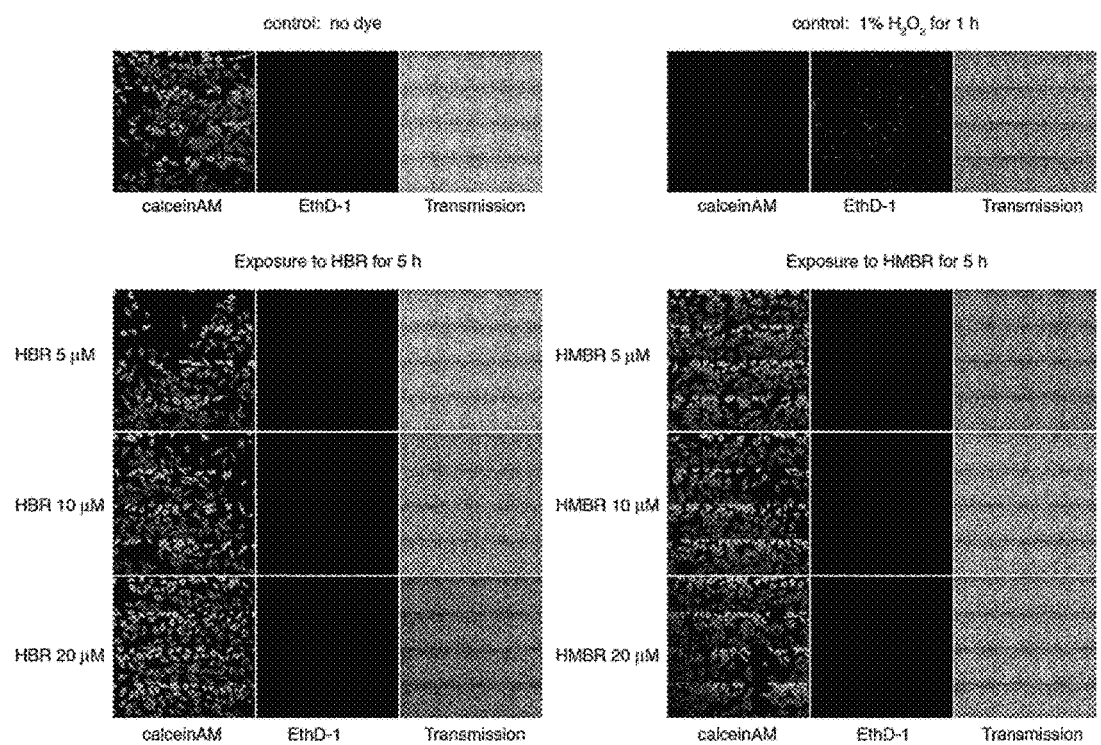
FIG. 17 is a set of images showing the results of a viability assay of HeLa cells incubated for 5 h with solutions of HBR and HMBR at 5, 10 and 20 µM. Cell viability was tested by using calceinAM and EthD1 (LIVE/DEAD® viability/cytotoxicity assay kit). CalceinAM is a cell-permeant profluorophore cleaved by intracellular esterases releasing the green fluorescent polyanionic calcein in live cells. EthD1 (Ethidium homodimer 1) is a non cell-permeant nucleic acid red fluorescent stain that enters only cells with damaged membranes and undergoes a fluorescence enhancement upon binding to nucleic acids, thereby producing a bright red fluorescence in dead cells. Control experiments with HeLa cells non-incubated with dye (top left, live control) or incubated for 1 h with 1% hydrogen peroxide (top right, dead control) are shown. Cell fluorescence was evaluated by confocal microscopy. The experiment shows that HBR and HMBR are non-toxic for HeLa cells at the concentrations used for imaging.

Labeling of Y-FAST with HBR and HMBR in cells was then analyzed by flow cytometry in three different expression systems: yeast, E. coli and mammalian cells (HeLa cells). The fluorescence was compared to wild-type cells or cells expressing wild-type PYP. The analysis showed that HBR and HMBR (i) generates no or negligible fluorescence background in wild-type bacteria, yeast and mammalian cells (FIG. 15a,b and FIG. 16), and (ii) do not bind wild-type PYP, demonstrating the high selectivity of Y-FAST labeling in living cells (FIG. 15a,b and FIG. 16). The analysis also showed that, as expected from the in vitro studies, HMBR outperforms HBR for fluorescently labeling Y-FAST in living cells. The performance and selectivity of Y-FAST labeling in mammalian cells, yeast and bacteria was furthermore confirmed by confocal microscopy (FIG. 14d and FIGS. 15 c to f and FIG. 16). HBR and HMBR were also shown to be non-toxic at the concentrations needed for imaging (FIG. 17), suggesting that Y-FAST should enable long-term imaging in mammalian cells.

Figure 18A:
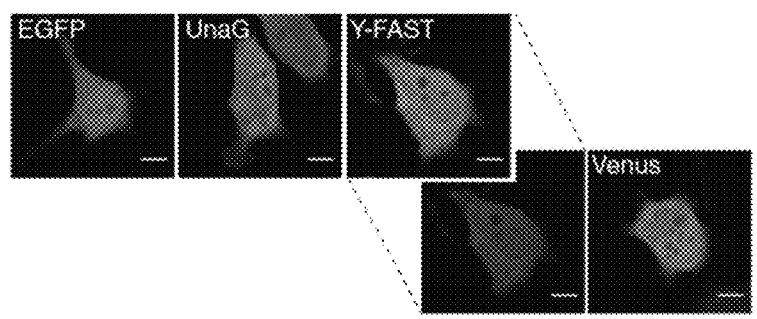
FIGS. 18A, B and C are a set of graphs and images showing Y-FAST brightness and photo-resistance in mammalian cells.
Figure 18B:
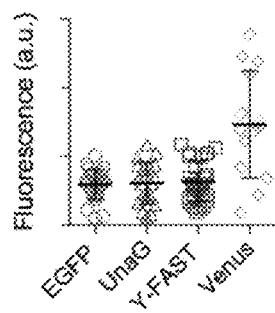
Figure 18C:
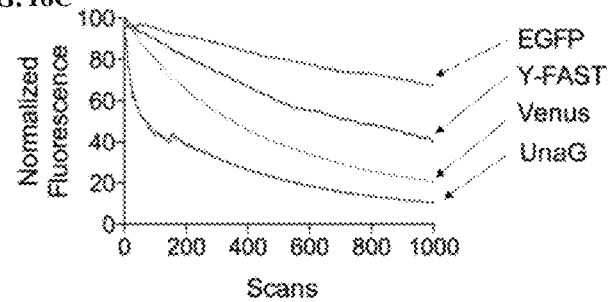
FIG. 18C shows the fluorescence levels of HeLa cells expressing EGFP, Y-FAST (labeled with 5 μM HMBR), Venus and UnaG upon long-term observation with high power 488 nm laser excitation (light power 90 kW·cm-2, pixel dwell 1.58 μs). Plots show the fluorescence intensity as a function of the number of confocal microscope scans.

The fluorescence of Y-FAST in mammalian cells upon blue excitation at 488 nm was shown to be comparable with that of the green fluorescent proteins EGFP and UnaG, and two fold lower than that of the yellow fluorescent Venus, one of the brightest fluorescent proteins (FIG. 18a). Upon green excitation at 514 nm, Y-FAST still fluoresces significantly, albeit five-fold less than Venus (FIG. 18a). Y-FAST was also shown to exhibit good photostability in cells. Under 488 nm excitation, Y-FAST was more stable than UnaG and Venus, but less than EGFP (FIG. 18b). However, upon excitation at 514 nm, Y-FAST almost did not photobleach unlike Venus that shows similar fading than upon 488 nm excitation (FIG. 18b). This behavior was confirmed by in-cuvette experiments (data not shown).

Figure 19D:
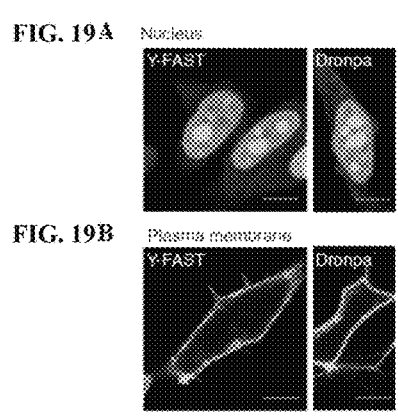
FIG. 19D shows the epifluorescence micrographs of a dendritic segment of a spinal cord neuron co-transfected with mCerulean-Gephyrin that accumulates at inhibitory synapses (Ex/Em 427/472±15 nm; left panel) and a Y-FAST-tagged Gephyrin construct (Ex/Em 504/542±14 nm; center). After 10 s of incubation with 10 μM HMBR, the fluorescence of Y-FAST was detected in the yellow emission range (Ex/Em 504/542±14 nm; right panel). Scale bars 10 μm.
Figure 19D:
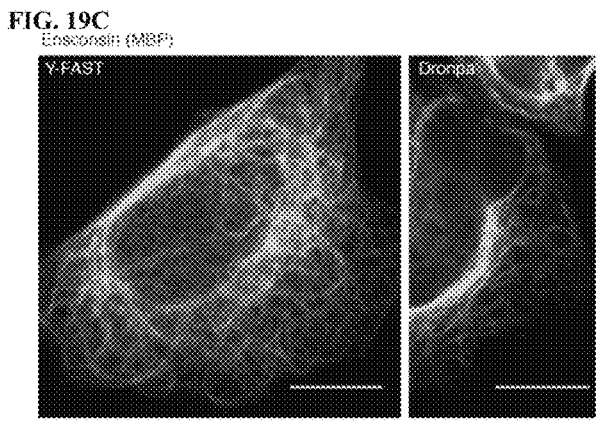
Figure 19D:
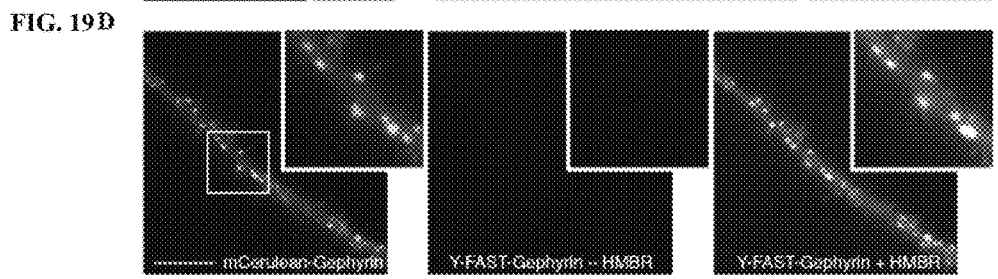

Y-FAST was next shown to be well suited for labeling proteins in various cell localizations. Labeling of cells expressing Y-FAST in fusion to a nuclear localization signal (NLS), to an inner-membrane targeting sequence (Lyn11), and to the microtubule-binding protein Ensconsin revealed the correct localization of the various fusions as demonstrated by comparing with similar fusions to the fluorescent protein Dronpa (FIG. 19a-c). To furthermore demonstrate that it could be used to label proteins in more confined cellular compartments, Y-FAST was fused to the synaptic scaffold protein Gephyrin for visualizing inhibitory synapses in dissociated spinal cord neurons. Epifluorescence imaging of Y-FAST-Gephyrin showed a punctate labeling after addition of HMBR, corresponding to post-synaptic clusters of Gephyrin at inhibitory synapses, as confirmed by co-localization with an mCerulean-tagged version of Gephyrin (FIG. 19d).

The labeling of Y-FAST was then validated in zebrafish embryo as model of a multicellular organism. Zebrafish embryos were microinjected with mRNA encoding mCherry-P2A-Y-FAST, where the P2A peptide mediates a cotranslational ribosome skipping enabling 1:1 co-expression of mCherry and Y-FAST. Embryos were incubated during gastrulation or at 24 hours post-fertilization with HMBR and imaged by spinning-disk microscopy. Labeling of Y-FAST revealed an expression pattern identical to that of mCherry (data not shown), demonstrating that Y-FAST labeling was specific in vivo. Additionally, evaluation of the fitness of embryos incubated with HMBR during development from 50% epiboly to 24 hpf showed that HMBR did not induce any mortality or perturbation in the development (data not shown), demonstrating that HMBR was non-toxic for zebrafish embryos and suggesting that Y-FAST should enable long-term imaging in zebrafish.

Figure 20:
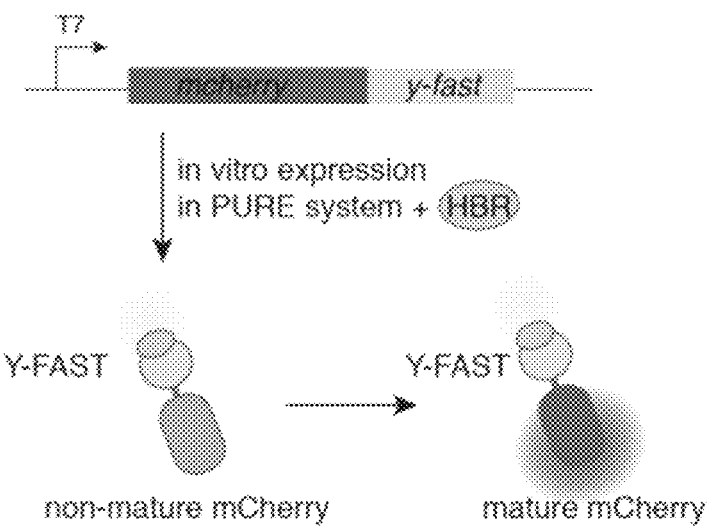
FIGS. 20A, B and C are a combination of a drawing and graphs showing that Y-FAST enables to follow protein synthesis in near real-time.
FIG. 20B: temporal evolution of the fluorescence emission at 540 nm (Ex 470 nm) and 610 nm (Ex 587 nm) corresponding respectively to the emission of Y-FAST and mCherry.
FIG. 20C: a gene encoding Y-FAST fused to mCherry (mCherry-Y-FAST) was expressed in vitro in the cell-free PURE system in presence of 5 μM HMBR at 37° C. The line 1 shows the temporal evolution of Y-FAST emission while the line 2 shows the temporal evolution of mCherry emission. Note that the drop of Y-FAST emission over time reflects mainly the energy transfer to mature mCherry. The plot also shows the temporal luminescence evolution during in vitro synthesis of EGFP (green dashed line), UnaG in presence of 5 μM bilirubin (cyan dashed line), Venus (yellow dashed line) and Firefly luciferase in presence of luciferin (black dashed line). In all the experiments, the genes were under the control of the same T7 promoter. Data represent the mean of three replicates.
Figure 20:
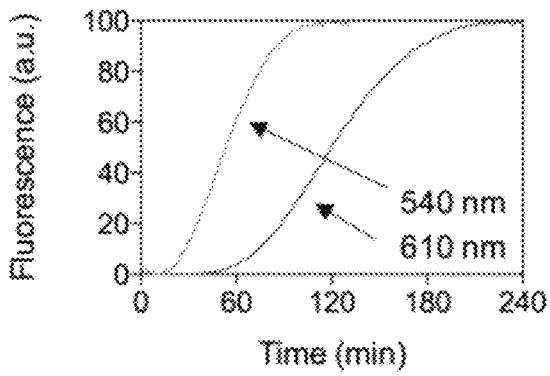
Figure 20:
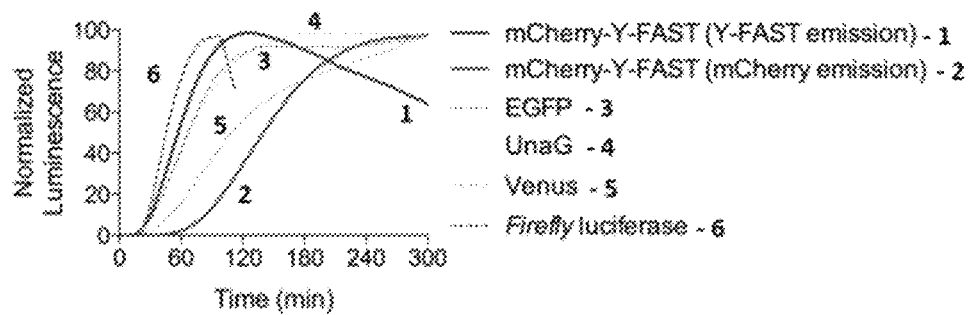

Since Y-FAST is fluorescent almost instantaneously provided that HMBR is already present, we anticipated that it could outperform GFP-like fluorescent proteins to monitor rapid processes such as protein synthesis in real-time. Some GFP-like fluorescent proteins fail to report on protein synthesis in real-time since the rate of appearance of their fluorescence depends not only on the protein synthesis itself but also on the post-translational formation of their chromophore. To show the advantage of Y-FAST in this context, we followed the cell-free expression of a fusion construct of mCherry and Y-FAST by monitoring simultaneously their fluorescence (FIG. 20). Even though a single protein was synthesized, we observed two different rates of appearance for Y-FAST and mCherry fluorescence: while Y-FAST could be already detected as soon as 10 min after the initiation of the protein synthesis reaching saturation within 90 min, the mCherry signal only started to appear after 50 min and took over 4 hours to reach saturation as a result of the slow maturation of its chromophore. We next compared the expression of mCherry-Y-FAST with that of EGFP and Venus, reported to mature within 10 and 40 min in vitro, respectively, the bilirubin-inducible UnaG, and the Firefly luciferase that is often employed as reporter of protein synthesis. Although the expression of the different proteins was controlled by the same T7 promoter and should therefore occurs at the same rate, we observed various rates of luminescence appearance (FIG. 20). Our experiments showed that Y-FAST clearly outperforms Venus and mCherry to report on protein synthesis in near real-time, and provides roughly the same kinetic information as Firefly luciferase, EGFP and UnaG.

The spectral properties of Y-FAST make it well suited for FRET experiments, as it could play the acceptor in a pair with CFP or the donor in a pair with mCherry. To demonstrate the potential of Y-FAST for FRET experiments, we characterized the FRET efficiency in a fusion between Y-FAST and mCherry. We showed that the FRET efficiency was ~50%, in agreement with a donor-acceptor distance of 5 nm.

Figure 21B:
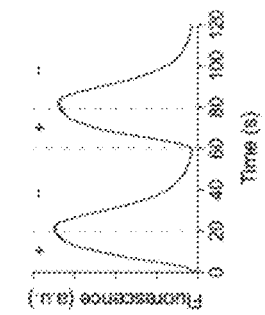
Figure 21A:
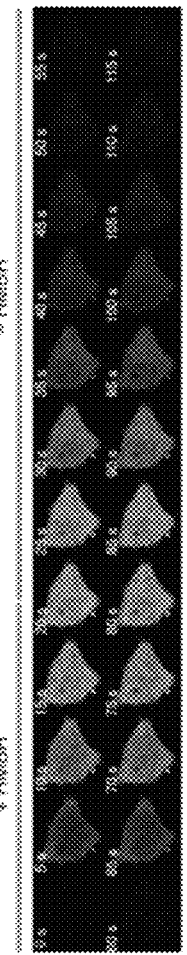
FIGS. 21A, B and C are a set of graphs and images showing that Y-FAST fluorescence can be switched on and off by addition and withdrawal of the fluorogenic ligand.
Figure 22:
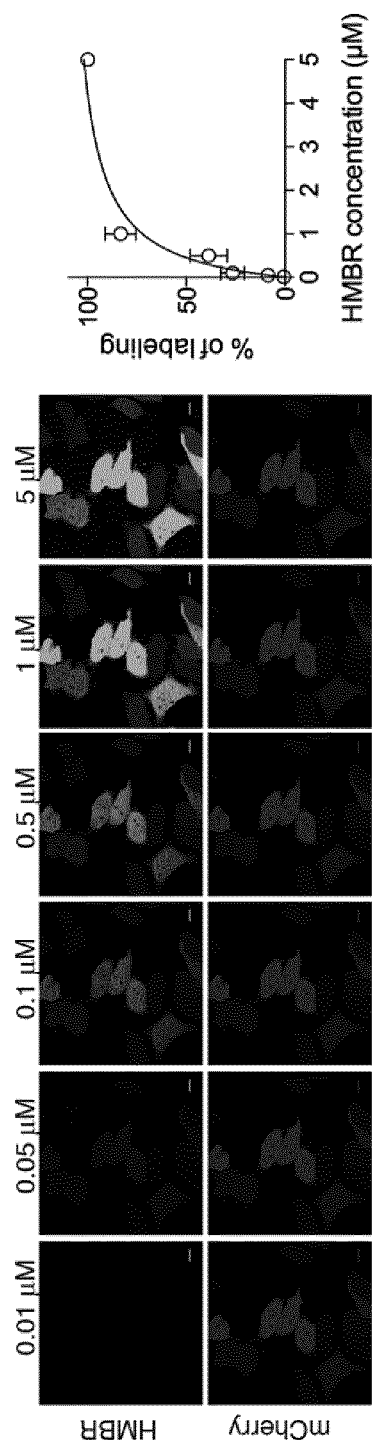
FIG. 22 is a set of graphs and images showing that Y-FAST enables the control of the density of fluorescent labeling independently of the expression level. Confocal micrographs of live HeLa cells expressing mCherry fused to Y-FAST incubated with various concentrations of HMBR (HMBR channel: Ex/Em 488/493-575 nm, mCherry channel: Ex/Em 543/578-797 nm; scale bars 10 μm). Plot shows the percentage of labeling as a function of the concentration. Data represents mean±SD (n=15).

Finally, we showed that Y-FAST fluorescence was highly tunable. The density of emitters could be controlled independently of the expression level of the protein by tuning the fluorogen concentration (FIG. 22). Titration in cells was in good agreement with the in vitro results, showing, firstly, that the concentration of HMBR in the milieu reflected its intracellular level and, secondly, that 1 μM HMBR was sufficient for full labeling in cells. Moreover, we showed that it is possible to rapidly switch on and off Y-FAST in mammalian cells by rapid addition or withdrawal of HMBR. To show this, we used a microfluidic device coupled to a multifunctional fluidic controller. Labeling with HMBR occurs within about ten seconds, in accordance with a good cell permeability of HMBR and an immediate formation of the complex (FIG. 21a,b). Rapid replacement of the HMBR-containing medium with HMBR-free medium unlabeled proteins at a similar timescale (FIG. 21a,b), in accordance with the short residence time of HMBR. Thanks to the multifunctional fluidic controller, the labeling and unlabeling of Y-FAST could be repeated more than ten times by switching rapidly between the labeling solution and the washing solution (FIG. 21a,b).

Figure 21C:
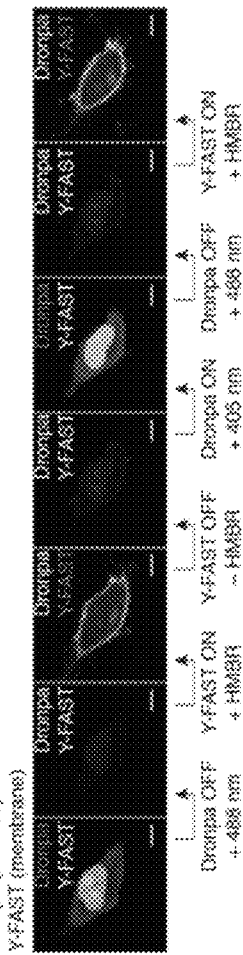
FIG. 21C shows the confocal micrographs of live HeLa cells expressing Dronpa-NLS (nucleus) and lyn11-Y-FAST (membrane) showing sequential imaging of nuclear Dronpa and membrane-anchored Y-FAST thanks to sequential on/off labeling of Y-FAST intercalated with on/off photoswitching of Dronpa (Ex/Em 488/493-797 nm). HMBR concentration was 5 μM. Scale bars 10 μm.

The ability to switch on and off the fluorescence by addition and withdrawal of a fluorogenic ligand makes it possible to image targets that are indistinguishable spectrally by sequential rounds of fluorogenic labeling, imaging and fluorogen removal. To demonstrate this strategy, we expressed Y-FAST (fused to Lyn-11 for membrane anchoring) and the photoswitchable fluorescent protein Dronpa (fused to a nuclear localization signal) in mammalian cells (FIG. 21c). We first imaged cells in absence of HMBR to visualize nuclear Dronpa, then switched off Dronpa by 488 nm excitation and added HMBR to label Y-FAST. We could then selectively observe Y-FAST membrane localization. Washing HMBR away unlabeled Y-FAST, enabling again to selectively visualize Dronpa (photoactivated by exciting at 405 nm) without any pollution from Y-FAST. The process could be repeated by switching off Dronpa and labeling Y-FAST with HMBR (FIG. 21c).

BIBLIOGRAPHY

Airaksinen, A., and Hovi, T. (1998). Modified base compositions at degenerate positions of a mutagenic oligonucleotide enhance randomness in site-saturation mutagenesis. Nucleic Acids Res.

Auldridge, M. E., Satyshur, K. A., Anstrom, D. M., and Forest, K. T. (2012). Structure-guided Engineering Enhances a Phytochrome-based Infrared Fluorescent Protein. J Biol Chem 287, 7000-7009.

Borgstahl, G., Williams, D., and Getzoff, E. D. (1995). 1.4 .ANG. Structure of Photoactive Yellow Protein, a Cytosolic Photoreceptor: Unusual Fold, Active Site, and Chromophore—Biochemistry (ACS Publications). Biochemistry.

Chao, G., Lau, W. L., Hackel, B. J., Sazinsky, S. L., Lippow, S. M., and Wittrup, K. D. (2006). Isolating and engineering human antibodies using yeast surface display. Nat Protoc 1, 755-768.

Chapman, S., Faulkner, C., Kaiserli, E., Garcia-Mata, C., Savenkov, E. I., Roberts, A. G., Oparka, K. J., and Christie, J. M. (2008). The photoreversible fluorescent protein iLOV outperforms GFP as a reporter of plant virus infection. P Natl Acad Sci Usa 105, 20038-20043.

Chudakov, D. M., Matz, M. V., Lukyanov, S., and Lukyanov, K. A. (2010). Fluorescent Proteins and Their Applications in Imaging Living Cells and Tissues. Physiol Rev 90, 1103-1163.

Derbyshire, K. M., Salvo, J. J., and Grindley, N. D. F. (1986). A simple and efficient procedure for saturation mutagenesis using mixed oligodeoxynucleotides. Gene 46, 145-152.

Drepper, T., Eggert, T., Circolone, F., Heck, A., Krauβ, U., Guterl, J.-K., Wendorff, M., Losi, A., Gärtner, W., and Jaeger, K.-E. (2007). Reporter proteins for in vivo fluorescence without oxygen. Nat Biotechnol 25, 443-445.

Filonov, G. S., Piatkevich, K. D., Ting, L.-M., Zhang, J., Kim, K., and Verkhusha, V. V. (2011). Bright and stable near-infrared fluorescent protein for in vivo imaging. Nat Biotechnol 29, 759-763.

Gietz, R. D., and Schiestl, R. H. (2007). Large-scale high-efficiency yeast transformation using the LiAc/SS carrier DNA/PEG method. Nat Protoc 2, 38-41.

Hansen, M. C., Palmer, R. J., Udsen, C., White, D. C., and Molin, S. (2001). Assessment of GFP fluorescence in cells of Streptococcus gordonii under conditions of low pH and low oxygen concentration. Microbiology (Reading, Engl.) 147, 1383-1391.

Heim, R., Cubitt, A. B., and Tsien, R. Y. (1995). Improved green fluorescence. Nature 373, 663-664.

Kumagai, A., Ando, R., Miyatake, H., Greimel, P., Kobayashi, T., Hirabayashi, Y., Shimogori, T., and Miyawaki, A. (2013). A Bilirubin-Inducible Fluorescent Protein from Eel Muscle. Cell 153, 1602-1611.

Miyazaki, K., and Arnold, F. H. (1999). Exploring Nonnatural Evolutionary Pathways by Saturation Mutagenesis: Rapid Improvement of Protein Function. J Mol Evol 49, 716-720.

Ozhalici-Unal, H., Pow, C. L., Marks, S. A., Jesper, L. D., Silva, G. L., Shank, N. I., Jones, E. W., Burnette, J. M., Berget, P. B., and Armitage, B. A. (2008). A rainbow of fluoromodules: A promiscuous scFv protein binds to and activates a diverse set of fluorogenic cyanine dyes. J Am Chem Soc 130, 12620-12621.

Shaner, N., Steinbach, P., and Tsien, R. (2005). A guide for choosing fluorescent proteins. Nat. Meth. 2, 905-909.

Shank, N. I., Zanotti, K. J., Lanni, F., Berget, P. B., and Armitage, B. A. (2009). Enhanced Photostability of Genetically Encodable Fluoromodules Based on Fluorogenic Cyanine Dyes and a Promiscuous Protein Partner. J Am Chem Soc 131, 12960-12969.

Shapiro, H. M. (2003). Practical flow cytometry (Wiley).

Shu, X., Royant, A., Lin, M. Z., Aguilera, T. A., Lev-Ram, V., Steinbach, P. A., and Tsien, R. Y. (2009). Mammalian Expression of Infrared Fluorescent Proteins Engineered from a Bacterial Phytochrome. Science 324, 804-807.

Shu, X., Lev-Ram, V., Deerinck, T. J., Qi, Y., Ramko, E. B., Davidson, M. W., Jin, Y., Ellisman, M. H., and Tsien, R. Y. (2011). A Genetically Encoded Tag for Correlated Light and Electron Microscopy of Intact Cells, Tissues, and Organisms. PLoS Biol 9, e1001041.

Steffens, D. L., and Williams, J. G. K. (2007). Efficient site-directed saturation mutagenesis using degenerate oligonucleotides. J Biomol Tech 18, 147-149.

Szent-Gyorgyi, C., Schmidt, B. A., Creeger, Y., Fisher, G. W., Zakel, K. L., Adler, S., Fitzpatrick, J. A. J., Woolford, C. A., Yan, Q., Vasilev, K. V., et al. (2008). Fluorogen-activating single-chain antibodies for imaging cell surface proteins. Nat Biotechnol 26, 235-240.

Tsien, R. Y. (1998). The green fluorescent protein. Annu Rev Biochem 67, 509-544.

Wang, J., Zhang, S., Tan, H., and Zhao, Z. K. (2007). PCR-based strategy for construction of multi-site-saturation mutagenic expression library. J Microbiol Methods 71, 225-230.

Zheng, L. (2004). An efficient one-step site-directed and site-saturation mutagenesis protocol. Nucleic Acids Res 32, e115-e115.

The invention claimed is:

1. A a functional photoactive yellow protein (PYP) polypeptide comprising the sequence of SEQ ID NO: 48, or a sequence having at least 70% identity with the sequence of SEQ ID NO: 48, wherein said sequence further comprises one or more amino acid substitutions in the amino acid region at position 94-101 with reference to SEQ ID NO: 48, one of said substitutions being a proline at position 97 with reference to SEQ ID NO: 48, and wherein said polypeptide binds reversibly a fluorogenic chromophore with:
- a $K_D$ ranging from about 0.05 to about 10 μM when measured at a temperature of about 25° C.; and/or
- a $k_{off}$ ranging from about 1 to about 50 s$^{-1}$ when measured at a temperature of about 25° C.; and/or
- a $k_{on}$ ranging from about 0.1×10$^7$ to about 50×10$^7$ M$^{-1}$s$^{-1}$ when measured at a temperature of about 25° C.

2. The functional PYP polypeptide according to claim 1, comprising the sequence selected from the group consisting of SEQ ID NO: 48, SEQ ID NO: 49, SEQ ID NO: 50, SEQ ID NO: 51, SEQ ID NO: 52, SEQ ID NO: 53, SEQ ID NO: 54, and SEQ ID NO: 55.

3. The functional PYP polypeptide according to claim 1, wherein the one or more amino acid substitutions in the amino acid region at position 94-101 of SEQ ID NO: 48 or at a corresponding position of the sequence having at least 70% identity with the sequence of SEQ ID NO: 48 comprise one of:
- a tryptophan at position 94;
- an amino acid residue with branched aliphatic side chain selected from isoleucine, valine or leucine, at position 96; or
- a threonine at position 98;
with reference to SEQ ID NO: 48.

4. The functional PYP polypeptide according to claim 1, wherein the one or more amino acid substitutions in the amino acid region at position 94-101 of SEQ ID NO: 48 or at a corresponding position of a sequence having at least 70% identity with the sequence of SEQ ID NO: 48 comprise two of:
- a tryptophan at position 94;
- an amino acid residue with branched aliphatic side chain selected from isoleucine, valine or leucine, at position 96; and/or
- a threonine at position 98;
with reference to SEQ ID NO: 48.

5. The functional PYP polypeptide according to claim 1, wherein the one or more amino acid substitutions in the amino acid region at position 94-101 of SEQ ID NO: 48 or at a corresponding position of a sequence having at least 70% identity with the sequence of SEQ ID NO: 48 comprise:
- a tryptophan at position 94;
- an amino acid residue with branched aliphatic side chain selected from isoleucine, valine or leucine, at position 96; and
- a threonine at position 98;
with reference to SEQ ID NO: 48.

6. The functional PYP polypeptide according to claim 1, comprising an amino acid region at position 94-101 of SEQ ID NO: 48 or at a corresponding position of a sequence having at least 70% identity with the sequence of SEQ ID NO: 48 selected from the group consisting of SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127 and SEQ ID NO: 128.

7. The functional PYP polypeptide according to claim 1, wherein the sequence as set forth in SEQ ID NO: 48 further comprises one or more amino acid substitutions in the amino acid region at position 94-101, one of said substitutions being a proline at position 97, is a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO:

38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 and SEQ ID NO: 47.

8. The functional PYP polypeptide according to claim 1, wherein the fluorogenic chromophore has a formula (I):

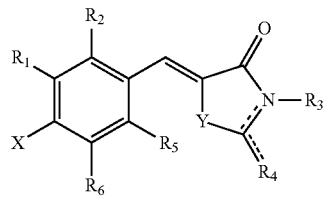

formula (I)

wherein
- R1, R2, R5 and R6 may be identical or different and each represents H, halo, hydroxyl, aryl, alkyl, cycloalkyl, heteroalkyl or heterocycloalkyl group, saturated or unsaturated, linear or branched, unsubstituted or substituted by at least one group selected from halo, hydroxyl, oxo, nitro, amido, carboxy, amino, cyano, haloalkoxy, haloalkyl;
- R3 represents a non-binding doublet (i.e. a free pair of electrons) or H, halo, hydroxyl, aryl, alkyl, cycloalkyl, heteroalkyl or heterocycloalkyl group, saturated or unsaturated, linear or branched, unsubstituted or substituted by at least one group selected from halo, hydroxyl, oxo, nitro, amido, carboxy, amino, cyano, haloalkoxy, haloalkyl;
- R4 is a single or a double bound, interrupted or terminated by S, O or N atom, unsubstituted or substituted by at least one group selected from H, hydroxyl, aryl, alkyl, cycloalkyl, heteroalkyl or heterocycloalkyl group, saturated or unsaturated, linear or branched, unsubstituted or substituted by at least one group selected from halo, hydroxyl, oxo, nitro, amido, carboxy, amino, cyano, haloalkoxy, haloalkyl;
- X is OH, SH, NHR7, or N(R7)$_2$, wherein R7 is H, halo, hydroxyl, aryl, alkyl, cycloalkyl, heteroalkyl or heterocycloalkyl group, saturated or unsaturated, linear or branched, unsubstituted or substituted by at least one group selected from halo, hydroxyl, oxo, nitro, amido, carboxy, amino, cyano, haloalkoxy, haloalkyl; and
- Y is O, NH or S.

9. The functional PYP polypeptide according to claim 1, wherein the fluorogenic chromophore has a formula (II), (III), (IV), (V), (VI), (VII) or (VIII):

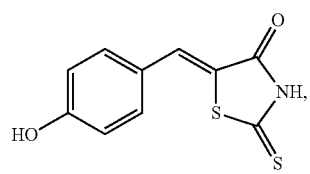

formula (II)

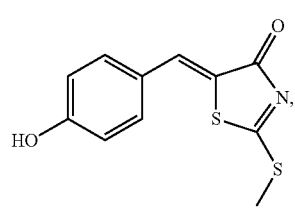

formula (III)

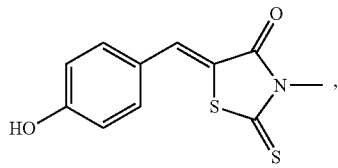

formula (IV)

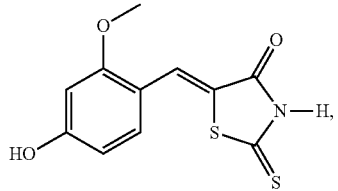

formula (V)

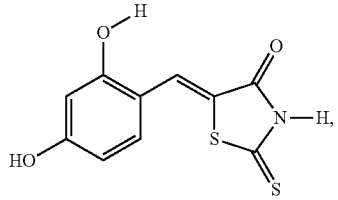

formula (VI)

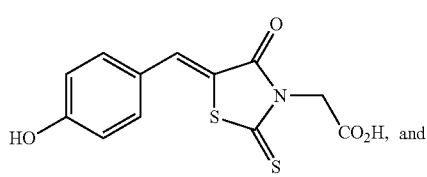

formula (VII)

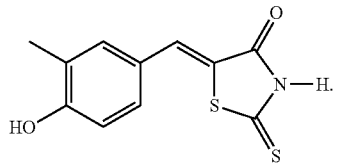

formula (VIII)

10. The functional PYP polypeptide according to claim 1 fused to a protein of interest.

11. A polynucleotide encoding the functional PYP polypeptide according to claim 1.

12. A method for quantifying and/or detecting protein activity, protein localization, protein-protein interactions, and/or protein relocation in any solid or liquid sample, cells or tissues or organisms of interest, comprising:
- binding the target to quantify and/or detect with a functional photoactive yellow protein (PYP) polypeptide, wherein said polypeptide has a sequence as set forth in SEQ ID NO: 48 or a sequence having at least 70% identity with the sequence of SEQ ID NO: 48, said sequence further comprising one or more amino acid substitutions in the amino acid region at position 94-101 with reference to SEQ ID NO: 48, one of said substitutions being a proline at position 97 with reference to SEQ ID NO: 48, and wherein said polypeptide binds reversibly a fluorogenic chromophore with
- a $K_D$ ranging from about 0.05 to about 10 µM when measured at a temperature of about 25° C.; and/or
- a $k_{off}$ ranging from about 1 to about 50s$^{-1}$ when measured at a temperature of about 25° C.; and/or
- a $k_{on}$ ranging from about 0.1×10$^7$ to about 50×10$^7$ M$^{-1}$s$^{-1}$ when measured at a temperature of about 25° C.; and
- providing a fluorogenic chromophore.

13. The method of claim 12 for fluorescently labeling or coloring a surface or a particle comprising the steps of:
  binding to the surface or particle a functional photoactive yellow protein (PYP) polypeptide, wherein said polypeptide has a sequence as set forth in SEQ ID NO: 48 or a sequence having at least 70% identity with the sequence of SEQ ID NO: 48, said sequence further comprising one or more amino acid substitutions in the amino acid region at position 94-101 with reference to SEQ ID NO: 48, one of said substitutions being a proline at position 97 with reference to SEQ ID NO: 48, and wherein said polypeptide binds reversibly a fluorogenic chromophore with:
    a $K_D$ ranging from about 0.05 to about 10 μM when measured at a temperature of about 25° C.; and/or
    a $K_{off}$ ranging from about 1 to about 50 $s^{-1}$ when measured at a temperature of about 25° C.; and/or
    a $k_{on}$ ranging from about $0.1 \times 10^7$ to about $50 \times 10^7$ $M^{-1}s^{-1}$ when measured at a temperature of about 25° C.; and
  providing a fluorogenic chromophore.

14. The method of claim 12 for sequentially labelling proteins in a sample with at least two functional photoactive yellow protein (PYP) polypeptides, wherein said polypeptides have a sequence as set forth in SEQ ID NO: 48 or a sequence having at least 70% identity with the sequence of SEQ ID NO: 48, said sequence further comprising one or more amino acid substitutions in the amino acid region at position 94-101 with reference to SEQ ID NO: 48, one of said substitutions being a proline at position 97 with reference to SEQ ID NO: 48, binding to at least two fluorogenic chromophores with:
  a $K_D$ ranging from about 0.05 to about 10 μM when measured at a temperature of about 25° C.; and/or
  a $k_{off}$ ranging from about 1 to about 50 $s^{-1}$ when measured at a temperature of about 25° C.; and/or
  a $k_{on}$ ranging from about $0.1 \times 10^7$ to about $50 \times 10^7$ $M^{-1}s^{-1}$ when measured at a temperature of about 25° C.;
  wherein the method comprises:
    contacting said sample with a first fluorogenic chromophore;
    measuring fluorescence;
    washing the sample to turn the fluorescence off;
    contacting said sample with a second fluorogenic chromophore;
    measuring fluorescence;
    washing the sample to turn the fluorescence off;
    repeating the previous steps with each fluorogenic chromophore.

15. A method of identifying functional photoactive yellow protein PYP polypeptides capable of binding to a fluorogenic chromophore with:
  a $K_D$ ranging from about 0.05 to about 10 μM when measured at a temperature of about 25° C.; and/or
  a $k_{off}$ ranging from about 1 to about 50 $s^{-1}$ when measured at a temperature of about 25° C.; and/or
  a $k_{on}$ ranging from about $0.1.10^7$ to about $50.10^7$ $M^{-1}s^{-1}$ when measured at a temperature of about 25° C.;
  wherein said method comprises:
    randomly mutating a PYP sequence comprising a proline at position 97 with reference to SEQ ID NO:48, wherein the PYP sequence is selected from SEQ ID NO: 48-81;
    measuring the kinetic constant of association of mutated PYP with the fluorogenic chromophore; and
    selecting mutated PYP with specified $K_D$, $k_{on}$ and/or $k_{off}$.

* * * * *